US008597880B2

(12) United States Patent
Tapscott et al.

(10) Patent No.: US 8,597,880 B2
(45) Date of Patent: Dec. 3, 2013

(54) METHODS AND COMPOSITIONS FOR IDENTIFYING INCREASED RISK OF DEVELOPING FRAGILE X-ASSOCIATED DISORDERS

(75) Inventors: Stephen J. Tapscott, Seattle, WA (US); Galina N. Filippova, Seattle, WA (US); Paula D. Ladd, Seattle, WA (US)

(73) Assignee: The Fred Hutchinson Cancer Research Center, Seattle, WA (US)

( * ) Notice: Subject to any disclaimer, the term of this patent is extended or adjusted under 35 U.S.C. 154(b) by 579 days.

(21) Appl. No.: 12/681,433

(22) PCT Filed: Oct. 2, 2008

(86) PCT No.: PCT/US2008/011406
§ 371 (c)(1),
(2), (4) Date: Jun. 30, 2010

(87) PCT Pub. No.: WO2009/045467
PCT Pub. Date: Apr. 9, 2009

(65) Prior Publication Data
US 2010/0279293 A1   Nov. 4, 2010

Related U.S. Application Data

(60) Provisional application No. 60/976,926, filed on Oct. 2, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| 6,180,337 | B1 | 1/2001 | Caskey et al. |
| 2005/0037992 | A1 | 2/2005 | Lyons et al. |
| 2006/0270727 | A1 | 11/2006 | Melander et al. |

FOREIGN PATENT DOCUMENTS

WO   WO2008011170   *   1/2008

OTHER PUBLICATIONS

Ladd et al. "*ASFMR1*, an Antisense Transcript Spanning the CGG Repeat Region of *FMR1*, is Upregulated in Premutation Carriers but Silenced in Full Mutation Individuals" Abstract for presentation made Oct. 5, 2007 at the *13th International Workshop on Fragile X and X-Linked Mental Retardation*, which took place in Venice, Italy on Oct. 3-6, 2007 (2 pages) and Scientific Program for same (6 pages).

Hessl et al. "Abnormal Elevation of *FMR1* mRNA is Associated With Psychological Symptoms in Individuals With the Fragile X Premutation" *American Journal of Medical Genetics* Part B 139B:115-121 (2005).

International Search Report and Written Opinion for International Application No. PCT/US2008/011406 (mailed Mar. 2, 2009) (13 pages).

Ladd et al. "An Antisense Transcript Spanning the CGG Repeat Region of *FMR1* is Upregulated in Premutation Carriers but Silenced in Full Mutation Individuals" *Human Molecular Genetics* 16(24):3174-3187 (2007).

Primerano et al. "Reduced *FMR1* mRNA Translation Efficiency in Fragile X Patients With Premutations" *RNA* 8:1482-1488 (2002).

Arocena et al. "Induction of Inclusion Formation and Disruption of Lamin A/C Structure by Premutation CGG-Repeat RNA in Human Cultured Neural Cells" *Human Molecular Genetics* 14(23):3661-3671 (2005).

Barski et al. "High-Resolution Profiling of Histone Methylations in the Human Genome" *Cell* 129:823-837 (2007).

Beilina et al. "Redistribution of Transcription Start Sites Within the *FMR1* Promoter Region with Expansion of the Downstream CGG-Repeat Element" *Human Molecular Genetics* 13(5):543-549 (2004).

Bell et al. "Insulators and Boundaries: Versatile Regulatory Elements in the Eukaryotic Genome" *Science* 291:447-450 (2001).

Chiurazzi et al. "No Apparent Involvement of the FMR1 Gene in Five Patients with Phenotypic Manifestations of the Fragile X Syndrome" *American Journal of Medical Genetics* 51:309-314 (1994).

Cho et al. "Antisense Transcription and Heterochromatin at the *DM1* CTG Repeats are Constrained by CTCF" *Molecular Cell* 20:483-489 (2005).

Dombrowski et al. "Premutation and Intermediate-Size *FMR1* Alleles in 10 572 Males from the General Population: Loss of an AGG Interruption is a Late Event in the Generation of Fragile X Syndrome Alleles" *Human Molecular Genetics* 11(4):371-378 (2002).

Drouin et al. "Structural and Functional Characterization of the Human FMR1 Promoter Reveals Similarities with the hnRNP-A2 Promoter Region" *Human Molecular Genetics* 6(12):2051-2060 (1997).

Fardaei et al. "Three Proteins, MBNL, MBLL and MBXL, Co-Localize In Vivo with Nuclear Foci of Expanded-Repeat Transcripts in DM1 and DM2 Cells" *Human Molecular Genetics* 11(7):805-814 (2002).

Flippova "Genetics and Epigenetics of the Multifunctional Protein CTCF" *Current Topics in Developmental Biology* 80:337-360 (2008).

(Continued)

*Primary Examiner* — Jehanne Sitton
(74) *Attorney, Agent, or Firm* — Myers Bigel Sibley & Sajovec, PA

(57) ABSTRACT

The present invention provides compositions and methods of identifying a subject as having an increased risk of developing fragile X-associated tremor and ataxia syndrome (FX-TAS) or identifying a subject having an increased risk of developing fragile X syndrome (FXS), comprising analyzing messenger RNA (mRNA) transcripts and/or translation products of the antisense gene ASFMR1.

2 Claims, 9 Drawing Sheets

(56) References Cited

OTHER PUBLICATIONS

Flippova et al. "CTCF-Binding Sites Flank CTG/CAG Repeats and Form a Methylation-Sensitive Insulator at the *DM1* Locus" *Nature Genetics* 28:335-343 (2001).
Flippova et al. "Boundaries Between Chromosomal Domains of X Inactivation and Escape Bind CTCF and Lack CpG Methylation During Early Development" *Developmental Cell* 8:31-42 (2005).
Greco et al. "Neuronal Intranuclear Inclusions in a New Cerebellar Tremor/Ataxia Syndrome Among Fragile X Carriers" *Brain* 125:1760-1771 (2002).
Greco et al. "Neuropathology of Fragile X-Associated Tremor/Ataxia Syndrome (FXTAS)" *Brain* 129:243-255 (2006).
Grewal et al. "Heterochromatin Revisited" *Nat. Rev. Genet* 8:35-46 (2007).
Hagerman et al. "The Fragile-X Premutation: A Maturing Perspective" *Am. J. Hum. Genet*. 74:805-816 (2004).
Handa et al. "The Fragile X Syndrome Repeats Form RNA Hairpins that do not Activate the Interferon-Inducible Protein Kinase, PKR, but are Cut by Dicer" *Nucleic Acids Research* 31(21):6243-6248 (2003).
Hansen et al. "Role of Late Replication Timing in the Silencing of X-Linked Genes" *Human Molecular Genetics* 5(9):1345-1353 (1996).
Hansen et al. "Methylation Analysis of CGG Sites in the CpG Island of the Human *FMR1* Gene" *Human Molecular Genetics* 1(8):571-578 (1992).
Hinds et al. "Tissue Specific Expression of *FMR-1* Provides Evidence for a Functional Role in Fragile X Syndrome" *Nature Genetics* 3:36-43 (1993).
Iwahashi et al. "Protein Composition of the Intranuclear Inclusions of FXTAS" *Brain* 129:256-271 (2006).
Jacquemont et al. "Penetrance of the Fragile X-Associated Tremor/Ataxia Syndrome in a Premutation Carrier Population" *JAMA* 291(4):460-469 (2004).
Kenneson et al. "Reduced FMRP and Increased *FMR1* Transcription is Proportionally Associated with CGG Repeat Number in Intermediate-Length and Premutation Carriers" *Human Molecular Genetics* 10(14):1449-1454 (2001).
Kino et al. "Muscleblind Protein, MBNL1/EXP, Binds Specifically to CHHG Repeats" *Human Molecular Genetics* 13(5):495-507 (2004).
Krol et al. "Ribonuclease Dicer Cleaves Triplet Repeat Hairpins into Shorter Repeats that Silence Specific Targets" *Molecular Cell* 25:575-586 (2007).
Lugenbeel et al. "Intragenic Loss of Function Mutations Demonstrate the Primary Role of FMR1 in Fragile X Syndrome" *Nature Genetics* 10:483-485 (1995).
Margolis et al. "Huntington's Disease-Like 2 (HDL2) in North America and Japan" *Ann Neurol* 56:670-674 (2004).
Martens et al. "The Profile of Repeat-Associated Histone Lysine Methylation States in the Mouse Epigenome" *The EMBO Journal* 24:800-812 (2005).
Meijer et al. "A Deletion of 1.6 kb Proximal to the CGG Repeat of the FMR1 Gene Causes the Clinical Phenotype of the Fragile X Syndrome" *Human Molecular Genetics* 3(4):615-620 (1994).
Meyer et al. "A Weak TATA Box is a Prerequisite for Glucocorticoid-Dependent Repression of the Osteocalcin Gene" *The Journal of Biological Chemistry* 272(49):30709-30714 (1997).
Moseley et al. "Bidirectional Expression of CUG and CAG Expansion Transcripts and Intranuclear Polyglutamine Inclusions in Spinocerebellar Ataxia Type 8" *Nature Genetics* 38(7):758-769 (2006).
Napierala et al. "Facile FMR1 mRNA Structure Regulation by Interruptions in CGG Repeats" *Nucleic Acids Research* 33(2):451-463 (2005).
Nelson et al. "Protocol for the Fast Chromatin Immunoprecipitation (ChIP) Method" *Nature Protocols* 1(1):179-185 (2006).
O'Donnell et al. "A Decade of Molecular Studies of Fragile X Syndrome" *Annu. Rev. Neurosci*. 25:315-338 (2002).
Oostra et al. "A Fragile Balance: FMR1 Expression Levels" *Human Molecular Genetics* 12(2):R249-R257 (2003).
Ranum et al. "RNA-Mediated Neuromuscular Disorders" *Annu. Rev. Neurosci*. 29:259-277 (2006).
Reyniers et al. "Severe Mental Retardation and Macroorchidism Without Mutuation in the FMR1 Gene" *American Journal of Medical Genetics* 68:408-412 (1996).
Saluto et al. "An Enhanced Polymerase Chain Reaction Assay to Detect Pre- and Full Mutation Alleles of the *Fragile X Mental Retardation 1* Gene" *Journal of Molecular Diagnostics* 7(5):605-612 (2005).
Sofola et al. "Argonaute-2-Dependent Rescue of a Drosophila Model of FXTAS by FRAXE Premutation Repeat" *Human Molecular Genetics* 16(19):2326-2332 (2007).
Stoger et al. "Epigenetic Variation Illustrated by DNA Methylation Patterns of the Fragile-X Gene *FMR1*" *Human Molecular Genetics* 6(11):1791-1801 (1997).
Talbert et al. "Spreading of Silent Chromatin: Inaction at a Distance" *Nat. Rev. Genet*. 7:793-803 (2006).
Tapscott "Deconstructing Myotonic Dystrophy" *Science Magazine* 289(5485):1701-1702 (2000).
Tassone et al. "FMR1 RNA Within the intranuclear Inclusions of Fragile X-Associated Tremor/Ataxia Syndrome (FXTAS)" *RNA Biology* 1(2):103-105 (2004).
Tassone et al. "Elevated Levels of *FMR1* mRNA in Carrier Males: A New Mechanism of Involvement in the Fragile-X Syndrome" *Am. J. Hum. Genet*. 66:6-15 (2000).
Tassone et al. "Intranuclear Inclusions in Neural Cells with Premutation Alleles in Fragile X Associated Tremor/Ataxia Syndrome" *J Med Genet* 41e43 (2004).
Tassone et al. "Elevated *FMR1* mRNA in Premutation Carriers is Due to Increased Transcription" *RNA* 13:555-562 (2007).
Willemsen et al. "FXTAS: A Progressive Neurologic Syndrome Associated with Fragile X Premutation" *Current Neurology and Neuroscience Reports* 5:405-410 (2005).
Zoghbi et al. "Glutamine Repeats and Neurodegeneration" *Annu. Rev. Neurosci*. 23:217-247 (2000).

\* cited by examiner

ASFMR1 Polyproline ORF can be translated both *in vitro* and *in vivo*.

METHODS AND COMPOSITIONS FOR IDENTIFYING INCREASED RISK OF DEVELOPING FRAGILE X-ASSOCIATED DISORDERS

STATEMENT OF PRIORITY

This application is a 35 U.S.C. §371 national phase application of International Application Ser. No. PCT/US2008/011406, filed Oct. 2, 2008, which claims the benefit, under 35 U.S.C. §119(e), of U.S. Provisional Application No. 60/976,926, filed Oct. 2, 2007, the entire contents of each of which are incorporated herein in their entireties.

GOVERNMENT SUPPORT

Aspects of the present invention were made with the support of federal grant number P30 HD002274-35SI from the National Institute of Child Health and Human Development (NICHD) of the National Institutes of Health (NIH), federal grant number R01 CA068360 from the National Cancer Institute (NCI) of the NIH, NIH Chromosome Metabolism and Cancer Training grant number T32 CA09657-14 and federal grant number F32 AR052581 of the National Institute of Arthritis and Musculoskeletal and Skin Diseases (NIAMS) of the NIH. The United States Government has certain rights to this invention.

FIELD OF THE INVENTION

The present invention provides methods and compositions directed to identification of genetic markers associated with fragile X disorders.

BACKGROUND OF THE INVENTION

The CGG repeat expansion in the 5'-UTR of the fragile X mental retardation gene (FMR1) has been implicated in the pathogenesis of two distinct disorders, fragile X syndrome (FXS), a neurodevelopmental disorder (1, 2), and fragile X-associated tremor and ataxia syndrome (FXTAS), a progressive neurodegenerative disease (3, 4). In the general population, the FMR1 5'-UTR contains 5 to 54 CGG repeats, while expansions of this trinucleotide repeat outside of the normal range fall into two distinct categories, the premutation range with 55 to 200 repeats and the full mutation range with greater than 200 and up to thousands of repeats (3, 5).

Full mutation expansions coupled with cytosine methylation result in transcriptional silencing of the FMR1 gene, loss of expression of FMR1 protein (FMRP), and FXS, the most common form of heritable X-linked mental retardation. The FXS phenotype is complex and highly variable, with mental impairment ranging from mild learning disabilities and emotional problems to severe mental retardation (1, 2). The severity of mental retardation is correlated with the degree of cytosine methylation of the FMR1 promoter and repeat region (6, 7).

Premutation alleles are associated with FXTAS, one of the most common single-gene forms of gait ataxia and tremor in older males (3, 4, 8, 9). While the full mutation alleles are transcriptionally silent, premutation alleles demonstrate a 2-10 fold increase in FMR1 mRNA levels (10) but normal or reduced amounts of FMRP(11-13). Since FXTAS is restricted to premutation carriers and not found in full mutation individuals, increased FMR1 transcript level rather than the reduced FMRP is thought to be the underlying cause of this disorder. Accordingly, post-mortem examination of the brains of FXTAS individuals revealed intranuclear inclusions containing the FMR1 transcript, ubiquitin, molecular chaperones, and components of the proteasome (14, 15). The current molecular model for FXTAS is that the transcript containing the expanded premutation size CGG repeat sequesters results in misfolding of cellular proteins, such as CGG-binding proteins, leading to the formation of intranuclear inclusions (16, 17). This model is consistent with the RNA gain-of-function model proposed for another trinucleotide-repeat associated disease, myotonic dystrophy (DM1), in which the CUG repeat in the 3'-UTR of DMPK sequesters RNA-binding proteins, such as the members of the muscleblind family (18, 19).

Although deregulation or mutations of FMR1 have been implicated in the pathogenesis of both FXS and FXTAS (1, 3, 20, 21), it is important to note that there have been individuals with phenotypic manifestation of FXS with no mutations found in the FMR1 gene (22, 23). In addition, only one-third of male premutation carriers develop FXTAS (9). These observations together with the wide variability of FXS and FXTAS phenotypes suggest that in addition to FMR1, there are other genes potentially involved in pathogenesis of these disorders.

The present invention provides the identification of a gene, ASFMR1, overlapping the CGG repeat region of the FMR1 gene in the antisense orientation. The ASFMR1 transcript is spliced, polyadenylated and exported to the cytoplasm. Similar to FMR1, the ASFMR1 transcript is elevated in lymphoblastoid cells and peripheral blood leukocytes of individuals with premutation alleles relative to normal and is not expressed from full mutation alleles. In addition, the ASFMR1 transcript exhibits premutation-specific alternative splicing, providing a qualitative molecular abnormality associated with FXTAS.

The present invention overcomes previous shortcomings in the art by providing methods and compositions for identifying subjects at increased risk of developing fragile X-associated tremor and ataxia syndrome (FXTAS) and identifying subjects at increased risk of developing fragile X syndrome (FXS).

SUMMARY OF THE INVENTION

In one aspect, the present invention provides an isolated nucleic acid comprising a nucleotide sequence selected from the group consisting of: a) the nucleotide sequence having GenBank® Accession No. EU48200 (human ASFMR1d mRNA) (SEQ ID NO:1); b) the nucleotide sequence having GenBank® Accession No. EU48201 (human ASFMR1c mRNA) (SEQ ID NO:2); c) the nucleotide sequence having GenBank® Accession No. EU48202 (human ASFMR1b mRNA) (SEQ ID NO:3); d) the nucleotide sequence having GenBank® Accession No. EU48203 (human ASFMR1a mRNA) (SEQ ID NO:4); e) the nucleotide sequence having GenBank® Accession No. EU48204 (human ASFMR1e mRNA) (SEQ ID NO:5); and f) a nucleotide sequence that is at least 95% identical to the nucleotide sequence of (a)-(e) above and encodes an mRNA.

In further aspects of this invention, an isolated human ASFMR1 ORF polypeptide is provided, comprising the amino acid sequence as shown in FIG. 9 (SEQ ID NO:6).

The present invention additionally provides a method of identifying a human subject as having a premutation allele in the FMR1 gene of the subject, comprising: a) measuring the amount of a messenger RNA (mRNA) transcript in a sample from the subject, wherein the mRNA transcript is selected from the group consisting of: 1) human ASFMR1d mRNA; 2)

human ASFMR1c mRNA; 3) human ASFMR1b mRNA; 4) human ASFMR1a mRNA; and 5) any combination of (1)-(4) above; and b) comparing the amount of the mRNA transcript(s) measured in step (a) with the amount of the same mRNA transcript(s) measured in a control subject, wherein an increase in the amount of mRNA transcript(s) of step (a) as compared to the amount of the mRNA transcript(s) of the control subject identifies the subject as having a premutation allele in the FMR1 gene.

Furthermore, the present invention provides a method of identifying a human subject as having an increased risk of developing fragile X-associated tremor and ataxia syndrome (FXTAS), comprising: a) measuring the amount of a messenger RNA (mRNA) transcript in a sample from the subject, wherein the mRNA transcript is selected from the group consisting of: 1) human ASFMR1d mRNA; 2) human ASFMR1c mRNA; 3) human ASFMR1b mRNA; 4) human ASFMR1a mRNA; and 5) any combination of (1)-(4) above; and b) comparing the amount of the mRNA transcript(s) measured in step (a) with the amount of the same mRNA transcript(s) measured in a control subject, wherein an increase in the amount of mRNA transcript(s) of step (a) as compared to the amount of the mRNA transcript(s) of the control subject identifies the subject as having an increased risk of developing fragile X-associated tremor and ataxia syndrome (FXTAS).

In other aspects, the present invention provides a method of identifying a human subject as having a full mutation allele in the FMR1 gene of the subject, comprising assaying a sample from the subject for the presence of a messenger RNA (mRNA) transcript selected from the group consisting of 1) human ASFMR1d mRNA; 2) human ASFMR1c mRNA; 3) human ASFMR1b mRNA; 4) human ASFMR1a mRNA; and 5) any combination of (1)-(4) above, wherein the absence of a detectable amount of the mRNA transcript(s) of step (a) above identifies the subject as having a full mutation allele in the FMR1 gene.

Additionally provided herein is a method of identifying a human subject as having an increased risk of developing fragile X syndrome (FXS), comprising assaying a sample from the subject for the presence of a messenger RNA (mRNA) transcript selected from the group consisting of: 1) human ASFMR1d mRNA; 2) human ASFMR1c mRNA; 3) human ASFMR1b mRNA; 4) human ASFMR1a mRNA; and 5) any combination of (1)-(4) above, wherein the absence of a detectable amount of the mRNA transcript(s) of step (a) above identifies the subject as having an increased risk of developing fragile X syndrome.

A method is also provided herein, of identifying a human subject having a premutation allele in the FMR1 gene of the subject, comprising assaying a sample from the subject for the presence of an ASFMR1e (GenBank® Accession No. EU48204) mRNA transcript, wherein the presence of the ASFMR1e mRNA transcript identifies the subject as having a premutation allele in the FMR1 gene.

Also provided herein is a method of identifying a human subject as having an increased risk of developing FXTAS, comprising assaying a sample from the subject for the presence of a FMR1e (GenBank® Accession No. EU48204) mRNA transcript, wherein the presence of the FMR1e mRNA transcript identifies the subject as having an increased risk of developing FXTAS.

In further embodiments of this invention, an antibody is provided, which can be polyclonal or monoclonal, that specifically binds the ASFMR1 polypeptide of this invention. The antibody of this invention can be in a composition with a pharmaceutically acceptable carrier and in some embodiments can further comprise an adjuvant and/or immunostimulatory agent.

The present invention additionally provides a method of treating FXTAS and/or inhibiting or otherwise modulating activity of an ASFMR1 polypeptide in a human subject in a human subject, comprising administering to the subject an effective amount of an antibody of this invention. The antibody of these methods can be in a composition with a pharmaceutically acceptable carrier and in some embodiments can further comprise an adjuvant and/or immunostimulatory agent.

In addition, the present invention provides an isolated nucleic acid encoding an intrabody that specifically binds the ASFMR1 polypeptide of this invention, as well as a vector comprising the nucleic acid.

Methods are also provided herein of treating FXTAS in a human subject and/or inhibiting activity of an ASFMR1 polypeptide in a human subject, comprising delivering to a cell of the subject an effective amount of the nucleic acid and/or vector of this invention.

In yet further embodiments, the present invention provides a method of eliciting an immune response to an ASFMR1 polypeptide, comprising administering to a subject an effective amount of an ASFMR1 polypeptide or an immunogenic fragment thereof. This method can further comprise administering to the subject an adjuvant and/or immunostimulatory agent.

Also provided herein is a method of treating FXTAS in a human subject, comprising administering to the subject an effective amount of an ASFMR1 polypeptide or an immunogenic fragment thereof. This method can further comprise administering to the subject an adjuvant and/or immunostimulatory agent.

Additional embodiments of this invention include a method of identifying a human subject as having a premutation allele in the FMR1 gene of the subject, comprising: a) measuring the amount of ASFMR1 polypeptide in the subject; and b) comparing the amount of ASFMR1 polypeptide measured in step (a) with the amount of ASFMR1 polypeptide measured in a control subject, wherein an increase in the amount of ASFMR1 polypeptide of step (a) as compared to the amount of ASFMR1 polypeptide of the control subject identifies the subject as having a premutation allele in the FMR1 gene.

Further provided is a method of identifying a human subject as having an increased risk of developing fragile X-associated tremor and ataxia syndrome (FXTAS), comprising: a) measuring the amount of ASFMR1 polypeptide in a sample from the subject; and b) comparing the amount of ASFMR1 polypeptide measured in step (a) with the amount of ASFMR1 polypeptide measured in a control subject, wherein an increase in the amount of ASFMR1 polypeptide of step (a) as compared to the amount of ASFMR1 polypeptide of the control subject identifies the subject as having an increased risk of developing fragile X-associated tremor and ataxia syndrome (FXTAS).

The present invention further provides a method of identifying a human subject as having a full mutation allele in the FMR1 gene of the subject, comprising assaying a sample from the subject for ASFMR1 polypeptide, wherein the absence of a detectable amount of ASFMR1 polypeptide identifies the subject as having a full mutation allele in the FMR1 gene.

Additionally provided is a method of identifying a human subject as having an increased risk of developing fragile X syndrome (FXS), comprising assaying a sample from the subject for ASFMR1 polypeptide, wherein the absence of a detectable amount of ASFMR1 polypeptide identifies the subject as having an increased risk of developing fragile X syndrome.

In further embodiments, the present invention provides a method of diagnosing a human subject as having fragile X-associated tremor and ataxia syndrome (FXTAS), comprising: a) measuring the amount of a messenger RNA (mRNA) transcript in a sample from the subject, wherein the mRNA transcript is selected from the group consisting of: 1) human ASFMR1d mRNA; 2) human ASFMR1c mRNA; 3) human ASFMR1b mRNA; 4) human ASFMR1a mRNA; and 5) any combination of (1)-(4) above; and b) comparing the amount of the mRNA transcript(s) measured in step (a) with the amount of the same mRNA transcript(s) measured in a control subject, wherein an increase in the amount of mRNA transcript(s) of step (a) as compared to the amount of the mRNA transcript(s) of the control subject provides a diagnosis of the subject as having fragile X-associated tremor and ataxia syndrome (FXTAS).

A method is also provide herein of diagnosing a human subject as having fragile X-associated tremor and ataxia syndrome (FXTAS), comprising: a) measuring the amount of ASFMR1 polypeptide in a sample from the subject; and b) comparing the amount of ASFMR1 polypeptide measured in step (a) with the amount of ASFMR1 polypeptide measured in a control subject, wherein an increase in the amount of ASFMR1 polypeptide of step (a) as compared to the amount of ASFMR1 polypeptide of the control subject provides a diagnosis of the subject as having fragile X-associated tremor and ataxia syndrome (FXTAS).

Furthermore, the present invention provides a method of diagnosing a human subject as having fragile X syndrome (FXS), comprising assaying a sample from the subject for a messenger RNA (mRNA) transcript selected from the group consisting of: 1) human ASFMR1d mRNA; 2) human ASFMR1c mRNA; 3) human ASFMR1b mRNA; 4) human ASFMR1a mRNA; and 5) any combination of (1)-(4) above, wherein the absence of a detectable amount of the mRNA transcript(s) of step (a) above provides a diagnosis of the subject as having fragile X syndrome.

Additionally provided herein is a method of diagnosing a human subject as having fragile X syndrome (FXS), comprising assaying a sample from the subject for ASFMR1 polypeptide, wherein the absence of a detectable amount of ASFMR1 polypeptide provides a diagnosis of the subject as having fragile X syndrome.

DETAILED DESCRIPTION OF THE INVENTION

Figure 1:
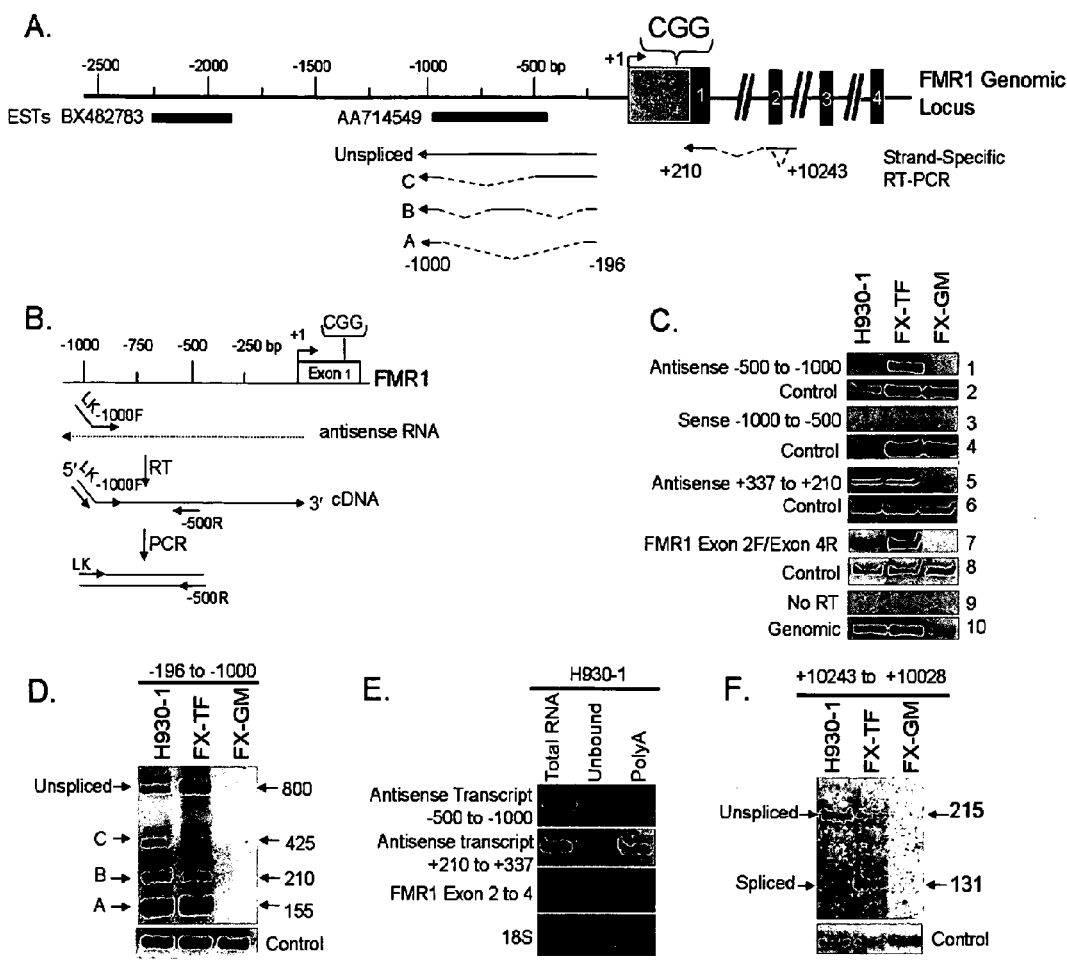
FIGS. 1A-E. Identification of a polyadenylated and spliced antisense transcript at the FMR1 locus. (A) Diagram of the FMR1 locus. Exons 1 to 4 of FMR1 are indicated by rectangles, shaded black for coding regions and gray for the 5'-UTR, with the CGG repeat region noted. Direction of transcription is indicated with an arrow. Thick horizontal bars and corresponding accession numbers indicate the location of reported ESTs. The antisense RNA transcript, including multiple splice forms, is indicated by arrows in the opposite orientation of FMR1. Characterized splice sites are indicated by dotted lines. Nucleotide numbering is relative to the FMR1 major transcription initiation site according to the published sequence (26). (B) Diagram of the strand-specific RT-PCR method. To identify cDNA generated from a particular strand, a linker sequence is attached to a gene-specific primer. The linker sequence is used as a primer for subsequent PCR amplification. (C) Strand-specific RT-PCR analysis of human lymphoblastoid cell lines identified an antisense transcript at the position −500 to −1000 bp upstream of FMR1 and at the position +337 to +210 bp overlapping exon 1 of FMR1 in normal, H930-1, and premutation, FX-TF, cells, but not in full mutation, FX-GM, cells (panels 1 and 5). No sense transcript was detected upstream of FMR1 (panel 3). Panels 9 and 10 represent no RT and genomic DNA controls, respectively. The quality of cDNA synthesis was verified by amplification of the control transcript, CTCF, panels 2, 4, 6 and 8. (D) Identification of alternative spice forms of the antisense transcript using PCR primers to −1000 and −196 relative to FMR1. PCR product size is indicated. Spliced forms A, B, and C and unspliced transcript, D, are depicted in (a). (E) Strand-specific RT-PCR analysis of the oligo-dT bound and unbound fractions of total RNA demonstrated that, similar to FMR1, the antisense transcript at −500 to −1000 and +337 to +210 is enriched in polyA fraction. 18S transcript was used as a non-polyadenylated control. (F) Strand-specific RT-PCR with primers to +10028 and +10243 relative to FMR1 identified an alternative splice form of the antisense transcript in premutation cells, FX-TF, but not in normal cells, H930-1. No expression of the transcript was detected in the full mutation cells, FX-GM.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "consists essentially of" (and grammatical variants) means that the immunogenic composition comprises no other material immunogenic agent other than the indicated agents. The term "consists essentially of" does not exclude the presence of other components such as adjuvants, immunomodulators, and the like.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

The present invention is based on the unexpected discovery of an antisense gene, ASFMR1, which overlaps the CGG repeat region of FMR1. ASFMR1 was found to be upregulated in subjects with premutation alleles and was also found not to be expressed at detectable levels in subjects with full mutation alleles. The inventors have also discovered that ASFMR1 exhibits premutation-specific alternative splicing. Through analysis of the expression pattern of ASFMR1 in various subjects (i.e., measurement/detection of ASFMR1 mRNA transcripts), the methods of the present invention have been developed.

Thus, in one embodiment, the present invention provides an isolated nucleic acid comprising, consisting essentially of and/or consisting of a nucleotide sequence that can be: a) the nucleotide sequence having GenBank® Accession No. EU48200 (human ASFMR1d mRNA); b) the nucleotide sequence having GenBank® Accession No. EU48201 (human ASFMR1c mRNA); c) the nucleotide sequence having GenBank® Accession No. EU48202 (human ASFMRb mRNA); d) the nucleotide sequence having GenBank® Accession No. EU48203 (human ASFMR1a mRNA); e) the nucleotide sequence having GenBank® Accession No. EU48204 (human ASFMR1e mRNA); and f) a nucleotide sequence that is at least 50%, 60%, 65%, 70%, 75%, 80%, 85%, 90%, 92%, 93%, 94%, 95% 96%, 96%, 98% or 99% identical to the nucleotide sequence of (a)-(e) above and encodes an mRNA of this invention.

Figure 9:
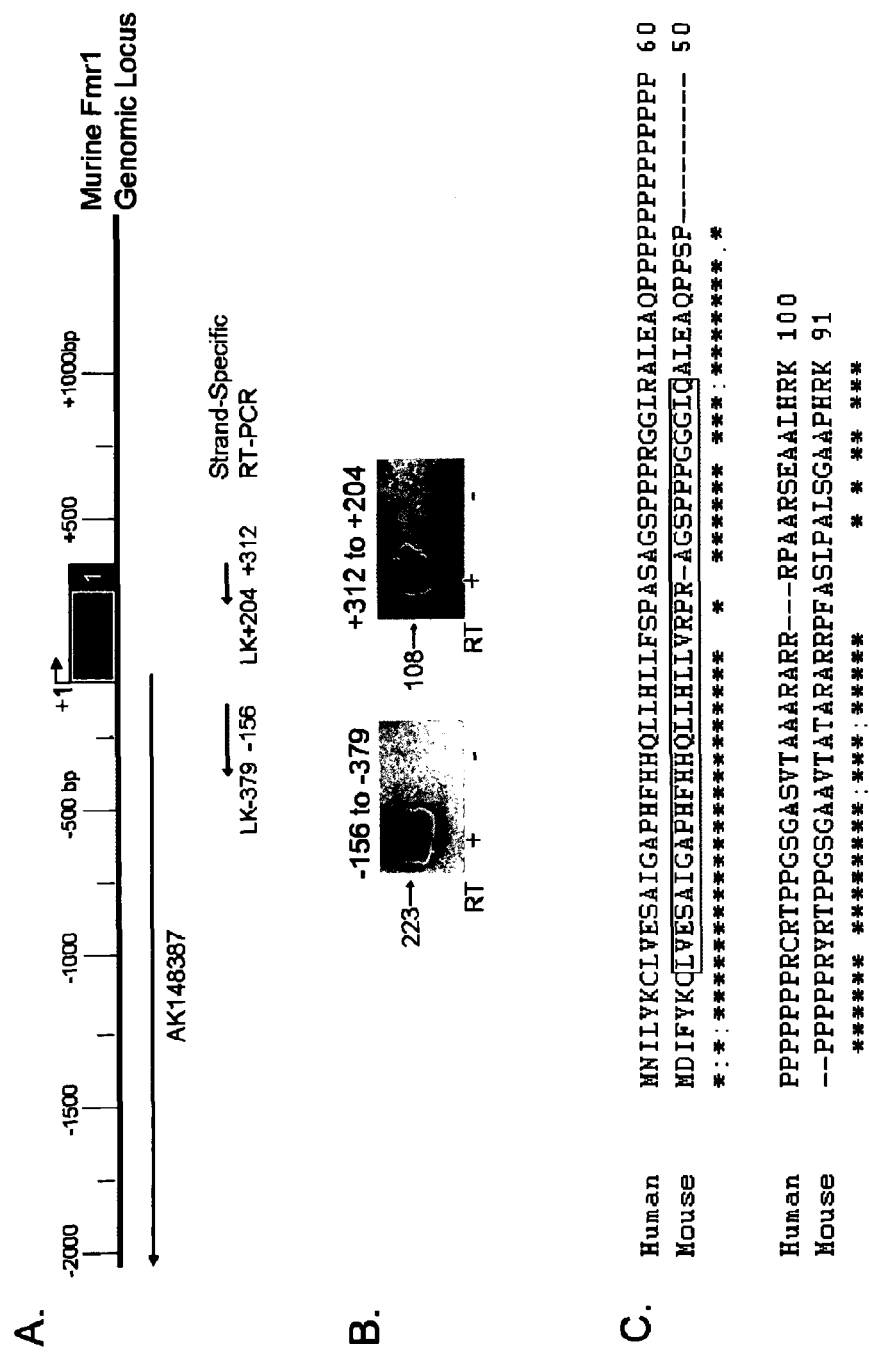
FIGS. 9A-C. Detection of the murine Asfmr1 transcript. (A) A horizontal black line, with exon 1 indicated by a rectangle depicts the murine Fmr1 genomic locus. An arrow and +1 denote the transcriptional start site as indicated the in GenBank® database. The scale is indicated numerically. The previously reported murine transcript, AK148387, is indicated by a horizontal arrow in the opposite orientation as murine Fmr1. The location of strand-specific RT-PCR products are depicted by short, horizontal arrows, with the primers used for analysis indicated by numeric value. (B) The strand-specific RT-PCR analysis of mouse embryonic fibroblasts with primer sets LK−156/−379, and LK+312/+204 identified two regions of antisense transcription at the murine Fmr1 locus: the −156 to −379 region that corresponds to the location of the AK148387 transcript and the +312 to +204 region that overlaps first exon of Fmr1. This suggests that similar to the human FMR1 locus, there is an antisense transcript Asfmr1 spanning the CGG-rich region of murine Fmr1. (C) Alignment of the human ASFMR1 ORF (SEQ ID NO:6) and predicted murine Asfmr1 ORF using the Clustalw program shows that, similar to ASFMR1, Asfmr1 contains a potential proline-rich ORF, conserved between human and mouse. The murine amino acid sequence (SEQ ID NO:21) shown in the black box corresponds to the sequence identified by strand-specific RT-PCR.

Furthermore the present invention provides an isolated human ASFMR1 ORF polypeptide, comprising, consisting essentially of and/or consisting of the amino acid sequence as shown in FIG. 9. Also provided herein are fragments (e.g., biologically active fragments) of the polypeptides of this invention.

As used herein, the term "polypeptide" or "protein" is used to describe a chain of amino acids that correspond to those encoded by a nucleic acid. A polypeptide or protein of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences of this invention are presented in the amino to carboxy direction, from left to right. Nucleotide sequences are presented herein, in the 5' to 3' direction, from left to right. The nucleic acids of this invention can be either single or double stranded (i.e., including the complementary nucleic acid). A nucleic acid of this invention can be the complement of a nucleic acid described herein.

A "biologically active fragment" includes a polypeptide of this invention that comprises a sufficient number of amino acids to have one or more of the biological activities of the polypeptides of this invention. Such biological activities can include, but are not limited to, in any combination, binding activity and/or immunogenic activity, as well as any other activity now known or later identified for the polypeptides and/or fragments of this invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention (e.g., immunogenicity) according to the methods described herein, which are routine methods for testing activities of polypeptides, and/or according to any art-known and routine methods for identifying such activities. Such production and testing to identify biologically active fragments and/or immunogenic fragments of the polypeptides described herein would be well within the scope of one of ordinary skill in the art and would be routine.

In certain embodiments, the fragments and/or polypeptides of this invention can be fused with a "carrier" protein or peptide to produce a fusion protein. For example, the carrier protein or peptide can be fused to a polypeptide and/or fragment of this invention to increase the stability thereof (e.g., decrease the turnover rate) in a cell and/or subject of this invention. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., green fluorescent protein (GFP), β-glucoronidase, β-galactosidase, luciferase, and the like) for easy detection. As a further alternative, the fusion protein attached to the polypeptides and/or fragments and a carrier protein or peptide can be targeted to a subcellular compartment of interest, i.e., to affect the co-localization of the polypeptide and/or fragment. Any suitable carrier protein as is well known in the art can be used to produce a fusion protein of this invention.

As used herein, "nucleic acid" and "nucleotide sequence" and "polynucleotide: encompass both RNA and DNA, including cDNA, genomic DNA, mRNA, synthetic (e.g., chemically synthesized) DNA and chimeras of RNA and DNA. The term polynucleotide or nucleotide sequence refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

An "isolated nucleic acid" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used therapeutically.

An isolated cell refers to a cell that is separated from other components with which it is normally associated in its natural state. For example, an isolated cell can be a cell in culture medium and/or a cell in a pharmaceutically acceptable carrier of this invention.

The term "oligonucleotide" refers to a nucleic acid sequence of at least about five nucleotides to about 100 nucleotides, for example, about 12 to 18, about 15 to 30 nucleotides, or about 20 to 25 nucleotides, which can be used, for example, as a primer in a PCR amplification and/or as a probe in a hybridization assay or in a microarray. Oligonucleotides can be natural or synthetic, e.g., DNA, RNA, modified backbones, etc. Peptide nucleic acids (PNAs) can also be used as probes in the methods of this invention.

The present invention further provides fragments or oligonucleotides of the nucleic acids of this invention, which can be used, for example as primers or probes and as antisense sequences. Thus, in some embodiments, the present invention provides a fragment or oligonucleotide, which is a nucleotide sequence that comprises, consists essentially of and/or consists of at least, for example, 5, 10, 15, 20, 25, 30, 35, 40, 45, 50, 55, 60, 65, 70, 75, 80, 85, 90, 95, 100, 110, 120, 125, 135, 150, 160, 170, 175, 200, 225, 250, 275, 300, 325, 350, 375, 400, 425, 450, 475 or 500 contiguous nucleotides of a nucleic acid of this invention (e.g., the sequences identified here as having GenBank® Accession Nos. EU48200 (SEQ ID NO:1), EU48201 (SEQ ID NO:2), EU48202 (SEQ ID NO:3), EU48203 (SEQ ID NO:4) and EU48204 (SEQ ID NO:5), respectively. Such fragments or oligonucleotides can be detectably labeled or modified, for example, to include and/or incorporate a restriction enzyme cleavage site when employed as a primer in an amplification (e.g., PCR) assay.

The present invention further includes isolated polypeptides, peptides, proteins and/or fragments that are substantially equivalent to those described for this invention. As used herein, "substantially equivalent" can refer both to nucleic acid and amino acid sequences, for example a mutant sequence, that varies from a reference sequence by one or more substitutions (e.g., substitution with conservative amino acids as are well known in the art), deletions and/or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologues, as well as methods of obtaining homologues, of the polypeptides and/or fragments of this invention from other species. As used herein, an amino acid sequence or protein is defined as a homologue of a polypeptide or fragment of the present invention if it shares significant homology to one of the polypeptides and/or fragments of the present invention. Significant homology means at least 50%, 55%, 60%, 65%, 70%, 75%, 80%, 85%, 90%, 95%, 98% and/or 100% homology with another amino acid sequence. Specifically, by using the nucleic acids that encode the proteins and fragments of this invention, as a probe or primer, and techniques such as PCR amplification and colony/plaque hybridization, one skilled in the art can identify homologues of the polypeptides and/or fragments of this invention in other organisms.

"Substantial homology or similarity" means that a nucleic acid or fragment thereof is "substantially homologous" (or "substantially similar") to another if, when optimally aligned (with appropriate nucleotide insertions or deletions) with the other nucleic acid (or its complementary strand), using, e.g., the BLASTN alignment program, there is nucleotide sequence identity in at least about 60% of the nucleotide bases, usually in at least about 70%, more usually in at least about 80%, in at least about 90%, or in at least about 95-98% of the nucleotide bases. To determine homology between two different nucleic acids, the percent homology can be determined using the BLASTN program "BLAST 2 sequences." This program is available for public use from the National Center for Biotechnology Information (NCBI) over the internet (Altschul et al., 1997). The parameters to be used are whatever combination of the following yields the highest calculated percent homology (as calculated below) with the default parameters shown in parentheses: Program--blastn Matrix--0 BLOSUM62 Reward for a match--0 or 1 (1) Penalty for a mismatch--0, −1, −2 or −3 (−2) Open gap penalty-- 0, 1, 2, 3, 4 or 5 (5) Extension gap penalty--0 or 1 (1) Gap x_dropoff--0 or 50 (50) Expect—10.

The terms "substantial homology" or "substantial identity", when referring to polypeptides, indicate that the polypeptide or protein in question exhibits at least about 30% identity using the BLASTP program with an entire naturally-occurring protein or a portion thereof, usually at least about 70% identity over the common lengths, more usually at least about 80% identity, at least about 90% identity, or at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

In additional embodiments, the present invention further provides a method of identifying a human subject as having a premutation allele in the FMR1 gene of the subject, comprising: a) measuring the amount of a messenger RNA (mRNA) transcript in a sample from the subject, wherein the mRNA transcript is selected from the group consisting of:1) human ASFMR1d mRNA (SEQ ID NO:1); 2) human ASFMR1c mRNA (SEQ ID NO:2); 3) human ASFMR1b mRNA (SEQ ID NO:3); 4) human ASFMR1a mRNA (SEQ ID NO:4); and 5) any combination of (1)-(4) above; and b) comparing the amount of the mRNA transcript(s) measured in step (a) with the amount of the same mRNA transcript(s) measured in a control subject, wherein an increase in the amount of mRNA transcript(s) of step (a) as compared to the amount of the mRNA transcript(s) of the control subject identifies the subject as having a premutation allele in the FMR1 gene.

Furthermore, the present invention provides a method of identifying a human subject as having an increased risk of developing fragile X-associated tremor and ataxia syndrome (FXTAS), comprising: a) measuring the amount of a messenger RNA (mRNA) transcript in a sample from the subject, wherein the mRNA transcript is selected from the group consisting of: 1) human ASFMR1d mRNA (SEQ ID NO:1); 2) human ASFMR1c mRNA (SEQ ID NO:2); 3) human ASFMR1b mRNA (SEQ ID NO:3); 4) human ASFMR1a mRNA (SEQ ID NO:4); and 5) any combination of (1)-(4) above; and b) comparing the amount of the mRNA transcript(s) measured in step (a) with the amount of the same mRNA transcript(s) measured in a control subject, wherein an increase in the amount of mRNA transcript(s) of step (a) as compared to the amount of the mRNA transcript(s) of the control subject identifies the subject as having an increased risk of developing fragile X-associated tremor and ataxia syndrome (FXTAS).

In other aspects, the present invention provides a method of identifying a human subject as having a full mutation allele in the FMR1 gene of the subject, comprising assaying a sample from the subject for the presence of a messenger RNA (mRNA) transcript selected from the group consisting of 1) human ASFMR1d mRNA (SEQ ID NO:1); 2) human ASFMR1c mRNA (SEQ ID NO:2); 3) human ASFMR1b mRNA (SEQ ID NO:3); 4) human ASFMR1a mRNA (SEQ ID NO:4); and 5) any combination of (1)-(4) above, wherein the absence of a detectable amount of the mRNA transcript(s) of step (a) above identifies the subject as having a full mutation allele in the FMR1 gene.

Additionally provided herein is a method of identifying a human subject as having an increased risk of developing fragile X syndrome (FXS), comprising assaying a sample from the subject for the presence of a messenger RNA (mRNA) transcript selected from the group consisting of: 1) human ASFMR1d mRNA (SEQ ID NO:1); 2) human ASFMR1c mRNA (SEQ ID NO:2); 3) human ASFMR1b mRNA (SEQ ID NO:3); 4) human ASFMR1a mRNA (SEQ ID NO:4); and 5) any combination of (1)-(4) above, wherein the absence of a detectable amount of the mRNA transcript(s) of step (a) above identifies the subject as having an increased risk of developing fragile X syndrome.

A method is also provided herein, of identifying a human subject having a premutation allele in the FMR1 gene of the subject, comprising assaying a sample from the subject for the presence of a FMR1e (GenBank® Accession No. EU48204) mRNA transcript (SEQ ID NO:5), wherein the presence of the FMR1e mRNA transcript identifies the subject as having a premutation allele in the FMR1 gene.

Also provided herein is a method of identifying a human subject as having an increased risk of developing FXTAS, comprising assaying a sample from the subject for the presence of a FMR1 e (GenBank® Accession No. EU48204) mRNA transcript (SEQ ID NO:5), wherein the presence of the FMR1e mRNA transcript identifies the subject as having an increased risk of developing FXTAS.

Additional embodiments of this invention include a method of identifying a human subject as having a premutation allele in the FMR1 gene of the subject, comprising: a) measuring the amount of ASFMR1 polypeptide in the subject; and b) comparing the amount of ASFMR1 polypeptide measured in step (a) with the amount of ASFMR1 polypeptide measured in a control subject, wherein an increase in the amount of ASFMR1 polypeptide of step (a) as compared to the amount of ASFMR1 polypeptide of the control subject identifies the subject as having a premutation allele in the FMR1 gene.

Further provided is a method of identifying a human subject as having an increased risk of developing fragile X-associated tremor and ataxia syndrome (FXTAS), comprising: a) measuring the amount of ASFMR1 polypeptide in a sample from the subject; and b) comparing the amount of ASFMR1 polypeptide measured in step (a) with the amount of ASFMR1 polypeptide measured in a control subject, wherein an increase in the amount of ASFMR1 polypeptide of step (a) as compared to the amount of ASFMR1 polypeptide of the control subject identifies the subject as having an increased risk of developing fragile X-associated tremor and ataxia syndrome (FXTAS).

The present invention further provides a method of identifying a human subject as having a full mutation allele in the FMR1 gene of the subject, comprising assaying a sample from the subject for ASFMR1 polypeptide, wherein the absence of a detectable amount of ASFMR1 polypeptide identifies the subject as having a full mutation allele in the FMR1 gene.

Additionally provided is a method of identifying a human subject as having an increased risk of developing fragile X syndrome (FXS), comprising assaying a sample from the subject for ASFMR1 polypeptide, wherein the absence of a detectable amount of ASFMR1 polypeptide identifies the subject as having an increased risk of developing fragile X syndrome.

In further embodiments, the present invention provides a method of diagnosing a human subject as having fragile X-associated tremor and ataxia syndrome (FXTAS), comprising: a) measuring the amount of a messenger RNA (mRNA) transcript in a sample from the subject, wherein the mRNA transcript is selected from the group consisting of: 1) human ASFMR1d mRNA; 2) human ASFMR1c mRNA; 3) human ASFMR1b mRNA; 4) human ASFMR1a mRNA; and 5) any combination of (1)-(4) above; and b) comparing the amount of the mRNA transcript(s) measured in step (a) with the amount of the same mRNA transcript(s) measured in a control subject, wherein an increase in the amount of mRNA transcript(s) of step (a) as compared to the amount of the mRNA transcript(s) of the control subject provides a diagnosis of the subject as having fragile X-associated tremor and ataxia syndrome (FXTAS).

A method is also provide herein of diagnosing a human subject as having fragile X-associated tremor and ataxia syndrome (FXTAS), comprising: a) measuring the amount of ASFMR1 polypeptide in a sample from the subject; and b) comparing the amount of ASFMR1 polypeptide measured in step (a) with the amount of ASFMR1 polypeptide measured in a control subject, wherein an increase in the amount of ASFMR1 polypeptide of step (a) as compared to the amount of ASFMR1 polypeptide of the control subject provides a diagnosis of the subject as having fragile X-associated tremor and ataxia syndrome (FXTAS).

Furthermore, the present invention provides a method of diagnosing a human subject as having fragile X syndrome (FXS), comprising assaying a sample from the subject for a messenger RNA (mRNA) transcript selected from the group consisting of: 1) human ASFMR1d mRNA; 2) human ASFMR1c mRNA; 3) human ASFMR1b mRNA; 4) human ASFMR1a mRNA; and 5) any combination of (1)-(4) above, wherein the absence of a detectable amount of the mRNA transcript(s) of step (a) above provides a diagnosis of the subject as having fragile X syndrome.

Additionally provided herein is a method of diagnosing a human subject as having fragile X syndrome (FXS), comprising assaying a sample from the subject for ASFMR1 polypeptide, wherein the absence of a detectable amount of ASFMR1 polypeptide provides a diagnosis of the subject as having fragile X syndrome.

Methods of detecting and/or quantitating a protein or polypeptide or peptide in a sample are routine and well known in the art and such methods can be readily carried out by one of ordinary skill in the art to detect and/or quantitate a protein, polypeptide or peptide of this invention.

A "subject" of this invention includes any animal that has a FMR1 gene and/or is susceptible to FXS or FXTAS. Such a subject can be a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species and in particular embodiments, is a human. A subject of this invention can be of any gender, race or ethnic group (e.g., Caucasian, Asian, African American, African, Hispanic, Mideastern, etc.) A "subject in need thereof" is a subject known to be, or suspected of having FXS or FXTAS or at increased risk of developing FXS or FXTAS. A subject of this invention can also include a subject not previously known or suspected to have FXS or FXTAS or in need of treatment for FXS or FXTAS. For example, a subject of this invention can be administered the compositions of this invention even if it is not known or suspected that the subject has FXS or FXTAS (e.g., prophylactically). A subject of this invention is also a subject known to have or believed to be at risk of developing FXS or FXTAS.

As used herein, a "premutation allele" is an allele of the FMR1 gene that comprises CGG trinucleotide repeats in an amount that is greater than the normal range (e.g., about 5 to about 54 CGG repeats) but less than full mutation range (e.g., greater than about 200 CGG repeats. Thus, the premutation allele can comprise about 55 to about 200 CGG repeats in the 5'-UTR of the FMR1 gene. A premutation allele is known in the art to be associated with FXTAS, as described herein.

As also used herein, a "full mutation allele" is an allele of the FMR1 gene that comprises CGG trinucleotide repeats in an amount that is about 200 or greater and can be in the thousands of repeats. A full mutation allele is known in the art to be associated with FXS, as described herein. The severity of mental retardation in a subject with FXS is correlated with the degree of cytosine methylation of the FMR1 promoter and repeat region.

The FMR1 gene is well characterized in various species and nucleic acid and amino acid sequences associated therewith are available in the literature (See, e.g., GenBank® Accession Nos. NM_002024 (human), NM_001085687 and NM_001005454 (*Xenopus* spp.), and NM_008031 (mouse).

The term "genetic marker" as used herein refers to a region of a nucleotide sequence (e.g., in a chromosome) that is subject to variability (i.e., the region can be polymorphic for a variety of alleles). Examples of genetic markers of this invention can include but are not limited to single nucleotide polymorphism alleles, haplotypes (i.e., combinations of alleles), microsatellites, restriction fragment length polymorphisms (RFLPs), repeats (i.e., duplications), insertions, deletions, etc., as are well known in the art.

An "allele" as used herein refers to one of two or more alternative forms of a nucleotide sequence at a given position (locus) on a chromosome. Usually alleles are nucleotide sequences that make up the coding sequence of a gene, but sometimes the term is used to refer to a nucleotide sequence in a non-coding sequence. An individual's genotype for a given gene is the set of alleles it happens to possess.

The term, "genotype" is used herein to mean a specific allele or alleles an individual carries at a given locus. It can also be used to describe a set of alleles for multiple loci.

The term, "phenotype," is used herein to mean the form taken by some character (or group of characters) in a specific individual. It can also mean the detectable outward manifestations of a specific genotype.

In the methods described herein, the detection and/or measurement of a nucleic acid of this invention (e.g., ASFMR1 mRNA transcript) in a subject can be carried out according to methods well known in the art. For example, nucleic acid can be obtained from any suitable sample from the subject that will contain nucleic acid and the nucleic acid can then be prepared and analyzed according to well-established protocols for the presence of specific nucleic acids according to the methods of this invention. In some embodiments, complementary DNA (cDNA) can be produced from RNA using reverse transcription (RT) protocols that are well known in the art. In some embodiments, analysis of the nucleic acid can be carried by amplification of the region of interest according to amplification protocols well known in the art (e.g., polymerase chain reaction (PCR), ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA), etc.). In particular embodiments of the present invention, ASFMR1 mRNA transcripts can be detected and/or measured (i.e., quantified) using various methods such as strand-specific RT-PCR, semi-quantitative RT-PCR, real-time RT-PCR, RNA ligase-mediated rapid amplification of 5'- and 3' cDNA ends (RLM-RACE), Northern blot analysis and/or any other method for detecting and/or quantitating nucleic acid and in particular RNA, according to protocols as described in the Examples section provided herein and as are well known in the art. The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers according to the methods of this invention.

In carrying out the methods of this invention, detection reagents can be developed and used to identify a nucleic acid (e.g., a messenger RNA transcript) of the present invention individually or in combination with the identification of other nucleic acids, and such detection reagents can be readily incorporated into one of the established kit or system formats that are well known in the art. The terms "kits" and "systems," as used herein refer, e.g., to combinations of detection reagents, or one or more detection reagents in combination with one or more other types of elements or components (e.g., other types of biochemical reagents, containers, packages such as packaging intended for commercial sale, substrates to which detection reagents are attached, electronic hardware components, etc.) Accordingly, the present invention further provides nucleic acid detection/identification kits and systems, including but not limited to, packaged probe and primer sets (e.g., TAQMAN probe/primer sets), arrays/microarrays of nucleic acid molecules, and/or beads that contain one or more probes, primers, or other detection reagents for detecting/identifying one or more nucleic acids of the present invention. The kits/systems can optionally include various electronic hardware components; for example, arrays ("DNA chips") and microfluidic systems ("lab-on-a-chip" systems) provided by various manufacturers. Other kits/systems (e.g., probe/primer sets) may not include electronic hardware components, but can be comprised of, for example, one or more detection reagents (along with, optionally, other biochemical reagents) packaged in one or more containers.

In some embodiments, a kit of this invention typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, etc.) necessary to carry out an assay or reaction, such as amplification and/or detection of a nucleic acid molecule of this invention. In some embodiments of the present invention, kits are provided that contain the necessary reagents to carry out one or more assays to detect one or more nucleic acids disclosed herein. In some embodiments of the present invention, allele detection kits/systems can be in the form of nucleic acid arrays, or compartmentalized kits, including microfluidic/lab-on-a-chip systems.

A detection kit/system of the present invention can include components that are used to prepare nucleic acids from a test sample for the subsequent amplification and/or detection of a nucleic acid molecule of this invention, as well as for the detection and/or quantitation of a polypeptide or peptide of this invention. Such sample preparation components can be used to produce, e.g., nucleic acid extracts (including DNA and/or RNA), proteins, protein fractions, cellular fractions and/or membrane extracts from any bodily fluids or materials (such as blood, serum, plasma, urine, saliva, phlegm, sputum, joint fluids, fecal material, secretions, gastric juices, semen, tears, sweat, spinal fluid, etc.), skin, hair, cells (especially nucleated cells), biopsies, washes, lavages, exudates, buccal swabs and/or tissue specimens. The test samples used in the above-described methods will vary based on such factors as the assay format, nature of the detection method, and the specific tissues, cells or extracts used as the test sample to be assayed. Methods of preparing nucleic acids, proteins, and cell extracts are well known in the art and can be readily adapted to obtain a sample that is compatible with the system utilized. Automated sample preparation systems for extracting nucleic acids from a test sample are commercially available (e.g., Qiagen's BIOROBOT 9600, Applied Biosystems' PRISM 6700, and Roche Molecular Systems COBAS AmpliPrep System).

Another form of kit included in the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one detection reagent for detecting one or more nucleic acids of the present invention, one or more containers which contain wash reagents (such as phosphate buffered saline, Tris-buffers, etc.), and one or more containers which contain the reagents used to reveal the presence of the bound nucleic acid or other detection reagents. The kit can optionally further comprise compartments and/or reagents for, for example, nucleic acid amplification or other enzymatic reactions such as primer extension reactions, hybridization, ligation, electrophoresis (e.g., capillary electrophoresis), mass spectrometry, and/or laser-induced fluorescence detection. The kit can also include instructions for using the kit. Exemplary compartmentalized kits include microfluidic devices known in the art (e.g., Weigl et al. (2003) "Lab-on-a-chip for drug development" Adv Drug Deliv Rev. 55(3):349-77). In such microfluidic devices, the containers may be referred to as, for example, microfluidic "compartments," "chambers," or "channels."

The present invention is also directed to methods of treating FXATS and FXS in a subject of this invention. Thus, in further embodiments, the present invention provides a method of treating FXTAS in a human subject, comprising administering to the subject an effective amount of an inhibitor of ASFMR1 transcription or translation. Therapeutic agents targeting sequences in the ASFMR1 transcripts a-d (SEQ ID NOs:1-4) described herein, as well as the premutation specific transcript ASFMR1e (SEQ ID NO:5) by RNA interference (RNAi), include short interfering RNA, short hairpin RNA and micro RNA and any modifications of the above techniques that results in loss of function by rendering the transcript inactive, prevents further transcript processing, inhibits interaction with other RNA or protein partners, results in elimination of excessive transcript levels by altering transcript stability, or prevents protein translation.

Therapeutic agents targeting sequences in the regulatory regions of the ASFMR1 gene include gene-specific proteins or oligoribonucleotides (ORNs) or short RNA or DNA oligonucleotides, such as siRNA or miRNA or their corresponding DNA oligonucleotides that target DNA sequences in the regulatory regions of the ASFMR1 gene to modulate its expression. Nonlimiting examples of such sequence include a fragment of the nucleotide sequences defined herein as SEQ ID NOs:1-5) that comprises, consists essentially of and/or consists of an oligonucleotide of at least five contiguous nucleotides of these sequences or its complementary sequence. For example, such a fragment can be nucleotides 1-10, 5-10, 15-30, 36-42, 60-75, etc. (or the complement of these nucleotide sequences), including any starting and ending nucleotide not specifically recited herein that is a contiguous nucleotide sequence of the nucleotide sequences of SEQ ID NOs: 1-5. Examples of targeting sequences in the regulatory region of the ASFMR1 gene include, but are not limited to, the sequences identified as the putative promoter regions of ASFMR1.

The following is the sequence: −100acttccagttactaataca-caagactctctggtttctttcttcacattcaagggaattaagacgtaaggatcaatac catacaataagggacctccaggacAtt-agcagaaacagtcattccattagtttaatactgagttgttcagaaac+38 (SEQ ID NO:60) for the promoter referred to herein as +10243, relative to FMR1. In this example, the ASFMR1 transcription start site is at +1 (+10243) indicated as a capital A, in bold. Relative to +1, the weak TATAA box is from −30 to −35 and Inr1 is from −8 to −14. Inr2 is from −2 to +5, and Inr3 is from +2 to +7. The DPEs are from +28 to +32 and +31 to +35. (See also FIG. 2D.) Thus, a therapeutic agent of this invention that is a targeting sequence can be, but is not limited to a nucleotide sequence, comprising, consisting essentially of and/or consisting of at least 5, 10, 15, 20, 25 or 30 contiguous nucleotides of the sequence below (or the complement thereof).

For the bi-directional promoter, the following sequence +528gcctgactgaggccgaaccccggc-ccgctgcgggtgtaaacactgaaaccacgtcacgtgatcaacgctg ttccctc-ccccgcgggctcagcccctcggc-cccgccctctCtcttcaagtggcctgggagcgcgcgcatgcgCgct gcTgggaaCcggccggggtgccgggtCgaaagaC +749 (SEQ ID NO:61) includes 110 nt of sequence upstream of the cluster of transcription initiation sites, which are from +640 to +749, relative to ASFMR1 major transcription start site (or −99 to −208, relative to FMR1 as described herein). Multiple transcription start sites at this promoter are indicated by capital letters in bold. (See also FIG. 2C.) Thus, a therapeutic agent of this invention that is a targeting sequence can be, but is not limited to a nucleotide sequence, comprising, consisting essentially of and/or consisting of at least 5, 10, 15, 20, 25 or 30 contiguous nucleotides of the sequence below (or the complement thereof).

Another regulatory region to target is the CGG•CCG repeat region, as it has been predicted to be an enhancer of transcription, which is from +341 to +501 relative to ASFMR1 for the repeat size shown herein. The number range will change for larger or smaller CGG•CCG repeats, as would be known to one of ordinary skill in the art. Thus, a therapeutic agent of this invention that is a targeting sequence can be, but is not limited to a nucleotide sequence, comprising, consisting essentially of and/or consisting of at least 5, 10, 15, 20, 25 or 30 contiguous nucleotides of the CGG•CCG repeat region.

Furthermore, the present invention provides a method of treating FXS in a human subject, comprising administering to the subject an effective amount of a therapeutic agent to reactivate ASFMR1 transcription by reducing deoxycytosine and/or histone methylation and/or increasing histone acetylation at the promoter and the CCG repeat region.

Nonlimiting examples of a therapeutic agent of this invention include pharmacological inhibitors of DNA methylation [e.g., 5'-aza-2'-deoxycytidine (decitabine), 5'-azacytidine (vidaza), Zebularine (targets DNMTs)]; pharmacological inhibitors of histone deactylases (HDACs) [e.g., SAHA or Vorinostat, splitomicin (a Sir2 class of HDAC inhibitor, hydroxamic acid based HDAC inhibitors, Suberoylanilide hydroxamic acid (SAHA) and its derivatives, NVP-LAQ824, Trichostatin A, Scriptaid, m-Carboxycinnamic acid bishydroxamic acid (CBHA), ABHA, Pyroxamide, Propenamides, Oxamflatin, 6-(3-Chlorophenylureido)caproic hydroxamic acid (3-Cl-UCHA), A-161906, jnj16241199, tubacin and tubacin analogs, short chain fatty acid HDAC inhibitors, butyrate, phenylbutyrate, valproate, hydroxamic acid, trichostatins, epoxyketone-containing cyclic tetrapeptides, HC-toxin, Chlamydocin, Diheteropeptide, WF-3161, Cyl-1, Cyl-2, non-epoxyketone-containing cyclic tetrapeptides, Apicidin, cyclic-hydroxamic-acid-containing peptides (CHAPS), benzamides and benzamide analogs, CI-994, deprudecin, organosulfur compounds] and any combination thereof Further included herein as an agent of this invention is any siRNA, shRNA, miRNA and/or other RNAi agent targeted to the classes of DNA methyltransferases, histone deactylases and methyltransferases as are well known in the art.

Also included as an agent of this invention is an antibody that specifically reacts with the protein product(s) of the ASFMR1 transcript(s). Such an antibody can be polyclonal, monoclonal, etc., as are well known in the art. An antibody of this invention can be administered or delivered to a subject according to the methods of this invention with an adjuvant and/or immunomstimulatory agent, as are well known in the art. Such an adjuvant and/or immunomostimulatory agent can be administered before, after and/or concurrently with the administration of the antibody, in any combination and at any time interval.

Thus, in further embodiments of this invention, an antibody is provided, which can be polyclonal or monoclonal, that specifically binds the ASFMR1 polypeptide of this invention. The antibody of this invention can be in a composition with a pharmaceutically acceptable carrier and in some embodiments can further comprise an adjuvant and/or immunostimulatory agent.

The present invention additionally provides a method of treating FXTAS and/or inhibiting or otherwise modulating activity of an ASFMR1 polypeptide in a human subject in a human subject, comprising administering to the subject an effective amount of an antibody of this invention. The antibody of these methods can be in a composition with a pharmaceutically acceptable carrier and in some embodiments can further comprise an adjuvant and/or immunostimulatory agent.

In addition, the present invention provides an isolated nucleic acid encoding an intrabody that specifically binds the ASFMR1 polypeptide of this invention, as well as a vector comprising the nucleic acid. Protocols for the production and use of intrabodies to modulate activity of target molecules within a cell are well known in the art and would be readily adaptable by one of ordinary skill in the art for the specific ASFMR1 polypeptide and/or transcript of the present invention. (Marasco "Intrabodies: turning the humoral immune system outside in for intracellular immunization" *Gene Therapy* 4:11-15 (1997), the entire contents of which are incorporated by reference herein).

Methods are also provided herein of treating FXTAS in a human subject and/or inhibiting activity of an ASFMR1 polypeptide in a human subject, comprising delivering to a cell of the subject an effective amount of the nucleic acid and/or vector of this invention.

The present invention further includes embodiments in which methods are provided of inhibiting the activity or the ASFMR1 polypeptide and/or of treating FXTAS in a human subject, comprising administering to the subject a small molecule. Protocols for the production, selection and testing of small molecules for their inhibitory effects are routine and well known in the art and can be readily adapted to the methods of this invention by one of ordinary skill in the art.

The present invention further provides a method of screening small molecule libraries to identify a small molecule that inhibits activity and/or function of the ASFMR1 protein. Small molecule libraries can be obtained from various commercial entities, for example, SPECS and BioSPEC B.V. (Rijswijk, the Netherlands), Chembridge Corporation (San Diego, Calif.), Comgenex USA Inc., (Princeton, N.J.), Maybridge Chemical Ltd. (Cornwall, UK), and Asinex (Moscow, Russia). One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening. For descriptions of additional libraries, see, for example, Tan et al. "Stereoselective Synthesis of Over Two Million Compounds Having Structural Features Both Reminiscent of Natural Products and Compatible with Miniaturized Cell-Based Assays" *Am. Chem Soc.* 120, 8565-8566, 1998; Floyd et al. *Prog Med Chem* 36:91-168, 1999. Numerous libraries are commercially available, e.g., from AnalytiCon USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. In certain embodiments of the invention the screening methods are performed in a high-throughput format using techniques that are well known in the art, e.g., in multiwell plates, using robotics for sample preparation and dispensing, etc. Representative examples of various screening methods may be found, for example, in U.S. Pat. Nos. 5,985,829, 5,726,025, 5,972,621, and 6,015,692. The skilled practitioner will readily be able to modify and adapt these methods as appropriate.

In yet further embodiments, the present invention provides a method of eliciting an immune response to an ASFMR1 polypeptide, comprising administering to a subject an effective amount of an ASFMR1 polypeptide or an immunogenic fragment thereof. This method can further comprise administering to the subject an adjuvant and/or immunostimulatory agent.

Also provided herein is a method of treating FXTAS in a human subject, comprising administering to the subject an effective amount of an ASFMR1 polypeptide or an immunogenic fragment thereof. This method can further comprise administering to the subject an adjuvant and/or immunostimulatory agent.

An agent of this invention can also be Procaine (targets CpG sequences); EGCG (targets DNMTs); and Psammaplins (targets DNMTs, HDACs). The agents of this invention can be provided in any combination of the agents recited herein and/or in any combination of the agents recited herein and other therapeutic agents now know or later recognized for treating FXS.

Thus, in some embodiments, the compositions employed in the methods of this invention can comprise, consist essentially of and/or consist of a ASFMR1 protein and/or immunogenic fragment and/or epitope thereof, as well as nucleic acids encoding the ASFMRI protein and/or immunogenic fragments and/or epitopes of this invention and can further comprise, consist essentially of and/or consist of an adjuvant and/or immunostimulatory agent.

In some embodiments, such compositions can further comprise one or more than one adjuvant in the form of an amino acid sequence, and/or in the form or a nucleic acid encoding an adjuvant. The adjuvant, in the form of an amino acid sequence, can be a component of the ASFMRI polypeptide or fragment or epitope thereof and/or a separate component of a composition comprising the ASFMRI polypeptide. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of this invention. An adjuvant of this invention can be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with the polypeptide and/or nucleic acid compositions of this invention to enhance, improve or otherwise modulate an immune response in a subject without deleterious effect on the subject.

In further embodiments, an adjuvant of this invention can be, but is not limited to, an immunostimulatory agent such as a cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, and/or may be an insoluble suspension of acylated tyrosine, or acylated sugars, cationically or anionically derivatized polysaccharides, or polyphosphazenes.

Other adjuvants are well known in the art and include MF 59, LT-K63, LT-R72 (Pal et al., *Vaccine* 24(6):766-75 (2005)), QS-21, Freund's adjuvant (complete and incomplete), aluminum hydroxide, N-acetyl-muramyl-L-threonyl- D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, the nucleic acid of this invention can include an adjuvant by comprising a nucleotide sequence encoding an antigen of this invention and a nucleotide sequence that provides an adjuvant function, such as CpG sequences. Such CpG sequences, or motifs, are well known in the art.

An adjuvant of this invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of an immunogenic composition of this invention to a subject.

Furthermore, any combination of adjuvants, such as immunostimulatory cytokines, can be co-administered to the subject before, after and/or concurrent with the administration of an immunogenic composition of this invention. For example, combinations of immunostimulatory cytokines, can consist of two or more immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

Pharmaceutical compositions comprising the immunogenic proteins, fragments and or epitopes of this invention and a pharmaceutically acceptable carrier are also provided. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

As set forth herein, the term "immunogenic fragment" means a fragment (e.g., a peptide) of a protein that can stimulate either humoral or cellular immune responses in the subject. An immunogenic fragment of this invention can comprise, consist essentially of and/or consist of one, two, three, four or more epitopes of a protein of this invention. An immunogenic fragment can be any fragment of contiguous amino acids of the CPAF protein and can be for example, 5, 10, 15, 20, 25, 30, 35, 40, 45, 50, 75, 100, 150, 200, 250, 300, 350, 400, 450, 500 or 550, 600, 700, 800, 900 or 1000 amino acids in length. Identification of any such immunogenic fragments is routine in the art.

As noted herein, an immune response elicited or produced by carrying out the methods of this invention can be a protective immune response, a cellular immune response, a humoral immune response, a Th1 immune response, a Th2 immune response and any combination thereof.

To stimulate the humoral arm of the immune system, i.e., the production of antigen-specific antibodies, an immunogenic fragment can include at least about 5-10 contiguous amino acid residues of the full-length molecule, or at least about 15-25 contiguous amino acid residues of the full-length molecule, or at least about 20-50 or more contiguous amino acid residues of the full-length molecule, that define one or more epitopes, or any integer between five amino acids and the full-length sequence, provided that the fragment in question retains immunogenic activity, as measured by any art-known assay, such as, e.g., the ones described herein and/or those known in the art.

Regions of a given polypeptide that include an epitope can be identified using any number of epitope mapping techniques, well known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al. (1984) *Proc. Natl. Acad. Sci. USA*

81:3998-4002; Geysen et al. (1986) *Molec. Immunol.* 23:709-715, all incorporated herein by reference in their entireties.

Similarly, conformational epitopes are readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids, and these are not typically predicted by the above-described methods for identifying humoral epitopes. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenic fragments can also be identified based on their ability to stimulate lymphocyte proliferation in response to stimulation by various fragments from the antigen of interest.

The term "epitope" as used herein refers to at least about 3 to about 5, or about 5 to about 10 or about 5 to about 15, and not more than about 100, 500 or 1,000 amino acids (or any integer therebetween), which define a sequence that by itself or as part of a larger sequence, binds to an antibody generated in response to such sequence and/or stimulates a cellular immune response. There is no critical upper limit to the length of the fragment, which can comprise nearly the full-length of the protein sequence, or even a fusion protein comprising two or more epitopes from a single or multiple proteins. An epitope for use in the present invention is not limited to a polypeptide having the exact sequence of the portion of the parent protein from which it is derived. Thus, the term "epitope" encompasses sequences identical to the native sequence, as well as modifications to the native sequence, such as deletions, additions and substitutions (generally, but not always, conservative in nature) that are readily produced and/or identified as epitopes according to methods standard in the art.

In additional embodiments, the present invention provides a method of providing passive immunity against the effects of ASFMR1 protein in a subject, comprising administering to the subject an effective amount of an antibody of this invention to the subject. An antibody of this invention can be an antibody that specifically binds an ASFMRI protein or fragment or epitope thereof. The administration of antibodies to a subject in passive immunity protocols is well known and standard in the art. Such antibodies can be administered in combination with an adjuvant and/or immunostimulatory agent as described herein.

As used herein, the term "antibody" includes intact immunoglobin molecules as well as fragments thereof, such as Fab, F(ab')2, and Fc, which are capable of binding the epitopic determinant of an antigen (i.e., antigenic determinant). Antibodies that bind the polypeptides of this invention are prepared using intact polypeptides and/or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize a host animal (e.g., a mouse, rat, goat, sheep, human or rabbit). The polypeptide or peptide antigens can also be administered with an adjuvant, as described herein and as otherwise known in the art.

The terms "antibody" and "antibodies" as used herein refer to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, and/or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. Nos. 4,474,893 or 4,816,567. The antibodies can also be chemically constructed according to the method disclosed in U.S. Pat. No. 4,676,980. The antibody can further be a single chain antibody or bispecific antibody.

Techniques for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies (e.g., scFv) can be adapted, using methods known in the art, to produce single chain antibodies specific for the polypeptides and/or fragments and/or epitopes of this invention. Antibodies with related specificity, but of distinct idiotypic composition, can be generated by chain shuffling from random combinatorial immunoglobin libraries (Burton 1991. *Proc. Natl. Acad. Sci.* 88:11120-3).

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein (*Nature* 265:495-97 (1975)). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope of interest.

The terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete.

By "prime," "primed" or "priming" (and grammatical variations thereof) as used herein, it is meant to initiate an active immune response that is less than protective until a second dose (booster) is given at a later time.

"Boost" or "booster" means a second immunization, after an initial (or "priming") immunization that enhances the immune response of the subject. Therefore, in some embodiments, the invention provides a composition that produces an anamnestic response against an ASFMRI polypeptide, in a sensitized subject, comprising an anamnestic response-inducing amount of an ASFMRI protein immunizing component. As used herein, the term "anamnestic response" means a secondary (booster) immune response in a sensitized subject. By "sensitized subject" is meant a subject that has previously been in contact with ASFMRI antigen or antigens, either by natural exposure or by vaccination (primary immunization) with ASFMRI polypeptide immunizing components.

The terms "reduce," "reduced," "reducing," and "reduction" (and grammatical variations thereof), as used herein, describe a decrease in a disease-related parameter or symptom that is of some therapeutic value or benefit to the subject.

As used herein, the terms "elicit" or "induce" or "produce" (or grammatical variations thereof) in the context of an immune response against ASFMRI polypeptide are intended to encompass the activation and/or stimulation of cells and other components of the immune system in a subject to ameliorate the effects of ASFMRI polypeptide-related pathology in the subject. The immune response of this invention can be a protective immune response, for example, as desired in vaccination methods to treat and/or prevent a disorder or pathological effect. Protection is not required if there is some other purpose for inducing the immune response, for example, for research purposes or to produce antibody for passive immunizations or as a reagent (e.g., to detect, isolate and/or identify ASFMRI polypeptide).

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, prevention or delay of the onset of the disease, disorder, or illness, and/or change in clinical parameters of the condition, disorder, disease or illness, etc., as would be well known in the art.

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

The terms "immunogenic amount" or "effective immunizing dose," as used herein, unless otherwise indicated, mean a dose of a composition of this invention sufficient to induce an immune response (which can be a protective response) in the treated subject that is greater than the inherent immunity of non-immunized subjects. An immunogenic amount or effective amount or effective immunizing dose in any particular context can be routinely determined using methods known in the art.

In some embodiments, an effective immunizing dose or immunogenic amount or effective amount can comprise one or more (e.g., two or three or four or more) doses of the immunogenic composition of this invention at any time interval (e.g., hourly, daily, weekly, monthly, yearly, etc.) so as to achieve and/or maintain the desired level of protection and/or other therapeutic benefit.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

The terms "protective immunity" or "protective immune response," as used herein, are intended to mean that the subject mounts an active immune response to the immunogenic composition and/or that the subject has been provided with passive immunity, such that upon subsequent exposure or a challenge, the animal is able to resist and/or overcome infection and/or disease. Thus, a protective immune response will decrease the incidence of morbidity and/or mortality from subsequent exposure to the ASFMRI polypeptide of this invention.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

In the methods of treatment provided herein, the therapeutic agents described herein and that are known in the art or later developed are administered to a subject according to known protocols for dosage and administration. Typically, such therapeutic agents are provided as pharmaceutical compositions in a pharmaceutically acceptable carrier.

The pharmaceutical compositions of this invention include those suitable for oral, intranasal, rectal, topical, inhalation (e.g., via an aerosol) buccal (e.g., sub-lingual), vaginal (e.g., vaginal ring), rectal, intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration. The compositions herein can also be administered via a skin scarification method or transdermally via a patch, liquid or gel. The compositions can be delivered subdermally in the form of a biodegradable material that releases the compositions over time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, prevention or delay of the onset of the disease, disorder, or illness, and/or change in clinical parameters of the condition, disorder, disease or illness, etc., as would be well known in the art.

The frequency of administration of a pharmaceutical composition of this invention can be as frequent as necessary to impart the desired therapeutic effect. For example, the composition can be administered one, two, three, four or more times per day, one, two, three, four or more times a week, one, two, three, four or more times a month, one, two, three or four times a year and/or as necessary to control the condition. In some embodiments, one, two, three or four doses over the lifetime of a subject can be adequate to achieve the desired therapeutic effect. In some embodiments, alternate day dosing can be employed (e.g., every other day). The amount and frequency of administration of the composition of this invention will vary depending on the particular condition being treated or to be prevented and the desired therapeutic effect.

The present invention is more particularly described in the following examples that are intended as illustrative only since numerous modifications and variations therein will be apparent to those skilled in the art.

EXAMPLES

Identification of an Antisense Transcript at the Human FMR1 Locus

Cell Cultures

Human lymphoblastoid cell lines from individuals with the characterized CGG repeat expansions were established by Epstein-Barr virus transformation and characterized previously (13). Human:hamster hybrid cell lines, GM06318 and X8-6T2S1, retaining either an active or an inactive human X chromosome, respectively, as well as 19AS2, derived by 5'-azacytidine (5aC) treatment of X8-6T2S1, were described previously (34). Cells were maintained in RPMI 1640 medium supplemented with 10% fetal bovine serum (HyClone, Utah), glutamine, and penicillin-streptomycin (Invitrogen) at 37° C. in a humidified atmosphere of 5% $CO_2$.

Nuclear Isolation

Lymphoblastoid cells (4.0 to $6.0 \times 10^5$) were harvested by centrifugation at 700×g for 5 minutes at 4° C. The cells were washed one time with ice-cold PBS and pelleted by centrifugation at 700×g for 5 minutes at 4° C. The cells were resuspended in a 5× volume of ice-cold buffer A (10 mM HEPES, pH 7.9, 1.5 mM $MgCl_2$, 10 mM KCl, supplemented with 1 mM DTT), incubated on ice for 10 minutes to swell, and then pelleted at 500×g for 10 minutes at 4° C., and the supernatant was discarded. The cell pellet was resuspended in 2× volume of buffer A and the outer cell membranes were disrupted by Dounce homogenization, 15 strokes with pestle "B" or "tight", on ice. The homogenate was centrifuged at 500×g for 10 minutes at 4° C. The upper, less turbid phase containing the cytoplasmic fraction was separated from the lower, nuclei fraction. RNA was extracted from each fraction.

RNA Isolation

Total RNA from lymphoblastoid cell lines was isolated using standard methods (TRIZOL, lnvitrogen). The isolated RNA was treated with TURBO DNA-free DNase (Ambion) to remove contaminating DNA. For poly-A RNA enrichment, total RNA was incubated with magnetic oligo-dT linked beads (Invitrogen) and eluted with 10 mM Tris-HCl. As a control for non-poly-A RNA, the unbound fraction was collected and the remaining RNA was harvested with TRIZOL.

Blood samples were collected directly into Tempus Blood RNA Tubes (Applied Biosystems, Foster City, Calif.) following informed consent and according to an approved Institutional Review Board protocol. Total RNA from peripheral blood leukocytes from individuals carrying either a normal, premutation or full mutation allele was isolated using the ABI PRISM™ 6100 Nucleic Acid PrepStation according to the manufacturer's protocol.

cDNA Generation cDNA was generated with Superscript III (Invitrogen) under the following conditions. The appropriate primer (random hexamers, oligo-dT, gene-specific or strand-specific) was added to 1-3 μg of RNA and incubated at 70° C. for 5 minutes in a thermocycler. The temperature was cycled to 50° C. and the RNA/primer mixture equilibrated for 5 minutes. Next, the reaction mixture, nuclease free $H_2O$, 5× buffer, RNase inhibitor, dNTPs, DTT, and RT (except for no RT control), pre-equilibrated at 50° C., was added to the RNA/primer mixture and incubated for two hours at 50° C. The RT was inactivated at 70° C. for 5 minutes. Synthesis of cDNA was verified by amplification of the control transcript, CTCF, using the primers CTCF For: 5'-TGATGAGAGACCACA-CAAGTGCCA-3' (SEQ ID NO:62) and CTCF Rev: 5'-CT-GCACAAACTGCACTGAAACGGA-3' (SEQ ID NO:63). RNA was tested for DNA contamination using a no-RT control and primers were verified by amplification of genomic DNA (genomic DNA control).

Strand-Specific RT-PCR

For strand-specific RT-PCR, cDNA was generated using gene specific primers which had a linker (LK) sequence, LK 5'-CGACTGGAGCACGAGGACACTGA-3' SEQ ID NO:22) attached to the 5'-end. Primer sequences are listed in Table 2. cDNA was generated with 1-3 µg of RNA and Superscript III (Invitrogen) at 50° C. PCR amplification of the strand-specific transcripts was performed using the LK sequence alone as a primer and a gene-specific reverse primer (35 cycles of 94° C. 30 s, 55° C. 30 s, and 68° C. 1 min). PCR amplification of the strand-specific transcripts across the CGG repeat region was performed using 1.7M betaine essentially as described previously (28). The PCR products were cloned into the pCR®4-TOPO vector (Invitrogen) and sequenced using an ABI Prism 3730xI DNA analyzer (Applied Biosystems).

Semi-Quantitative RT-PCR

To establish the linear range for each gene-specific and control primer set, aliquots of the PCR reaction were collected every two cycles ranging from 26 to 40 cycles. The linear range for the FMR1 primer set, Exon 2Forward, 5'-CATGAAGATTCAATAACAGTTGC-3' (SEQ ID NO:64), with Exon 4Reverse, 5'-CACTTTAGCTAACCAC-CAACAG-3' (SEQ ID NO:65), was established at 30 to 36 cycles, while the linear range for the ASFMR1 primer set, −1427Forward, 5'-CATGTGACTACTCCAAAGAC-CCTAGTCC-3' (SEQ ID NO:33), with −1168Reverse, 5'-CT-TCCATGATGGCGGAACATGACCTAGTC-3' (SEQ ID NO:51), was at 34 to 40 cycles. The ASFMR1 primers were designed in an area common to the spliced and unspliced transcripts. As a control, an adjustable 18S primer and competimer set (Ambion) was used to allow PCR amplification of 18S in the same linear range as the gene-specific primer set. The FMR1/ASFMR1 multiplex RT-PCR was performed with an 18S primer to competimer ratio of 3:17 for 35 cycles.

Real Time RT-PCR

FMR1 and ASFMR1 transcript levels were quantified using real time PCR performed on the automated ABI 7900 PCR machine (Applied Biosystems) using Fast Start SYBR Green Master Mix (ROCHE) with ROX passive reference dye added. cDNA was generated with random decamers using 1.5 µg RNA, then diluted 1:1. Two µl of cDNA was used as template for the real time reaction. ASFMR1 was amplified with primers −1427Forward, 5'-CATGTGACTACTC-CAAAGACCCTAGTCC-3' (SEQ ID NO:33), and −1185Reverse, 5'-CATGACCTAGTCTGGGGTGGAG-3' (SEQ ID NO:52), the FMR1 primers were the same as those used for semi-quantitative RT-PCR. The standard curve assay as described by Applied Biosystems was used for absolute quantification. The values calculated for FMR1 and ASFMR1 transcript levels were normalized to β-Glucoronidase (GUS) expression as a control, with primers GUS Forward: 5'-CT-CATTTGGAATMGCCGATT-3' (SEQ ID NO:66) and GUS Reverse: 5'-CCGAGTGAAGATCCCCTTTTA-3' (SEQ ID NO:67) as described previously (12). Approximate threshold cycle ($C_t$) values with these primers for normal lymphoblastoid cells were as follows: FMR1 23, ASFMR1 29, and GUS 28 cycles. PCR cycling was performed at [94°/2 min, (94°/30 s, 60°/30 s, 72°/30 s)×40] with an additional ramping step added after cycling to calculate dissociation curves and confirm that fluorescence detected was due to full size PCR product and not PCR artifacts. P-values were determined by standard student t-test.

RLM-RACE

RNA ligase-mediated rapid amplification of 5'- and 3'-cDNA ends (RLM-RACE) was performed using the GeneRacer™ Kit (Invitrogen) according to the manufacturer's protocol. This protocol allows obtaining full length ends by eliminating uncapped transcripts. Briefly, for 5'-RACE, either total or poly(A) RNA from commercially derived human brain tissue (Ambion) and lymphoblastoid cell lines with a normal or a premutation allele, H930-1 and FX-TF, respectively, was treated with calf intestinal phosphatase to remove the 5'-phosphates of incomplete transcripts. The 5'-cap structure was removed with tobacco acid pyrophosphatase to leave a 5'-phosphate available for subsequent ligation of the GeneRacer™ RNA oligonucleotide. The ligated mRNA was reversed transcribed using Superscript III and random hexamers. In a separate analysis, phosphatase treatment and/or removal of the 5'-cap structures was omitted to allow amplification of both capped and uncapped transcripts or to specifically enrich for uncapped transcripts only. For 3'-RACE, total RNA was reverse-transcribed using Superscript III and the GeneRacer™ Oligo-dT primer, containing a linker sequence attached to the 5'-end of the oligo-dT primer. For PCR amplification of the first-strand cDNA, each primer pair contained a gene-specific primer complementary to the ASFMR1 sequence (or to the control β-Actin sequence) and the appropriate GeneRacer™ primer for the 5'- or 3'-end. A second round of PCR amplification was performed using 1 µl of the previous PCR product as template and a 5'- or 3'-nested GeneRacer™ primer and a corresponding gene-specific nested primer (by either touch-down PCR as described in the RLM-RACE kit or 35 cycles of 94° C. 30 s, 55° C. 30 s, and 68° C. 5 min). Sequences of gene-specific primers used for 5' and 3' RACE are listed in Table 2. The PCR products were cloned into the pCR®4-TOPO vector (Invitrogen) and sequenced using an ABI Prism 3730xI DNA analyzer (Applied Biosystems). The identified 5'- and 3'-ends were confirmed by strand-specific RT-PCR.

Northern Blot Analysis

Northern blot analysis was performed according to standard protocols. The ASFMR1 and 18S probes were radioactively labeled using Ready-to-Go DNA labeling beads (Amersham). For small RNA Northern blot analysis, 30 µg RNA from each cell line were separated electrophoretically in a 10% polyacrylamide/8M urea/1× TBE gel. RNA was electroblotted onto Nytran SPC nylon membrane (Whatman) in 1× TBE at 250 mA for 45 minutes, and UV crosslinked. Blots were hybridized overnight at 35° C. in Ultrahybe Oligo buffer (Ambion) with radiolabeled oligonucleotide probes complementary to the FMR1 and ASFMR1 sequences of interest.

Analysis of the CGG Repeat Size and Methylation Status

Southern blot and PCR-based analyses were performed as described previously (28). Genomic DNA was isolated from peripheral blood leukocytes (5 ml of whole blood) using standard methods (Puregene and Purescript Kits, Gentra Inc.). For Southern blot analysis, 5-10 ug of isolated DNA was digested with EcoRI and NruI. Hybridization was performed using the StB12.3 probe specific for the FMR1 gene. For PCR-based analysis of genomic DNA, hybridization was performed with an oligonucleotide probe (CGG)10. Analysis of trinucleotide expansion allele size was conducted using an Alpha Innotech FluorChem 8800 Image Detection System.

Electrophoretic Mobility Shift Assay

Fifteen 200-300 bp DNA fragments were $^{32}$P-labeled, gel purified, and used as DNA probes for gel mobility shift assays with equal amounts of the in vitro translated 11-ZF DNA binding domain and full-length human CTCF proteins as described (32). A known CTCF binding site in the myotonic dystrophy, DM1, locus was used as a positive control (32). Binding reactions were carried out in the buffer containing standard PBS with 5 mM $MgCl_2$, 0.1 mM $ZnSO_4$, 1 mM DTT, 0.1% NP40, and 10% glycerol in the presence of poly (deoxyinosinic-deoxycytidylic acid). Reaction mixtures of 20 µl of final volume were incubated for 30 min at room temperature and then analyzed on 5% nondenaturing PAGE run in 0.5× Tris-borate-EDTA buffer.

Chromatin Immunoprecipitation

The ChIP assays were performed as previously described (49), using commercially available antibody against CTCF (Upstate). Briefly, formaldehyde cross-linked chromatin after sonication was incubated with the CTCF antibody, then precipitated by the addition of protein-G sepharose. After reverse cross-linking, the IP products were analyzed by semi-quantitative PCR. A region of the DM1 locus, which is positive for CTCF binding (32) was used as a positive control to verify CTCF-specific ChIP. A region of the KIAA522 locus, which is negative for CTCF binding (50) was used for normalization.

Accession Codes

GenBank®: Homo sapiens ASFMR1d mRNA, from +10243 to −2490 with splice from +10018 to +315, EU48200; Homo sapiens ASFMR1c mRNA, from +10243 to −2490 with splice from +10018 to +315 and from −538 to −919, EU48201; Homo sapiens ASFMR1b mRNA, from +10243 to −2490 with splice from +10018 to +315, −274 to −530 and −635 to −921, EU48202; Homo sapiens ASFMR1a mRNA, from +10243 to −2490 with splice from +10018 to +315 and from −274 to −921, EU48203; Homo sapiens ASFMR1e mRNA, from +10243 to −2490 with splice from +10018 to +315 and from +10155 to +10070, EU48203

Identification of an Antisense Transcript at the Human FMR1 Locus.

Identification of antisense transcripts at several disease-associated trinucleotide repeat loci, including DM1 and SCA8 (24, 25), suggests that bidirectional expression might result in RNA-mediated transcriptional silencing of the expanded repeats and that the sense and/or antisense transcript might contribute to a clinical phenotype. To test whether similar mechanisms apply to the human FMR1 locus, we analyzed the locus for the presence of antisense transcripts. Human FMR1 is located in a gene poor region, however, the genome database indicates that a number of spliced and unspliced expressed sequence tags (ESTs) overlap the FMR1 gene locus. While many of the ESTs reflect portions of the FMR1 transcript, there are a number of ESTs in the antisense direction. Using strand-specific RT-PCR (FIG. 1B) on human lymphoblastoid cells derived from individuals with characterized CGG repeat expansions, we mapped an antisense transcript at the position −500 to −1000 bp relative to the FMR1 major transcription start site (26) and at the position +337 to +210 bp overlapping FMR1 at exon 1 downstream of the CGG repeat (FIGS. 1A and C, panels 1, 5). Both of these regions of antisense transcription were identified in the cell lines with normal or premutation alleles, H930-1 and FX-TF respectively, but not in a full mutation cell line, FX-GM (FIG. 1C, panels 1, 5), similar to the expression pattern of the FMR1 transcript in these cell lines (FIG. 1 C, panel 7). No sense transcription was detected upstream of the known FMR1 transcription start sites (26, 27) (FIG. 1C, panel 3).

Figure 2:
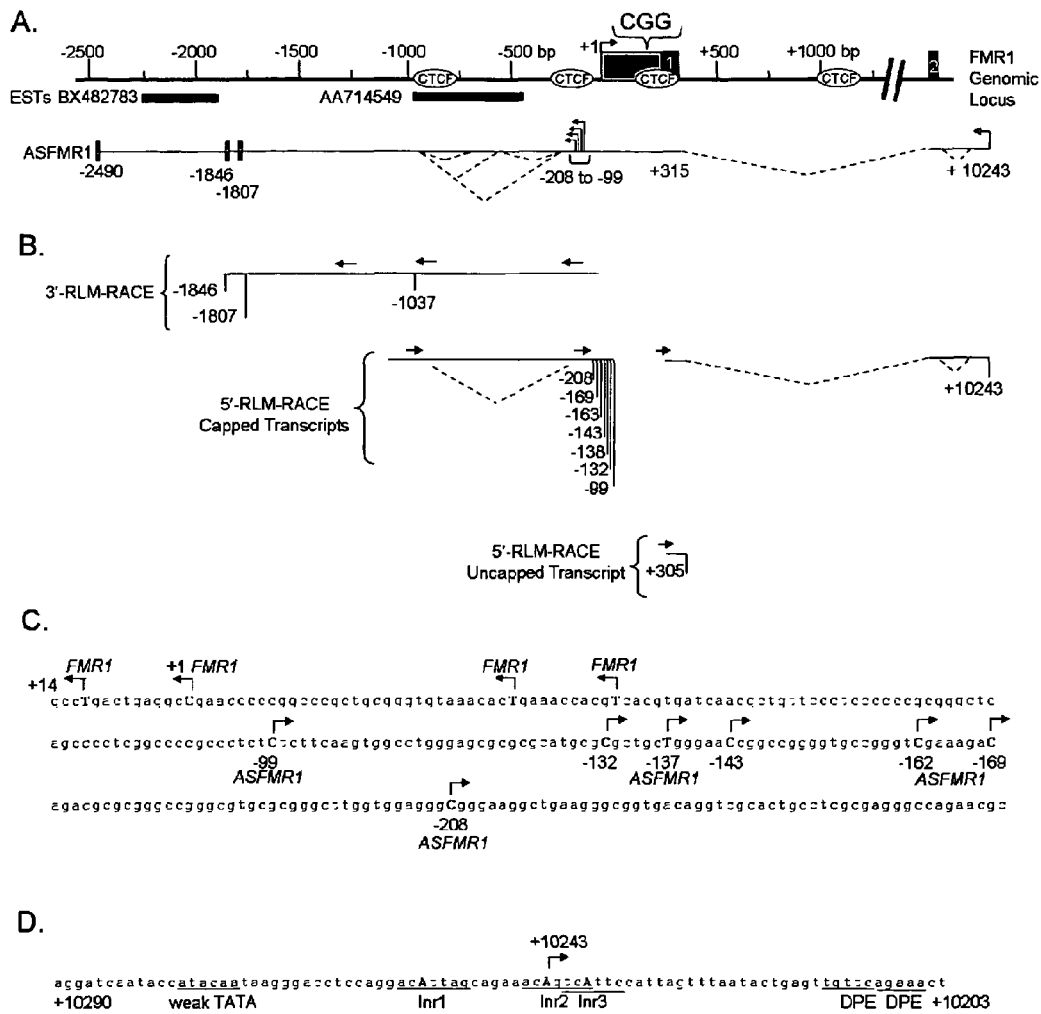
FIGS. 2A-D. General organization of the AntiSense Transcript at the FMR1 Locus, ASFMR1. (A) The FMR1 genomic locus is depicted as in FIG. 1A. The ASFMR1 transcript summary is indicated below the FMR1 genomic locus; arrows indicate the transcription initiation sites identified by 5'-RACE and location of putative promoters. Characterized splice sites are indicated by dotted lines. Thick black vertical bars depict polyadenylated 3'-ends of the ASMFR1 transcript. (B) Identification of the 3'- and 5'-ends of the ASFMR1 transcript by RLM-RACE using total and polyA RNA from human brain and a normal human lymphoblastoid cell line, H930-1. Location of primers used for RACE is indicated by arrows. Identified 3'- and 5'-ends of the ASFMR1 transcript are indicated numerically. 5'-RACE results for capped and uncapped transcripts are depicted separately. (C) The putative bi-directional promoter region (SEQ ID NO:7) for the ASFMR1 transcript initiated at −99 to −208, as indicated numerically and with arrows. Previously identified sites for FMR1 transcription initiation, including the major site indicated with a +1, are shown by arrows. All numbering is relative to FMR1. (D) Putative promoter region (SEQ ID NO:8) for the transcript initiated at +10243. Core promoter elements are indicated; a previously characterized weak TATA box, Initiator (Inr) elements and downstream promoter elements (DPE) are underlined. All numbering is relative to FMR1
Figure 6:
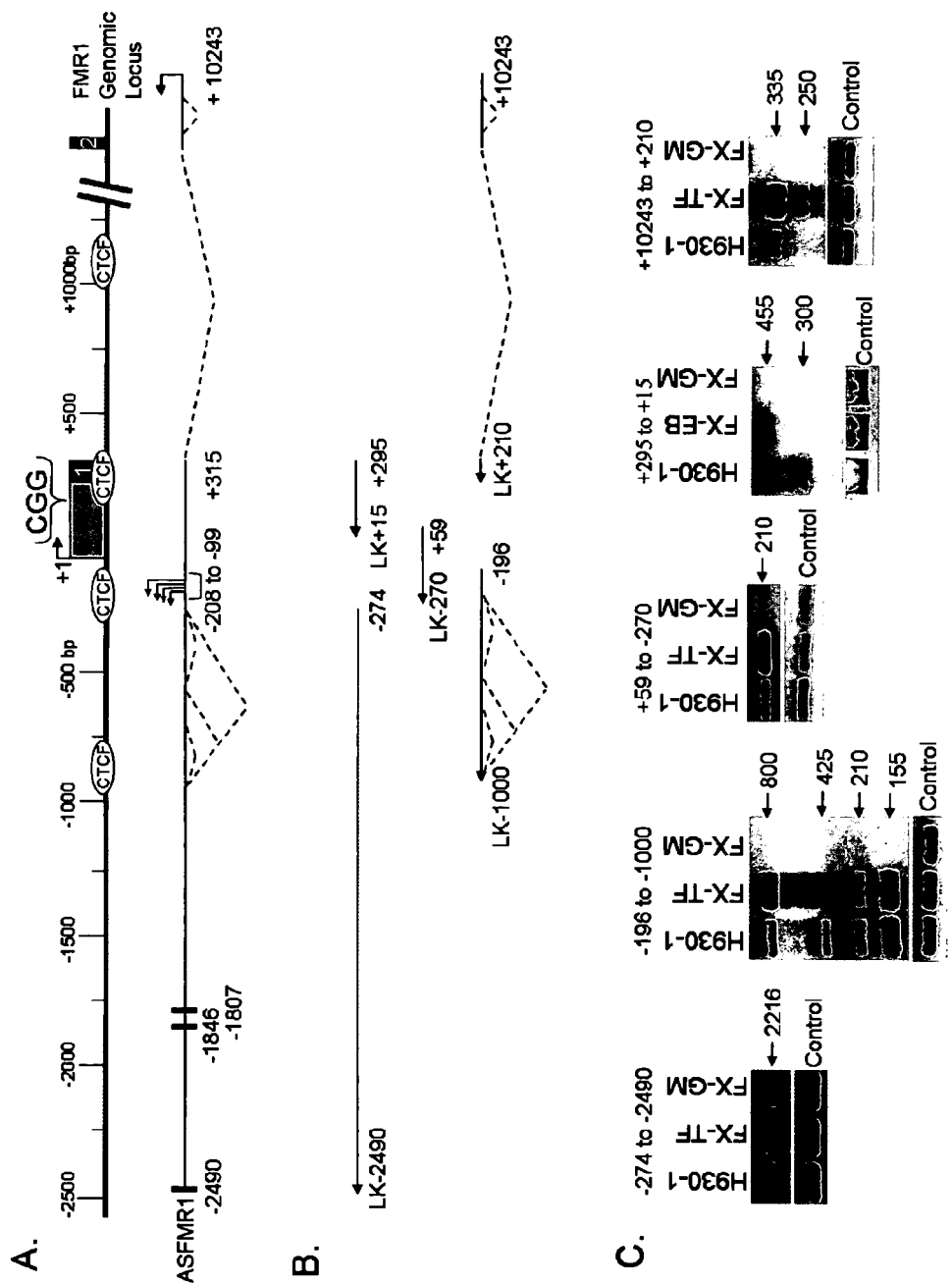
FIGS. 6A-C. Continuous antisense transcript at the FMR1 locus spans CGG repeat in the antisense orientation. (A) The FMR1 genomic locus is depicted as in FIG. 1A. The ASFMR1 transcript summary is indicated below the FMR1 genomic locus as in FIG. 2A. (B) Multiple overlapping strand-specific RT-PCR regions, spanning the ASFMR1 transcript from −2490 to +10243, are depicted by arrows. Numeric values indicate the location of each linker containing primer used for strand-specific cDNA generation, as well as the reverse primer used for PCR amplification, relative to FMR1 as described in FIG. 1. Primer sequences are listed in Table 2. (C) Strand-specific RT-PCR analysis of human lymphoblastoid cell lines identified overlapping antisense transcripts at the position −274 to −2490 bp, −196 to −1000, +59 to −270 and +10243 to +210 bp in normal H930-1, and premutation, FX-TF, cells, but not in full mutation, FX-GM. Betaine based strand-specific RT-PCR analysis to amplify CGG rich sequences identified an antisense transcript spanning the CCG repeat region from +295 to +15 in normal, H930-1, and premutation, FX-EB, cells containing 82 CGG repeats, but not in full mutation, FX-GM. The synthesis of cDNA was verified by amplification of the control transcript, CTCF. The −196 to −1000, +59 to −270 and +10243 to +210 strand-specific RT-PCR products and the control transcript were amplified in a linear range. Semi-quantitative analysis revealed increased levels of ASFMR1 transcript in premutation cells relative to normal as detected by primers pairs −196/−1000 and −1427/−1168 (FIG. 4), as well as by primers pairs +59/−270 and +10243/+210 that detect the levels of the ASFMR1 transcript initiated at the +10243 putative promoter. The ASFMR1 expression was normalized to the control transcript. The semi-quantitative strand-specific RT-PCR was repeated for each pair of primers at a minimum of two-three times.

The identification of antisense transcripts on both sides of the CGG repeat suggested that an antisense transcript overlaps the FMR1 CGG repeat region. Northern blot analysis to identify the full-length antisense transcript was unproductive, likely due to the low abundance of the transcript. However, using multiple strand-specific RT-PCR, including a betaine-based protocol for the amplification of CGG•CCG repeats (28), we identified overlapping regions of antisense transcription from the position +295 bp to −1000 bp, indicating a continuous transcript spanning the FMR1 CGG repeat region in the antisense orientation (FIG. 2A and FIG. 6). We named this transcript the AntiSense Transcript at the FMR1 Locus, ASFMR1.

Identification of Multiple Splice Forms

Figure 7:
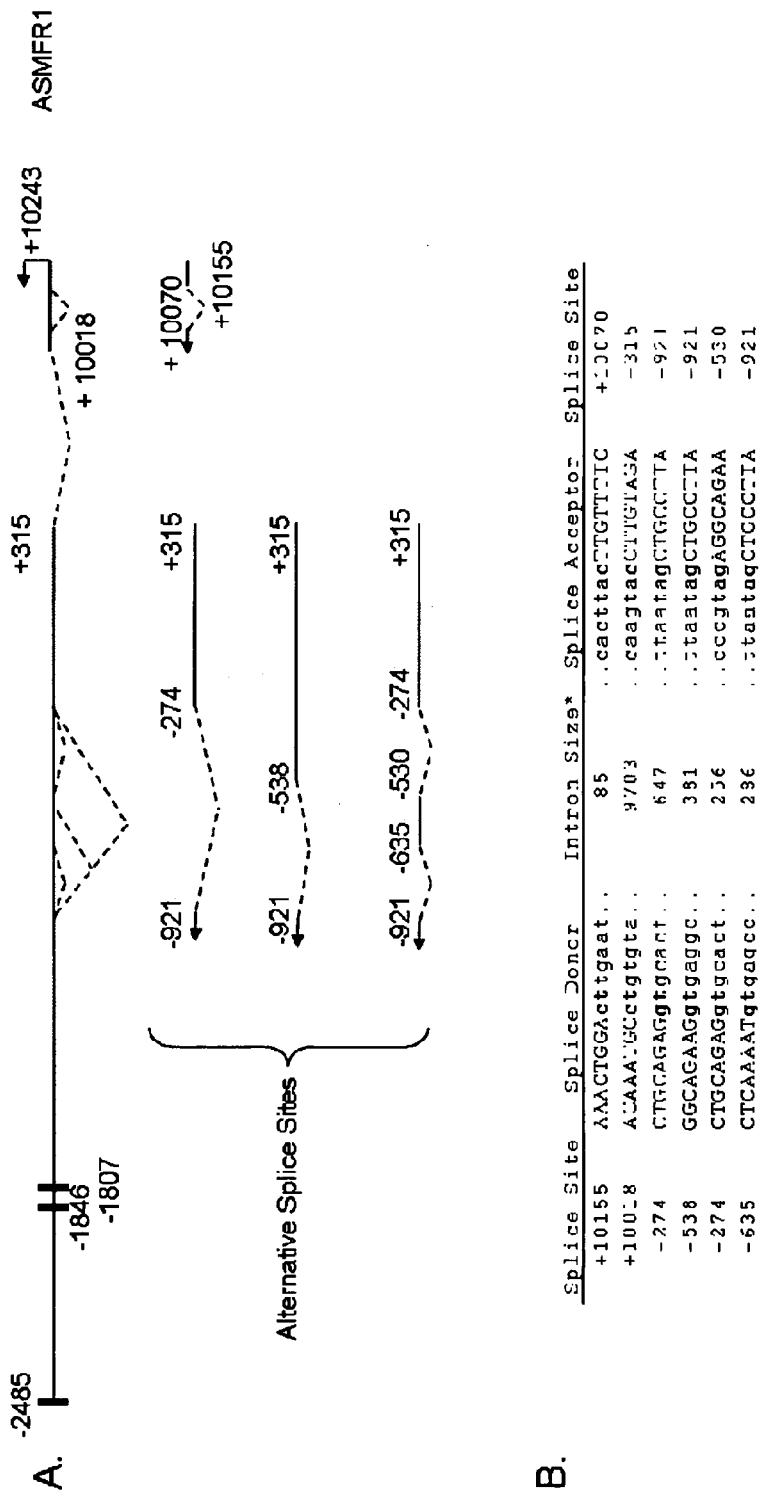
FIGS. 7A-B. Splice donor/acceptor usage and poly(A) signal for the ASFMR1 transcript. (A) ASFMR1 is depicted by a horizontal line, splice sites are indicated numerically and by dotted lines. Arrows indicate the direction of transcription. Alternative splice forms are highlighted by gray rectangles. (B) Splice donor and splice acceptor sites (SEQ ID NOs:10-19) and poly(A) signal (SEQ ID NO:20) for ASFMR1. Positions of splice sites are numbered relative to FMR1 as described in FIG. 1. Exonic sequences are shown in capital letters and intronic in lower case. The splice donor and splice acceptor sequences are shown in bold. The size of each intron is indicated in bp.
Figure 10:
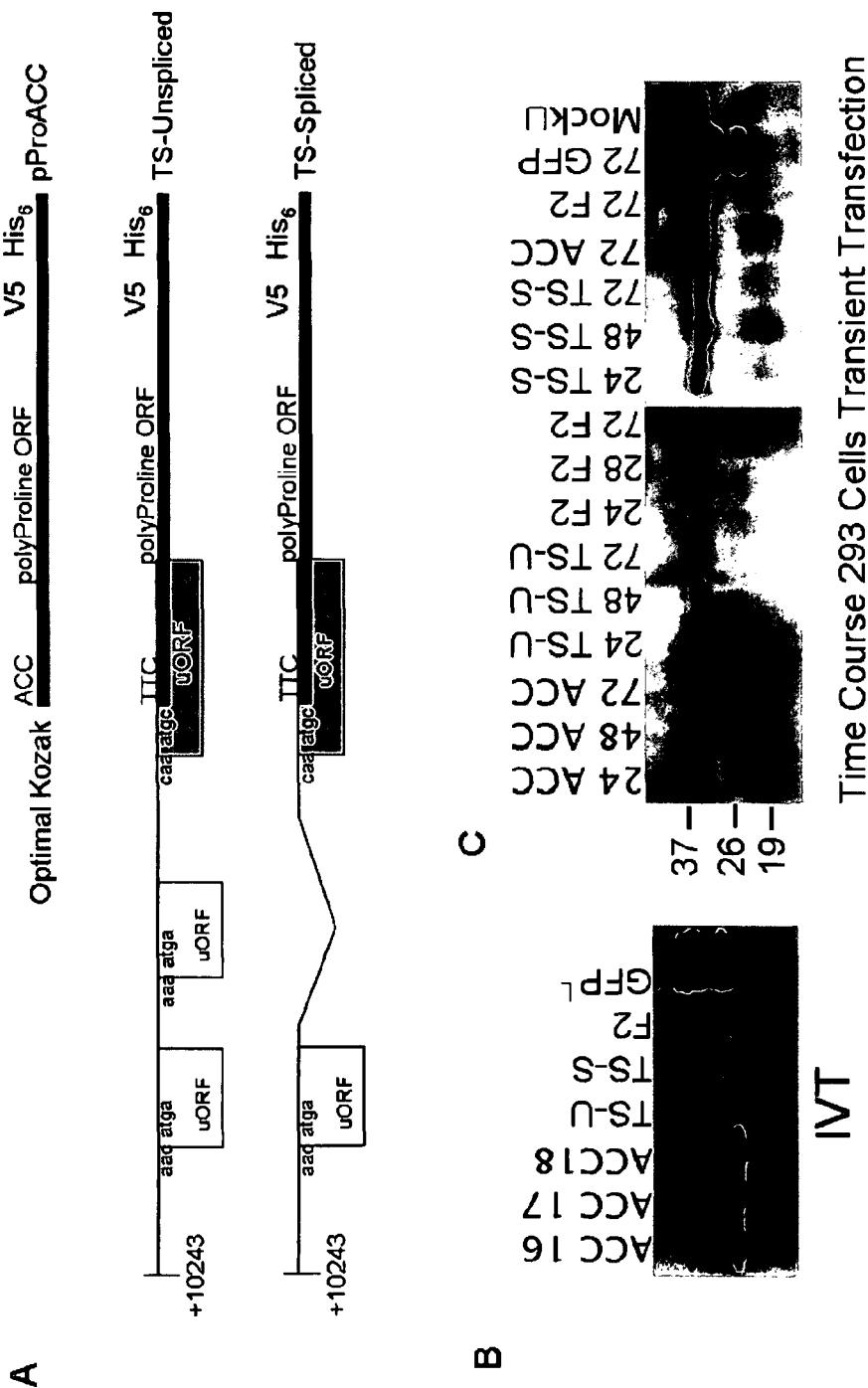
FIGS. 10A-C. ASFMR1 polyproline ORF can be translated both in vitro and in vivo. (A) Schematic diagram of the ASFMR1 expression cassettes based on pcDNA3.1-V5-His-Topo vector. (B) Analysis of in vitro translated proteins labeled with $^{35}$S-Met on 15% SDS PAGE gel. (C) Time course of the ASFMR1 protein expression in 293 cells after transient transfection. Western blot analysis using anti-V5 antibody.

Further mapping of ASFMR1 revealed multiple splice forms of the transcript, as depicted in FIG. 1A. Using primers from −1000 to −196, we identified the unprocessed form and three different spliced forms of the ASFMR1 transcript (FIG. 1D). Removal of 381 nt from −538 to −921 results in transcript C (FIG. 1D). An intermediate form B splices a total of 542 nt of sequence from −274 to −530 and from −635 to −921, resulting in an additional short exon approximately 100 nt in size (FIG. 10, transcript B). The largest splice removes 647 nt of the sequence from −274 to −921 (FIG. 1D, transcript A). The spliced transcripts A, B, and C, follow the consensus splice donor/acceptor recognition sequence, gt to ag (FIG. 7).

Both spliced and unspliced forms of the transcript were detected in normal and premutation cell lines, H930-1 and FX-TF, respectively, but not in the full mutation line, FX-GM. While the stoichiometry of the bands suggests that the major splice form for both cell lines is transcript A, there are noticeably different ratios of the intermediate transcripts, B and C, to the unspliced transcript in the premutation cell line, FX-TF, relative to the normal cell line, H930-1 (FIG. 1D).

The ASFMR1 Transcript is Polyadenylated

To test whether the ASFMR1 transcript is polyadenylated, we used oligo-dT beads (Invitrogen) to pull-down polyA RNA from the normal cell line, H930-1. Both oligo-dT-bound and unbound fractions were analyzed for the presence of the antisense transcript at −500 to −1000 and +337 to +210, as well as two control transcripts, FMR1, a known polyadenylated transcript, and non-polyadenylated 18S rRNA. Similar to FMR1, the ASFMR1 transcript was enriched in the polyA fraction relative to the unbound, whereas 18S was enriched in the unbound fraction (FIG. 1E).

Figure 3:
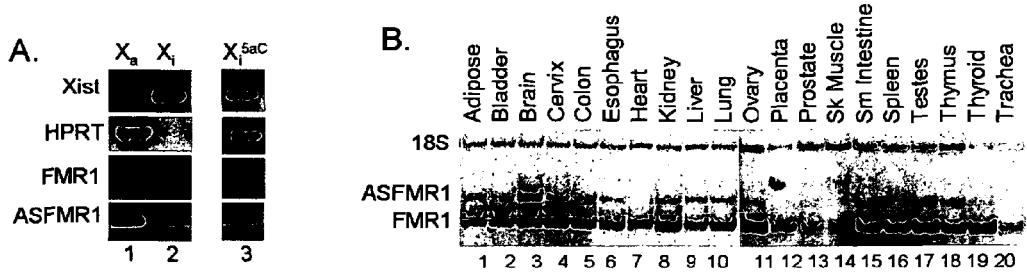
FIGS. 3A-B. Expression profile of the ASFMR1 transcript. (A) RT-PCR of human:hamster hybrid cells using primers to human XIST, HPRT, FMR1 and ASFMR1. $X_a$ and $X_i$ contain the active and inactive X chromosome, respectively. $X_i^{5aC}$ indicates the $X_i$ cell line after 5aC reactivation treatment. (B) Semi-quantitative multiplex RT-PCR analysis of human tissues using primers to ASFMR1, FMR1 and 18S, as described in the Examples. Each tissue type is indicated and reflects a pool of RNA derived from three different individuals (Ambion).

To verify that the ASFMR1 transcript is polyadenylated, we performed 3'-RACE using an oligo-dT primer with an attached linker sequence. We identified several 3'-ends at −1037, −1807, and −1846 bp. While the 3'-end at −1037 bp is consistent with the sequence for EST AA714549 (FIG. 2B, 3'-RACE), examination of the genomic sequence indicated a poly-A stretch in the antisense orientation at −1040 bp, suggesting that this 3'-end and EST AA714549 are artifacts of oligo-dT cDNA generation. The −1807 and −1846 bp 3'-ends did not correspond to A-rich genomic sequence, indicating that these RACE products represent real 3'-ends of the transcript (FIG. 2B, 3'-RACE). In addition to these two polyadenylation regions, strand-specific RT-PCR indicated that at least some transcripts extend farther to −2490 (FIG. 2A and FIG. 6). Although a consensus polyadenylation site is present at −2463, this site has not been validated by 3'-RACE.

Identification of the 5'-Ends of ASFMR1

Figure 5:
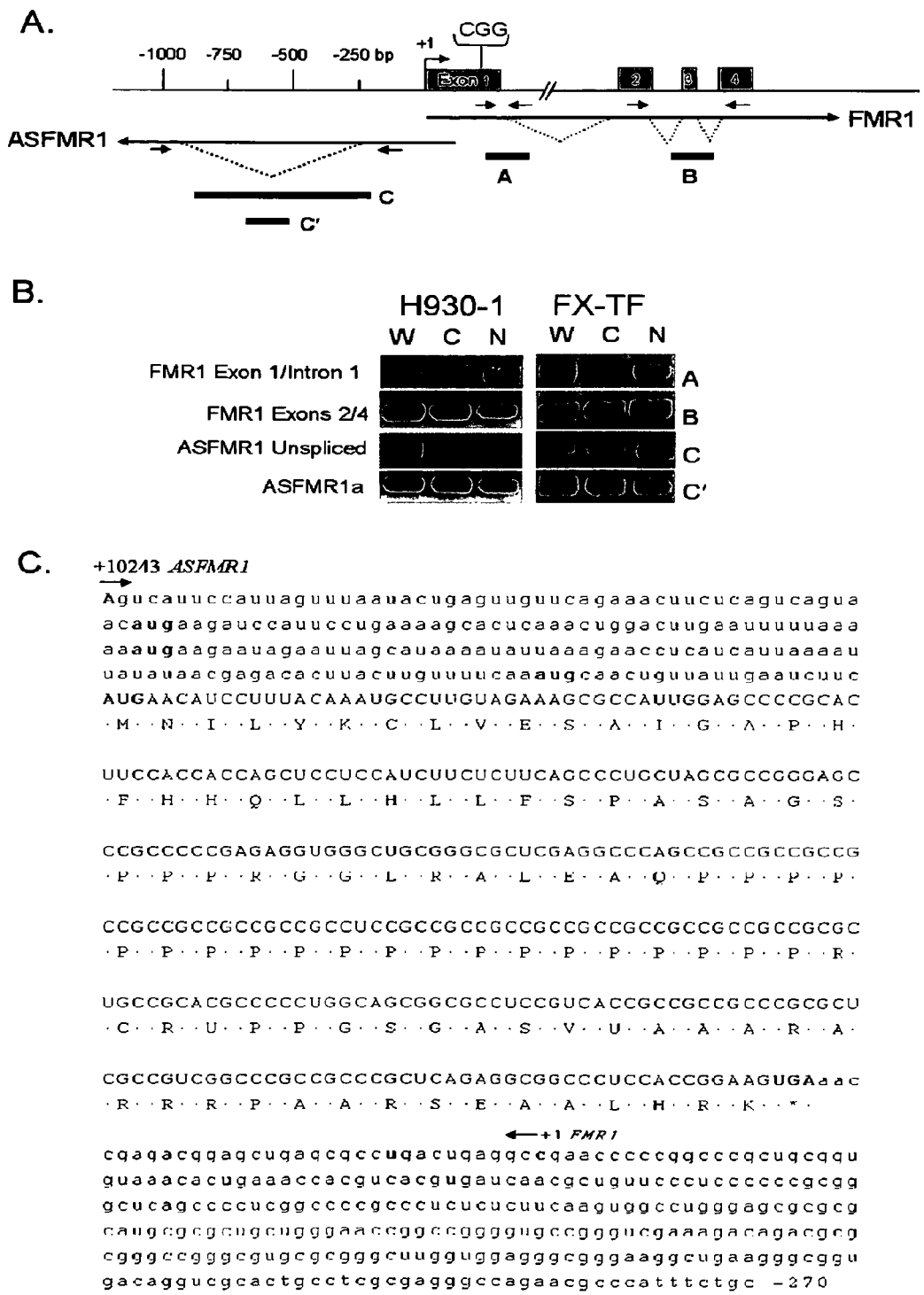
FIGS. 5A-C. The ASFMR1 transcript is transported to the cytoplasm and contains a putative ORF. (A) Diagram of the FMR1 locus depicting ASFMR1 and exons 1 to 4 of FMR1. Spliced ASFMR1 and FMR1 transcripts are shown with dotted lines. PCR primer sets used for analysis are indicated as small black arrows, while the bars A, B, C and C' demonstrate PCR products. (B) Semi-quantitative RT-PCR analysis of RNA isolated from whole cells (W), cytoplasmic fraction (C), and nuclear fraction (N). Amplification with the primer sets to FMR1, exon 1/intron 1 (unspliced, panel A) and exons 2/4 (spliced, panel B), and to ASFMR1, −1000F/−196R (unspliced, panels C, and spliced, panel C'), showed that similar to FMR1, the unspliced ASFMR1 transcript is enriched in the nucleus, while the spliced ASFMR1 transcript is evenly distributed between the cytoplasm and nucleus of both normal, H930-1, and premutation, FX-TF, cells. (C) The ASFMR1 transcript sequence (SEQ ID NO:9) depicting the amino acid sequence (SEQ ID NO:6) for the ORF encoding a polyproline peptide is shown. The ASFMR1 and FMR1 transcription initiation sites are indicated with arrows.

To identify the 5'-end of the ASFMR1 transcript, we performed 5'-RLM-RACE using two different approaches. We took advantage of an important feature of 5'-RLM-RACE that allows for the ligation of an RNA oligo to full-length capped transcripts, but not truncated or non-mRNA transcripts, and, in a separate analysis, we modified the 5'-RLM-RACE technique to allow detection of predominately uncapped transcripts. Accordingly, we identified three distinct regions of 5'-ends at +10243 bp, at +305 bp, and clustered at −99 to −208 bp, relative to FMR1 (FIG. 2B, 5'-RLM-RACE). The +10243 and −99 to −208 5'-ends were detected by RLM-RACE enriched for capped transcripts, whereas the +305 bp 5'-end was preferentially identified by the "uncapped" RACE, suggesting that it might be secondary to RNA cleavage or processing. This is consistent with the identification of an approximately 100-150 nt-sized fragment using northern blot analysis for short processed RNA fragments with a probe from +205 to +295 corresponding to the antisense sequence (data not shown). It is also important to note that the +10243 5'-end of the ASFMR1 transcript was identified in both normal and premutation lymphoblastoid cells, H930-1 and FX-TF, respectively, whereas the −99 to −208 cluster of 5'-ends was detected only in normal cells, H930-1, suggesting that similar to FMR1 (27), repeat expansion may be accompanied by the shift in the transcription start site usage by ASFMR1. Both regions of 5'-ends were identified in normal human brain tissue. Together, these data suggest the presence of two alternative promoters driving transcription of ASFMR1.

The −99 to −208 putative promoter has multiple transcription initiation sites identified by 5'-RLM-RACE, which is consistent with GC-rich, TATA-less promoters (FIG. 2C), which overlaps the FMR1 promoter and is consistent with the transcription start site reported for the mouse antisense transcript, AK148387. The +10243 putative promoter appears to have multiple basal promoter elements, including an upstream weak TATA box (29) and overlapping canonical Initiator elements with downstream promoter elements (FIG. 2D). The transcript initiated at +10243 spans the FMR1 CGG repeat in the CCG orientation and contains a 9.7 kb intron corresponding to the FMR1 intron (FIG. 2A and B) that uses the same splice donor and acceptor as FMR1 (FIG. 7). Using strand-specific RT-PCR, we confirmed that the ASFMR1 transcript initiated at +10243 is expressed in normal and premutation cell lines, but not full mutation (FIG. 1F and FIG. 6). Interestingly, in premutation cells, both 5'-RACE and strand-specific RT-PCR identified another splice form of the ASFMR1 transcript with a small intron from +10155 to +10070 (FIG. 7). This splice form was not present in normal cells (FIG. 1F and FIG. 6).

CTCF Binding Sites Flank the CGG Repeat

Figure 8:
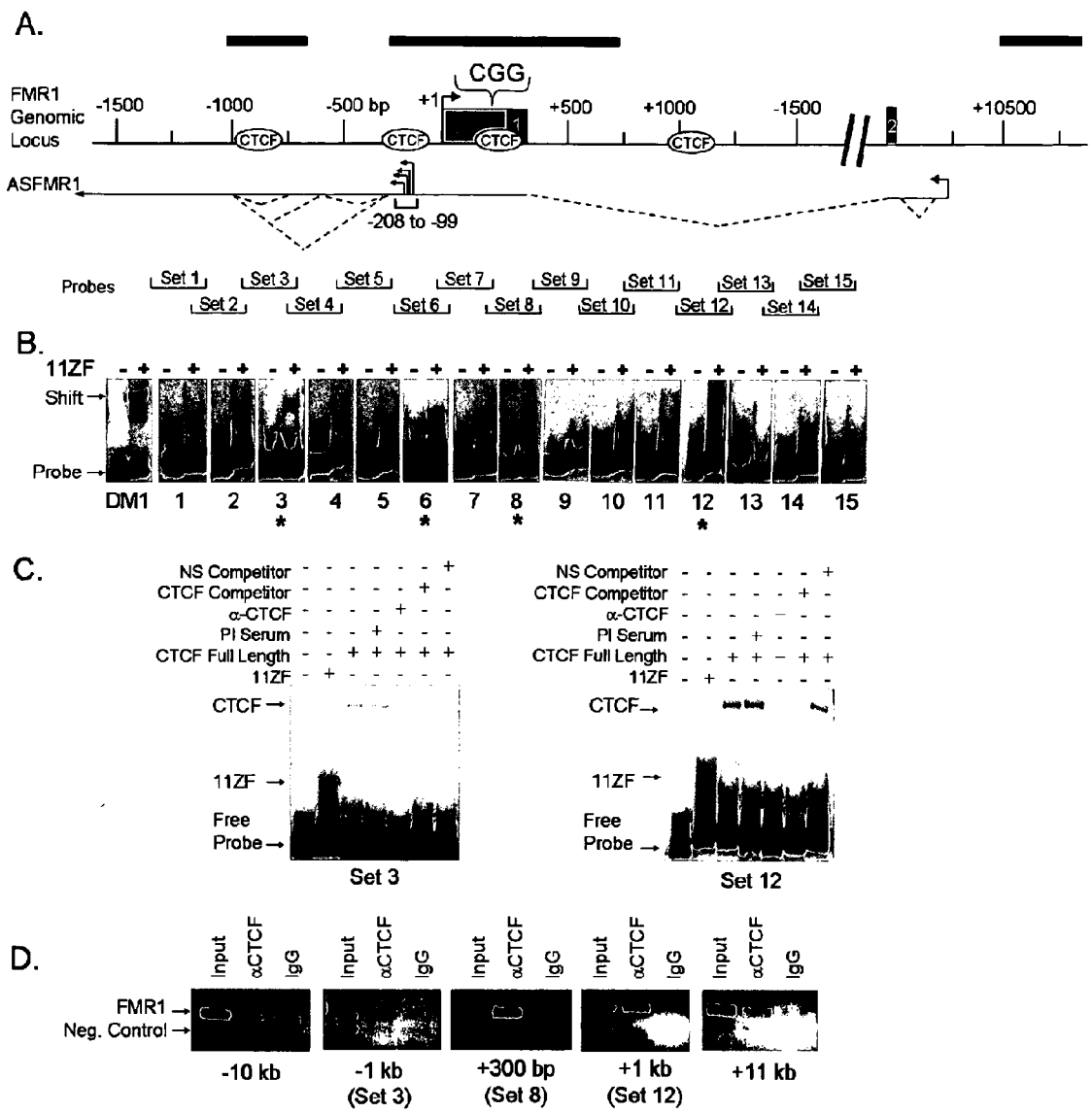
FIGS. 8A-D. CTCF-binding sites flank CGG repeat at the FMR1 locus. (A) Diagram of 15 overlapping DNA probes used in EMSA relative to the FMR1 genomic locus. CTCF binding sites identified by EMSA are depicted as ovals, while the CTCF peaks identified by ChIP-Seq (33) are indicated as black bars above the genomic locus. (B) EMSA with in vitro translated CTCF-DNA binding domain (11ZF). Each probe, including DM1 control, is shown without (−) and with (+) 11ZF. Horizontal arrows indicate free probe and mobility shift for DM1 control. Asterisks denote probes, which shifted when incubated with 11ZF protein. (C) EMSA using probe sets 3 and 12 with in vitro translated full length CTCF. Horizontal arrows indicate free probe, mobility shift for 11ZF control, as well as mobility shift for the full length CTCF. Incubation with CTCF-specific and non-specific antibodies or competitors is indicated by +/− above each lane. (D) Chromatin immunoprecipitation (ChIP) assay confirmed that CTCF binds to the human FMR1 locus in vivo. ChIP was performed with anti-CTCF antibody (Upstate Biotech) on the human lymphoblastoid cell line, H930-1, and subjected to semi-quantitative multiplex PCR analysis using primer pairs for FMR1 (upper band) and KIAA522 (lower band), as a negative control previously described (50). FMR1 locus was amplified at the position −10134 to −9895 (−10 kb), −1000 to −738 (−1000), +210 to −426 (+300), +950 to +1232 (+1000), and +10924 to +11184 (+11 kb) relative to the FMR1 transcriptional start site. All FMR1 amplicons, except the −10 kb region, showed enrichment for CTCF binding, indicating that CTCF binding sites flank the CGG repeat and the +10243 promoter of ASFMR1.

To map the location of CTCF binding sites (30, 31), which are associated with other triplet repeat loci (24, 32), we used a contiguous set of 15 overlapping DNA probes for electrophoretic mobility shift assay (EMSA) (Supplementary FIG. 3A) with in vitro translated 11ZF, a truncated version of the CTCF protein containing the zinc finger DNA binding domain. Four CTCF binding sites were identified by EMSA (FIG. 2A and FIG. 8B and C) and confirmed by chromatin immunoprecipitation (ChIP) (FIG. 8D). The identified CTCF binding sites flanking the CGG repeat region and the +10243 promoter region are consistent with the peaks of CTCF binding identified in a recent whole genome analysis (depicted in FIG. 8A) (33). Together, these results suggest that CTCF might have a role in regulating FMR1 and ASFMR1 transcription or regional chromatin loop formation (31).

ASFMR1 is Subject to X Chromosome Inactivation

Analysis of the previously characterized human:hamster somatic cell X hybrids (34) revealed that ASFMR1 is exclusively transcribed from the active X chromosome and is subject to X-inactivation (FIG. 3A). Our observation that the ASFMR1 transcript is not expressed by cells containing a full mutation CGG repeat expansion, suggested that cytosine methylation is an important factor in the transcriptional silencing of ASFMR1. To determine if ASFMR1 expression can be reactivated by treatment with 5-azaC, an inhibitor to cytosine methyltransferases, we analyzed a hybrid cell line, which was derived by 5azaC treatment of the inactive X chromosome hybrid and then clonally selected for HPRT expression (34). Consistent with published results, this cell line continued to express XIST, and demonstrated reactivation of HPRT and FMR1 (FIG. 3A). Furthermore, ASFMR1 expression was also reactivated, supporting the hypothesis that cytosine methylation plays a similar role in the transcriptional regulation of FMR1 and ASFMR1.

ASFMR1 is Widely Expressed in Human Tissues with Relatively High Expression in Brain To determine the pattern of ASFMR1 expression relative to FMR1 expression in human tissues, we performed semi-quantitative multiplex RT-PCR using a commercially derived RNA survey panel of twenty different human tissues (Ambion) (FIG. 3B). Under the same PCR conditions, we observed that FMR1 expression levels vary from relative high abundance in tissues like brain, kidney, ovary, testes, and thyroid to barely detectable levels in skeletal muscle (FIG. 3B, lanes 3, 8, 11, 14, 17, and 19) consistent with the previous report (35). When we compare ASFMR1 expression to FMR1, we see that ASFMR1 is expressed in all of the tissues examined, with relatively high expression in brain and kidney (FIG. 3B, lanes 3 and 8) and barely detectable in heart, placenta, prostate, skeletal muscle, thyroid, and trachea (FIG. 3B, lanes 7, 12-14, 19 and 20). Real time PCR analysis confirmed that expression of ASFMR1 normalized to FMR1 is consistently higher in brain than in other tissues: 5.6±1.5 times higher than in colon (p=1.6E-07), 6.4±1.1 times higher than in kidney (p=1.0E-08), and 46.5±12.5 times higher than in heart (p=6.1E-10). This expression profile suggests a potential role for ASFMR1 in the neurological phenotype of both FXTAS and FXS.

Effect of CGG Repeat Expansion on ASFMR1 Expression and Alternative Splicing

Figure 4:
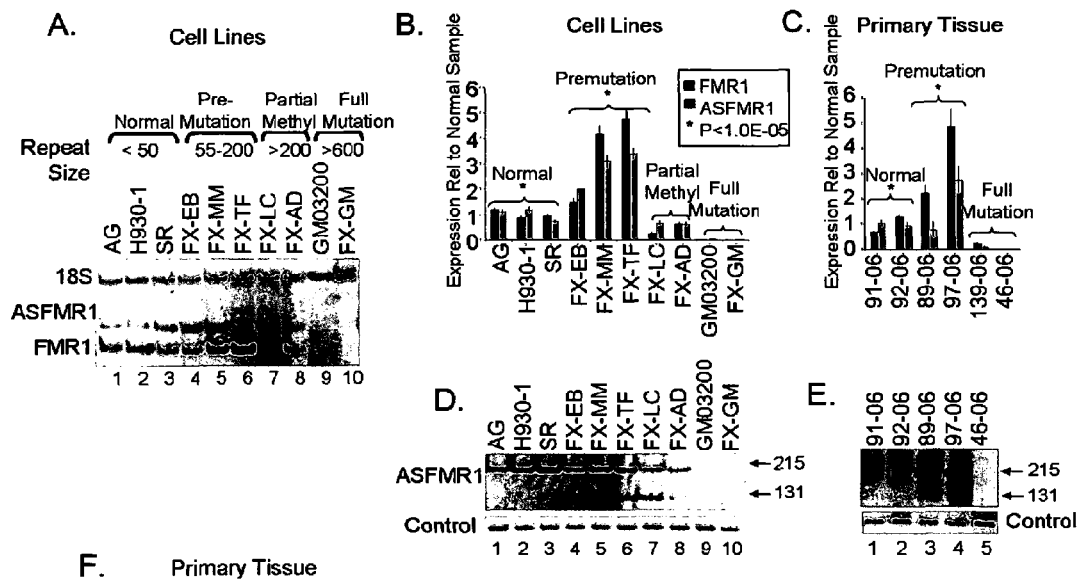
FIGS. 4A-F. Effect of CGG repeat expansion on ASFMR1 expression and alternative splicing. (A) Semi-quantitative multiplex RT-PCR analysis of human lymphoblastoid cell lines with characterized CGG repeats. (B) and (C) Real time RT-PCR analysis of the lymphoblastoid cell lines and the peripheral blood leukocytes from individuals with characterized CGG repeats indicated as cell lines and primary tissue respectively showed that, similar to FMR1, ASFMR1 is upregulated in individuals with premutation alleles relative to normal and is not expressed from full mutation alleles. Semi-quantitative RT-PCR and Real time RT-PCR analyses of ASFMR1 expression were performed with the primers sets to −1427/−1168 and to −1427/−1185, respectively, that allow identification of the spliced and unspliced forms of the ASFMR1 transcripts initiated at both putative promoters. Black and gray bars indicate FMR1 and ASFMR1 expression, respectively. Expression levels for FMR1 and ASFMR1 relative to the average of the normal samples and the corresponding P-values are summarized in Table 1. (D), (E), and (F) RT-PCR analysis of the human lymphoblastoid cell lines and the peripheral blood leukocytes for the presence of the alternative splice form of the ASFMR1 transcript using primers to +10028 and +10243 relative to FMR1. For primary tissues depicted in (F), normal alleles range from 23 to 54 CGGs, and premutation alleles range from 64 to 124 CGGs.

It has been well documented that FMR1 expression increases with increasing CGG repeat length in the premutation range (11, 12). To determine the effect of CGG repeat expansion on the expression levels of the ASFMR1 gene, we performed semi-quantitative multiplex RT-PCR (FIG. 4A) and real time RT-PCR analyses (FIG. 4B) of the human lymphoblastoid cell lines derived from individuals with characterized CGG repeat expansions (Table 1). Similar to FMR1, ASFMR1 expression increases as the CGG repeats expand within the premutation range (p<1.0E-05). While FMR1 and ASFMR1 expression levels are reduced in the partially methylated cell lines (p<0.003), neither FMR1 nor ASFMR1 expression is seen in the full mutation cell lines (p<1.2E-10) (FIG. 4B). Analysis of RNA isolated from the peripheral blood leukocytes of six individuals with characterized CGG repeats (Table 1) showed that ASFMR1 expression in primary tissue is consistent with the expression profile observed in lymphoblastoid cell lines. The premutation sample 97-06, with 122 CGG repeats, demonstrated significantly increased transcript levels of both FMR1 and ASFMR1 genes compared to the normal samples (Table 1) (FIG. 4C), whereas very little to no expression of FMR1 and ASFMR1 was found in individuals with hypermethylated full mutation alleles, 139-06 and 46-06. Interestingly, FMR1 expression level increases slightly, but not ASFMR1, for premutation sample 89-06, carrying an allele of 102 CGG repeats (FIG. 4C).

It is important to note that the PCR primers used to quantify the ASFMR1 expression levels by both semi-quantitative and real time RT-PCR (shown in FIG. 4) detected the ASFMR1 transcripts initiated at both putative promoters: the −99 to −208 promoter and the +10243 promoter. Further analysis of multiple regions of the ASFMR1 transcript by semi-quantitative strand-specific RT-PCR (FIG. 6) demonstrated that, similar to the total levels of the ASFMR1 transcript, the transcript initiated at the +10243 promoter is also upregulated in premutation cells in comparison to normal. Together with the 5'RACE results that identified the +10243 site as a major transcriptional start site in the premutation cell line, FX-TF, this suggests that the increased ASFMR1 expression in premutation cells results in mutant transcripts containing expanded CCG repeats.

The ASFMR1 transcript with the splice site from +10155 to +10070 (FIG. 1F) was detected in cells with the premutation and partially methylated full mutation alleles, but not in cells with normal or hypermethylated full mutation alleles (FIGS. 4D and 4E). Notably, the premutation sample 89-06 with 102 repeats and lower ASFMR1 expression demonstrated lower levels of expression of this splice form relative to the unspliced transcript (FIG. 4C). Moreover, the spliced transcript was not present in the premutation cells FX-EB carrying the shortest premutation sized allele of 82 CGG repeats (FIGS. 4A and B), suggesting that CGG repeat expansion may influence ASFMR1 transcript processing and/or its stability. Analysis of a larger collection of RNA samples isolated from the peripheral blood leukocytes of 11 individuals with normal alleles and 12 individuals with premutation alleles confirmed that this splice form is specific to the premutation allele (FIG. 4F).

The ASFMR1 Transcript is Transported to the Cytoplasm and Contains a Polyproline ORF To determine whether the ASFMR1 transcript is retained in the nucleus or transported to the cytoplasm, we analyzed the cytosolic and nuclear fractions of normal H930-1 and premutation FX-TF cell lines for the presence of unprocessed and spliced ASFMR1 transcripts. Similar to FMR1 used as a control transcript, the unspliced ASFMR1 transcript was enriched in the nucleus, while the spliced transcript was evenly distributed between the cytoplasm and nucleus of H930-1 and FX-TF cells (FIGS. 5A and B). This indicates that after processing in the nucleus, the mature ASFMR1 transcript is exported to the cytoplasm. In addition, no differences were detected in the cellular localization of either the ASFMR1 or FMR1 transcripts between cells with normal or premutation sized CGG repeat regions.

Analysis of both the unspliced and spliced ASFMR1 transcripts for the presence of putative open reading frames (ORFs) identified an ORF encoding a polyproline peptide. This ORF is found in the transcript initiated from +10243. The stretch of proline is a consequence of the repeat, which is CCG with interspersed CCU for ASFMR1 (FIG. 5C). Both CCG and CCU code for proline, thus the ORF encodes for a polyproline peptide whether or not AGG•CCU interspersion is lost during CGG•CCG repeat expansion. Accordingly, CGG expansion would result in an even longer polyproline stretch. The entire ORF for the putative protein is contained in the region of the ASFMR1 transcript that overlaps FMR1. Interestingly, there are several potential translational start sites located upstream of this ORF, which could interfere with translation of the polyproline peptide. In this context it is important to note that the small splice site from +10155 to +10070 identified in the premutation cells (FIGS. 1E and 4D-E) would remove one of the potentially interfering upstream AUGs associated with the stronger Kozak sequence and therefore likely enhance translation of the polyproline peptide.

Asfmr1 is Present in Mouse

Strand-specific RT-PCR analysis identified two regions of the antisense transcription at the murine Fmr1 locus: at the position −156 to −379 bp, relative to the Fmr1 transcriptional start site, that is consistent with the previously reported murine antisense transcript AK148387, and at the position +204 to +312 bp, overlapping first coding exon of Fmr1 (FIG. 9). Together, these observations suggest that similar to the human FMR1 locus, there is an antisense transcript Asfmr1 spanning the CGG-rich region of murine Fmr1. Moreover, similar to ASFMR1, Asfmr1 contains a potential proline-rich ORF, conserved between human and mouse.

In this study, it has been shown that ASFMR1 is transcribed in the antisense orientation to FMR1. The ASFMR1 transcript is alternatively spliced, polyadenylated, and exported to the cytoplasm. ASFMR1 transcription appears to be driven by two alternative promoters: the FMR1 bidirectional promoter and the promoter located in the second intron of FMR1. The transcript initiated at the latter promoter spans the CGG repeat of the FMR1 gene in the CCG orientation, exhibits premutation-specific alternative splicing, and contains an open reading frame with the CCG repeat encoding a polyproline peptide. Similar to FMR1, the ASFMR1 transcript is silenced in full-mutation individuals and up-regulated in carriers of premutation alleles, suggesting that, in addition to FMR1, ASFMR1 might be involved in the pathogenesis of FXTAS and FXS. Consistent with the neurological phenotypes of both FXTAS and FXS, ASFMR1 exhibits relatively high expression levels in human brain. An antisense transcript has also been identified in the mouse that overlaps the murine FMR1 gene and has a potential proline-rich ORF, suggesting a conserved cellular function for ASFMR1. Taken together these findings strongly suggest that ASFMR1 expression from the expanded allele could contribute to the variable clinical phenotypes associated with the CGG repeat expansion by either an RNA and/or protein mediated mechanism.

Further Characterization of ASFMR1.

Expression of the antisense transcript at the FMR1 locus, ASFMR1, in normal and premutation alleles but not in full mutations. The transcript is spliced, poly-adenylated, transported to the cytoplasm, and contains an ORF with a polyproline stretch encoded by the CCG repeat. Notably, the splice form of the ASFMR1 transcript with a small intron from +10155 to +10070 identified in premutation cells was proposed to enhance translation of the polyproline peptide (Ladd et al, *Hum Mol Gen,* 2007, 16, 3174-87).

ASFMR1 Transcript is Associated with Polysomes.

To determine whether ASFMR1 can be translated to protein, RNA from the mouse brain polysome gradient was tested for the presence of the ASFMR1 transcript. FMR1 and H19, a known non-coding transcript, were used as a positive and negative control, respectively. Similar to FMR1, the ASFMR1 transcript was predominantly detected in fractions 5 though 8, indicating its association with polysomes.

ASFMR1 Polyproline ORF can be Translated to Protein Both in vitro and in vivo.

To test whether the ASFMR1 protein can be expressed in mammalian cells, the ASFMR1 transcript containing the endogenous transcriptional start site identified by 5'-RLM RACE at +10243, with and without premutation specific splice, from +10155 to +10070, was cloned into a pcDNA3.1 expression vector with the V5/His tags in frame with the ASFMR1 polyProline ORF (FIG. 10A, TS-Unspliced and TS-Spliced). For a positive control, the native Kozak sequence, TCC, was replaced with an optimal Kozak, ACC (FIG. 10A, pPro-ACC), whereas a frame shift mutation was used as a negative control (FIG. 10B, F2). In addition to the CMV promoter, the expression constructs contain a bacterial T7 promoter, which allows ASFMR1 expression in an in vitro system, providing a means for protein expression without co- and/or post-translational modifications. In vitro translated ASFMR1 protein produced a single band on an SDS gel corresponding to ~25 kDa (FIG. 10B). The protein constructs were also transfected into 293 cells, and cells were harvested at 24, 48 and 72 hours after transfection to determine optimal protein expression.

Both the positive control with the optimal Kozak sequence (ACC) and the premutation-specific splice form of ASFMR1 (TS-S) produced a polyproline peptide detected by either anti-V5 or anti-His antibodies (three specific bands between 19 and 25 kDa) with the maximum level of expression at 48 hours after transfection (FIG. 10C). The unspliced ASFMR1 transcript (TS-U), as well as the frame shift negative control (F2), did not yield any protein (FIG. 10C). RT-PCR analysis of the transfected cells showed efficient transcription from all the expression constructs used, including TS-U and F2, suggesting that the premutation specific splice at +10155 to +10070 removes one of the interfering upstream ORFs (uORF) and therefore may facilitate translation of the polyproline peptide. Taken together these findings indicate that in premutation cells, ASFMR1 may translate to protein containing polyproline expansions and therefore, may be pathogenic at both RNA and protein levels (CCG and polyproline expansions, respectively). In this context it is important to note that several attempts to stably express ASFMR1 in cells have failed, perhaps due to the ASFMR1 toxicity.

To determine the functional consequences of the mutant ASFMR1 RNA and protein expression, tagged clones with increasing CGG•CCG repeat expansions will be generated. It has been demonstrated that premutation CGG-repeat RNA contributes to the formation of intranuclear inclusions and disruption of lamin A/C in human cultured fibroblasts and neuronal cells. In a similar system, studies will be conducted to address whether the expanded CCG repeats contribute to the inclusion formation at the DNA, RNA, and/or protein level. In addition to the V5/His-tag protein expression constructs described above, GFP-fusion constructs will be made, in which the V5/His-tags are exchanged for GFP, which will provide a method to sort transfected cells and thus enrich for cells that are capable of inclusion formation. In these experiments, alterations in gene expression and effects on neuronal cell differentiation will be assessed. In addition to wild type cells, the abundance of the ASFMR1 RNA and protein in a full mutation cell line without expression of ASFMR1 and in premutation cells with elevated levels of ASFMR1 will be modulated, using forced expression and siRNA approaches, respectively.

To study in vivo expression of the ASFMR1 protein and to test whether it is present in intranuclear inclusions of FXTAS patients, ASFMR1 protein-specific antibodies will be generated according to standard protocols. ASFMR1 GST-fusion proteins (full length and truncated version without a polyProline stretch) will also be produced.

In summary, the present invention provides the identification of ASFMR1, an antisense transcript at the FMR1 locus, that could contribute to the pathogenesis of FXS and FXTAS either through an RNA and/or protein mediated mechanism.

The foregoing is illustrative of the present invention, and is not to be construed as limiting thereof. The invention is defined by the following claims, with equivalents of the claims to be included therein. All publications, patent applications, patents, patent publications, sequences (nucleotide sequences, single polymorphism nucleotides, amino acid sequences, etc.) identified in the GenBank® database or other sequence databases according to the accession numbers provided herein, and any other references cited herein are incorporated by reference in their entireties for the teachings relevant to the sentence and/or paragraph in which the reference is presented.

REFERENCE LIST

1. Neri, G. and Chiurazzi, P. (1999) X-linked mental retardation (Review). *Adv. Genet.,* 41, 55-94.
2. O'Donnell, W. T. and Warren, S. T. (2002) A decade of molecular studies of fragile X syndrome (Review). *Annu. Rev. Neurosci.,* 25, 315-338.
3. Hagerman, P. J. and Hagerman, R. J. (2004) The fragile-X premutation: a maturing perspective. *Am. J. Hum. Genet.,* 74, 805-816.
4. Willemsen, R., Mientjes, E. and Oostra, B. A. (2005) FXTAS: a progressive neurologic syndrome associated with Fragile X premutation (Review). *Curr. Neurol. Neurosci. Rep.,* 5, 405-410.
5. Oostra, B. A. and Willemsen, R. (2003) A fragile balance: FMR1 expression levels. *Hum. Mol. Genet.,* 12, R249-257.
6. Hansen, R. S., Garner, S. M., Scott, C. R., Chen, S. H. and Laird, C. D. (1992) Methylation analysis of CGG sites in the CpG island of the human FMR1 gene. *Hum. Mol. Genet.,* 1, 571-578.
7. Stoger, R., Kajimura, T. M., Brown, W. T. and Laird, C. D. (1997) Epigenetic variation illustrated by DNA methylation patterns of the fragile-X gene FMR1. *Hum. Mol. Genet.,* 6, 1791-1801.
8. Dombrowski, C., Levesque, S., Morel, M. L., Rouillard, P., Morgan, K. and Rousseau, F. (2002) Premutation and intermediate-size FMR1 alleles in 10572 males from the general population: loss of an AGG interruption is a late event in the generation of fragile X syndrome alleles. *Hum. Mol. Genet.,* 11, 371-378.
9. Jacquemont, S., Hagerman, R. J., Leehey, M. A., Hall, D. A., Levine, R. A., Brunberg, J. A., Zhang, L., Jardini, T., Gane, L. W., Harris, S. W. et al. (2004) Penetrance of the fragile X-associated tremor/ataxia syndrome in a premutation carrier population. *JAMA,* 291, 460-469.
10. Tassone, F., Beilina, A., Carosi, C., Albertosi, S., Bagni, C., Li, L., Glover, K., Bentley, D. and Hagerman, P. J. (2007) Elevated FMR1 mRNA in premutation carriers is due to increased transcription. *RNA,* 13, 555-562.
11. Kenneson, A., Zhang, F., Hagedorn, C. J., & Warren, S. T. (2001) Reduced FMRP and increased FMR1 transcription is proportionally associated with CGG repeat number in intermediate-length and premutation carriers. *Hum. Mol. Genet.,* 10, 1449-1454.
12. Tassone, F., Hagerman, R. J., Taylor, A. K., Gane, L. W., Godfrey, T. E. and Hagerman, P. J. (2000) Elevated levels of FMR1 mRNA in carrier males: A new mechanism of involvement in fragile X syndrome. *Am. J. Hum. Gen.,* 66, 6-15.
13. Primerano, B., Tassone, F., Hagerman, R. J., Hagerman, P., Amaldi, F., & Bagni, C. (2002) Reduced FMR1 mRNA translation efficiency in fragile x patients with premutations. *RNA,* 8, 1482-1488.
14. Iwahashi, C. K., Yasui, D. H., An, H. J., Greco, C. M., Tassone, F., Nannen, K., Babineau, B., Lebrilla, C. B., Hagerman, R. J. and Hagerman, P. J. (2006) Protein composition of the intranuclear inclusions of FXTAS. *Brain,* 129, 256-271.
15. Tassone, F., Iwashashi, C. and Hagerman, P. J. (2004) FMR1 RNA within the intranuclear inclusions of fragile X-associated tremor/ataxia syndrome (FXTAS). *RNA Biol.,* 1, 103-105.
16. Greco, C., Hagerman, R. J., Tassone, F., Chudley, A., Del Bigio, M. R., Jacquemont, S., Leehey, M., & Hagerman, P. J. (2002) Neuronal intranuclear inclusions in a new cerebellar tremor/ataxia syndrome among fragile X carriers. *Brain,* 125, 1760-1771.
17. Greco, C. M., Berman, R. F., Martin, R. M., Tassone, F., Schwartz, P. H., Chang, A., Trapp, B. D., Iwahashi, C., Brunberg, J., Grigsby, J. et al. (2006) Neuropathology of fragile X-associated tremor/ataxia syndrome (FXTAS). *Brain*, 129, 243-255.
18. Ranum, L. P., Cooper, T. A. (2006) RNA-mediated neuromuscular disorders. *Annu. Rev. Neurosci.*, 29, 259-277.
19. Tapscott, S. J. (2000) Deconstructing myotonic dystrophy. *Science*, 289, 1701-1702.
20. Lugenbeel, K. A., Peier, A. M., Carson, N. L., Chudley, A. E. and Nelson, D. L. (1995) Intragenic loss of function mutations demonstrate the primary role of FMR1 in fragile X syndrome. *Nat. Genet.*, 10, 483-485.
21. Meijer, H., de Graaff, E., Merckx, D. M., Jongbloed, R. J., de Die-Smulders, C. E., Engelen, J. J., Fryns, J. P., Curfs, P. M. and Oostra, B. A. (1994) A deletion of 1.6 kb proximal to the CGG repeat of the FMR1 gene causes the clinical phenotype of the fragile X syndrome. *Hum. Mol. Genet.*, 3, 615-620.
22. Chiurazzi, P., de Graaff, E., Ng, J., Verkerk, A.J., Wolfson, S., Fisch, G. S., Kozak, L., Neri, G. and Oostra, B. (1994) No apparent involvement of the FMR1 gene in five patients with phenotypic manifestations of the fragile X syndrome. *Am. J. Med. Genet.*, 51, 309-314.
23. Reyniers, E., Wolff, G., Tariverdian, G., De Boulle, K., Storm, K., Kooy, R. F. and Willems, P. J. (1996) Severe mental retardation and macroorchidism without mutation in the FMR1 gene (Review). *Am. J. Med. Genet.*, 64, 408-412.
24. Cho, D. H., Thienes, C. P., Mahoney, S. E., Analau, E., Filippova, G. N. and Tapscott, S. J. (2005) Antisense transcription and heterochromatin at the DM1 CTG repeats are constrained by CTCF. *Mol. Cell*, 20, 483-489.
25. Moseley, M. L., Zu, T., Ikeda, Y., Gao, W., Mosemiller, A. K., Daughters, R. S., Chen, G., Weatherspoon, M. R., Clark, H. B., Ebner, T. J. et al. (2006) Bidirectional expression of CUG and CAG expansion transcripts and intranuclear polyglutamine inclusions in spinocerebellar ataxia type 8. *Nat. Genet.*, 38, 758-769.
26. Drouin, R., Angers, M., Dallaire, N., Rose, T. M., Khandjian, E. W. and Rousseau, F. (1997) Structural and functional characterization of the human FMR1 promoter reveals similarities with the hnRNP-A2 promoter region. *Hum. Mol. Genet.*, 6, 2051-2060.
27. Beilina, A., Tassone, F., Schwartz, P. H., Sahota, P. and Hagerman, P. J. (2004) Redistribution of transcription start sites within the FMR1 promoter region with expansion of the downstream CGG-repeat element. *Hum. Mol. Genet.*, 13, 543-549.
28. Saluto, A., Brussino, A., Tassone, F., Arduino, C., Cagnoli, C., Pappi, P., Hagerman, P., Migone, N. and Brusco, A. (2005) An enhanced polymerase chain reaction assay to detect pre- and full mutation alleles of the fragile X mental retardation 1 gene. *J. Mol. Diagn.*, 7, 605-612.
29. Meyer, T., Carlstedt-Duke, J. and Starr, D. B. (1997) A weak TATA box is a prerequisite for glucocorticoid-dependent repression of the osteocalcin gene. *J. Biol. Chem.*, 272, 30709-30714.
30. Bell, A. C., West, A. G. and Felsenfeld, G. (2001) Insulators and boundaries: versatile regulatory elements in the eukaryotic genome (Review). *Science*, 291, 447-450.
31. Filippova, G. N. (2007) Genetics and Epigenetics of the Mulitfunctional Protein CTCF. *Curr. Top. Dev. Bio.*, 80, 337-362.
32. Filippova, G. N., Thienes, C. P., Penn, B. H., Cho, D. H., Hu, Y. J., Moore, J. M., Klesert, T. R., Lobanenkov, V. V. and Tapscott, S. J. (2001) CTCF-binding sites flank CTG/CAG repeats and form a methylation-sensitive insulator at the DM1 locus. *Nat. Genet.*, 28, 335-343.
33. Barski, A., Cuddapah, S., Cui, K., Roh, T. Y., Schones, D. E., Wang, Z., Wei, G., Chepelev, I. and Zhao, K. (2007) High-resolution profiling of histone methylations in the human genome. *Cell*, 129, 823-837.
34. Hansen, R. S., Canfield, T. K., Fjeld, A. D. and Gartler, S. M. (1996) Role of late replication timing in the silencing of X-linked genes. *Hum. Mol. Genet.*, 5, 1345-1353.
35. Hinds, H. L., Ashley, C. T., Sutcliffe, J. S., Nelson, D. L., Warren, S. T., Housman, D. E. and Schalling, M. (1993) Tissue specific expression of FMR-1 provides evidence for a functional role in fragile X syndrome. *Nat. Genet.*, 3, 36-43.
36. Arocena, D. G., Iwahashi, C. K., Won, N., Beilina, A., Ludwig, A. L. T., F., Schwartz, P. H. and Hagerman, P. J. (2005) Induction of inclusion formation and disruption of lamin A/C structure by premutation CGG-repeat RNA in human cultured neural cells. *Hum. Mol. Genet.*, 14, 3661-3671.
37. Tassone, F., Hagerman, R. J., Garcia-Arocena, D., Khandjian, E. W., Greco, C. M. and Hagerman, P. J. (2004) Intranuclear inclusions in neural cells with premutation alleles in fragile X associated tremor/ataxia syndrome. *J. Med. Genet.*, 41, e43.
38. Fardaei, M., Rogers, M. T., Thorpe, H. M., Larkin, K., Hamshere, M. G., Harper, P. S., Brook, J. D. (2002) Three proteins, MBNL, MBLL and MBXL, co-localize in vivo with nuclear foci of expanded-repeat transcripts in DM1 and DM2 cells. *Hum. Mol. Genet.*, 11, 805-814.
39. Kino, Y., Mori, D., Oma, Y., Takeshita, Y., Sasagawa, N. and Ishiura, S. (2004) Muscleblind protein, MBNL1/EXP, binds specifically to CHHG repeats. *Hum. Mol. Genet.*, 13, 495-507.
40. Sofola, O. A., Jin, P., Botas, J. and Nelson, D. L. (2007) Argonaute-2 dependent rescue of a *Drosophila* model of FXTAS by FRAXE premutation repeat. *Hum. Mol. Genet.*
41. Zoghbi, H. Y. and Or, H. T. (2000) Glutamine repeats and neurodegeneration. *Annu. Rev. Neurosci.*, 23, 217-247.
42. Margolis, R. L., Holmes, S. E., Rosenblatt, A., Gourley, L., O'Hearn, E., Ross, C. A., Seltzer, W. K., Walker, R. H., Ashizawa, T., Rasmussen, A. et al. (2004) Huntington's Disease-like 2 (HDL2) in North America and Japan. *Ann. Neurol.*, 56, 670-674.
43. Martens, J. H., O'Sullivan, R. J., Braunschweig, U., Opravil, S., Radolf, M., Steinlein, P., Jenuwein, T. (2005) The profile of repeat-associated histone lysine methylation states in the mouse epigenome. *EMBO J.*, 24, 800-812.
44. Grewal, S. I. and Jia, S. (2007) Heterochromatin revisted. *Nat. Rev. Genet.*, 8, 35-46.
45. Talbert, P. B. and Henikoff, S. (2006) Spreading of silent chromatin: inaction at a distance. *Nat. Rev. Genet.*, 7, 793-803.
46. Handa, V., Saha, T. and Usdin, K. (2003) The fragile X syndrome repeats form RNA hairpins that do not activate the interferon-inducible protein kinase, PKR, but are cut by Dicer. *Nucleic Acids Res.*, 31, 6243-6248.
47. Krol, J., Fiszer, A., Mykowska, A., Sobczak, K., de Mezer, M. and Krzyzosiak, W. J. (2007) Ribonuclease dicer cleaves triplet repeat hairpins into shorter repeats that silence specific targets. *Mol. Cell*, 25, 575-586.
48. Napierala, M., Michalowski, D., de Mezer, M. and Krzyzosiak, W. J. (2005) Facile FMR1 mRNA structure regulation by interruptions in CGG repeats. *Nucleic Acids Res.*, 33, 451-463.
49. Nelson, J. D., Denisenko, O., Bomsztyk, K. (2006) Protocol for the fast chromatin immunoprecipitation (ChIP) method. *Nat. Protoc.*, 1.
50. Filippova, G. N., Cheng, M. K., Moore, J. M., Truong, J. P., Hu, Y. J., Nguyen, D. K., Tsuchiya, K. D., Disteche, C. M. (2005) Boundaries between chromosomal domains of X inactivation and escape bind CTCF and lack CpG methylation during early development. *Dev. Cell*, 8, 31-42.

TABLE 1

Patient Sample Summary*

| Cell Line | Gender | Repeat Size | Category | FMR1 Expression Mean ± s.e. | n | FMR1 P-value | ASFMR1 Expression Mean ± s.e. | n |
|---|---|---|---|---|---|---|---|---|
| AG | Female | 16/29 | Normal | 1.16 ± 0.06 | 6 | na | 1.07 ± 0.11 | 6 |
| H930-1 | Male | nd | Normal | 0.88 ± 0.08 | 6 | na | 1.17 ± 0.11 | 6 |
| SR | Male | nd | Normal | 0.95 ± 0.07 | 6 | na | 0.75 ± 0.06 | 6 |
| FX-EB | Male | 82 | Premutation | 1.51 ± 0.14 | 6 | 1.0E−02 | 2.03 ± 0.14 | 6 |
| FX-MM | Male | 170 | Premutation | 4.20 ± 0.34 | 6 | 1.5E−04 | 3.11 ± 0.26 | 6 |
| FX-TF | Male | 195 | Premutation | 4.80 ± 0.35 | 6 | 7.0E−05 | 3.41 ± 0.22 | 6 |
| FX-LC | Male | 250 | Partial | 0.28 ± 0.06 | 6 | 3.0E−10 | 0.68 ± 0.06 | 6 |
| FX-AD | Male | 293/950 | Partial | 0.64 ± 0.03 | 6 | 7.8E−06 | 0.65 ± 0.08 | 6 |
| GM03200 | Male | >600 | Full Mutation | 0 | 6 | 2.3E−13 | 0.02 ± 0.00 | 6 |
| FX-GM | Male | 610 | Full Mutation | 0 | 6 | 2.3E−13 | 0.03 ± 0.01 | 6 |
| Primary Cell | | | | | | | | |
| 91-06 | Male | 30 | Normal | 0.71 ± 0.04 | 12 | na | 1.04 ± 0.14 | 5 |
| 92-06 | Male | 30 | Normal | 1.32 ± 0.08 | 11 | na | 0.98 ± 0.11 | 11 |
| 89-06 | Male | 102 | Premutation | 2.25 ± 0.31 | 12 | 1.4E−03 | 0.81 ± 0.13 | 6 |
| 97-06 | Male | 122 | Premutation | 4.87 ± 0.69 | 12 | 1.1E−04 | 2.77 ± 0.53 | 6 |
| 139-06 | Male | 331/572/806 | Full Mutation | 0.25 ± 0.02 | 6 | 8.5E−10 | 0.12 ± 0.01 | 6 |
| 46-06 | Male | 271/662 | Full Mutation | 0 | 12 | 6.2E−08 | 0.02 ± 0.01 | 6 |

Expression levels for FMR1 and ASFMR1 relative to the average of the normal samples and the corresponding P-values were determined by real time RT-PCR.
Two repeat sizes are denoted for two alleles for normal female and multiple repeat sizes are indicated for mosaic male samples;
nd, not determined;
na, not applicable.

TABLE 2

Strand Specific RT-PCR Primers

| Numeric Name | | SEQ ID NO: |
|---|---|---|
| Linker | 5'-CGACTGGAGCACGAGGACACTGA-3' | 22 |
| −2485Forward | 5'-CGACTGGAGCACGAGGACACTGAgtactggcagtgaagataag-3' | 23 |
| −1000Forward | 5'-CGACTGGAGCACGAGGACACTGAcagtgtctggcacacgatagatgctc-3' | 24 |
| −274Reverse | 5'-ggtgcactcagtggcgtgggaaatc-3' | 25 |
| −196Reverse | 5'-ggtggagggcgggaaggctgaaggg-3' | 26 |
| +15Forward | 5'-CGACTGGAGCACGAGGACACTGAgctcagctccgtttcggttttcacttccggt-3 | 27 |
| +59Reverse | 5'-cagaggcggccctccaccggaagtg-3' | 28 |
| +210Forward | 5'-CGACTGGAGCACGAGGACACTGAcccgcagcccacctctcggggcg-3' | 29 |
| +295Reverse | 5'-agccccgcacttccaccaccagctcctcca-3' | 30 |
| +10028Forward | 5'-CGACTGGAGCACGAGGACACTGAaggatgttcatgaagattcaataag-3' | 31 |
| +10243Reverse | 5'-agcagaaacagtcattccattag-3' | 32 |

| Numeric Name | RACE Primers | |
|---|---|---|
| −1427F | 5'-catgtgactactccaaagaccctagtc-3' | 33 |
| −1383F | 5'-ttgctatggccttgaggaatgtg-3' | 34 |
| −1287F | 5'-ctctcacctgccatattccagctggaat-3' | 35 |
| −1172F | 5'-ggaagcgcctattcttcatac-3' | 36 |
| −1000F | 5'-cagtgtctggcacacgatagatgctc-3' | 37 |
| −965F | 5'-cgtcaacttctcagttggatac-3' | 38 |
| −566F | 5'-tctggtgagagagggcgtagacgcctc-3' | 49 |
| −551F | 5'-cctattctcgccttccactccacc-3' | 40 |
| −267F | 5'-gaaatgggcgttctggccctcgcg-3' | 41 |
| −255F | 5'-ctggccctcgcgaggcagtgcgac-3' | 42 |
| −207F | 5'-gccctccaccaagcccgcgcacg-3' | 43 |
| −87F | 5'-ccgaggggctgagcccgcgggg-3' | 44 |
| −57F | 5'-cagcgttgatcacgtgacgtgg-3' | 45 |
| +210F | 5'-cccgcagcccacctctcggggcg-3' | 46 |
| +234F | 5'-ggctcccggcgctagcagggctg-3' | 47 |
| +9873F | 5'-gtaaaggatgttcatgaagattc-3' | 48 |
| +9907F | 5'-gcatttgaaaacaagtaagtgtctcg-3' | 49 |
| −1815R | 5'-tcagtccctacagggtccttgttt-3' | 50 |
| −1168R | 5'-cttccatgatggcggaacatgacctagtc-3' | 51 |
| −1185R | 5'-catgacctagtctggggtg gag-3' | 52 |
| −1203R | 5'-ggagaaggggagatgattccagc-3' | 53 |
| −949R | 5'-gctggtatccaactgagaagttgacg-3' | 54 |
| −1058R | 5'-cg actgccagcattgaacttag-3' | 55 |
| −1075R | 5'-cttagtacctagcaaagtaggtg-3' | 56 |

TABLE 2-continued

Strand Specific RT-PCR Primers

| -738R | 5'-cacttgaggttcatttctgcccctactg-3' | 57 |

TABLE 2-continued

Strand Specific RT-PCR Primers

| -298R | 5'-caaatgcatccggttatcccag-3' | 58 |
| -274R | 5'-ggtgcactcagtggcgtgggaaatc-3' | 59 |

That which is claimed is:

1. A method of detecting an ASFMR1e mRNA transcript in a sample from a subject, comprising:
   a) obtaining a nucleic acid sample from the subject;
   b) assaying the nucleic acid sample for an ASFMR1e mRNA transcript having a cDNA sequence comprising the nucleotide sequence of SEQ ID NO:5; and
   c) detecting the ASFMR1e mRNA transcript in the sample.

2. A method of detecting the presence or absence of an ASFMR1e mRNA transcript having a cDNA sequence comprising the nucleotide sequence of SEQ ID NO:5 in a sample from a subject, comprising:
   a) obtaining a nucleic acid sample from the subject;
   b) contacting the nucleic acid sample with a primer pair consisting of a forward primer comprising the nucleotide sequence of SEQ ID NO:31 and a reverse primer comprising the nucleotide sequence of SEQ ID NO:32 or a primer pair consisting of a forward primer, comprising the nucleotide sequence of SEQ ID NO:29 and a reverse primer comprising the nucleotide sequence of SEQ ID NO:32, under conditions wherein nucleic acid amplification can occur; and
   c) analyzing an amplification product of step (b), thereby detecting the presence or absence of the ASFMR1e mRNA transcript in the sample.

* * * * *

UNITED STATES PATENT AND TRADEMARK OFFICE
CERTIFICATE OF CORRECTION

PATENT NO. : 8,597,880 B2
APPLICATION NO. : 12/681433
DATED : December 3, 2013
INVENTOR(S) : Tapscott et al.

It is certified that error appears in the above-identified patent and that said Letters Patent is hereby corrected as shown below:

On Title Page:
Item 75, Inventors: Please correct "Paula D. Ladd, Seattle, WA (US)"
to read -- Paula D. Ladd, San Diego, CA (US) --

In the Specification:
Column 31, Lines 56-57:
Please correct "5'-CTCATTTGGAATMGCCGATT-3' (SEQ ID NO:66)"
to read -- 5'-CTCATTTGGAATTTTGCCGATT-3' (SEQ ID NO:66) --

Column 43, Table 2, Lines 44-45:
Please correct "+15Forward    5'-CGACTGGAGCACGAGGACACTGAgctc'    27
                              agctccgtttcggtttcacttccggt-3"
to read -- +15Forward    5'-CGACTGGAGCACGAGGACACTGAgctc    27
                         agctccgtttcggtttcacttccggt-3' --

Column 44, Table 2, Line 30:
Please correct "Strand Specific RT-PCR Primers"
to read -- RACE Primers --

Column 44, Table 2, Line 59:
Please correct "-1185R    5'-catgacctagtctggggtg gag-3'    52"
to read -- -1185R    5'-catgacctagtctggggtggag-3'    52 --

Column 44, Table 2, Line 64:
Please correct "-1058R    5'-cg actgccagcattgaacttag-3'    55"
to read -- -1058R    5'-cgactgccagcattgaacttag-3'    55 --

Column 45, Table 2, Line 3:
Please correct "Strand Specific RT-PCR Primers"

Signed and Sealed this
Sixteenth Day of September, 2014

Michelle K. Lee
*Deputy Director of the United States Patent and Trademark Office*

CERTIFICATE OF CORRECTION (continued)
U.S. Pat. No. 8,597,880 B2 to read -- RACE Primers --

Column 46, Table 2, Line 3:
Please correct "Strand Specific RT-PCR Primers"
        to read -- RACE Primers --

SEQUENCE LISTING

<160> NUMBER OF SEQ ID NOS: 67

<210> SEQ ID NO 1
<211> LENGTH: 3026
<212> TYPE: DNA
<213> ORGANISM: Homo sapiens

<400> SEQUENCE: 1

```
cagtcattcc attagtttaa tactgagttg ttcagaaact tctcagtcag taacatgaag      60
atccattcct gaaaagcact caaactggac ttgaattttt aaaaaatgaa gaatagaatt     120
agcataaaat attaagaac ctcatcatta aaattatata acgagacact tacttgtttt      180
caaatgcaac tgttattgaa tcttcatgaa catcctttac aaatgccttg tagaaagcgc     240
cattggagcc ccgcacttcc accaccagct cctccatctt ctcttcagcc ctgctagcgc     300
cgggagcccg ccccgagag gtgggctgcg ggcgctcgag gccagccgc cgccgccgcc       360
gccgccgccg ccgcctccgc cgccgccgcc gccgccgccg ccgccgcgct gccgcacgcc     420
ccctggcagc ggcgcctccg tcaccgccgc cgcccgcgct cgccgtcggc ccgccgcccg     480
ctcagaggcg gccctccacc ggaagtgaaa ccgaaacgga gctgagcgcc tgactgaggc     540
cgaaccccccg gccgctgcg ggtgtaaaca ctgaaaccac gtcacgtgat caacgctgtt     600
ccctccccccc gcgggctcag cccctcggcc ccgccctctc tcttcaagtg gcctgggagc    660
gcgcgcatgc gcgctgctgg gaaccggccg gggtgccggg tcgaaagaca gacgcgcggg    720
ccgggcgtgc gcgggcttgg tggagggcgg gaaggctgaa gggcggtgac aggtcgcact     780
gcctcgcgag ggccagaacg cccatttctg cagaggtgca ctcagtggcg tgggaaatca     840
aatgcatccg gttatcccag ttcggcctct ctgggattcc gcgggagggg gtgtctggtc     900
tggtttggtt tggtttggtt tggtttggtt tggtccggtt caaagtagcg cagtctgact     960
gagcgggagg tggagtggaa ggcgagaata ggggtgaagg attagacaga agaagacttt    1020
gaactaggaa cagtggcaac cagggtgacc caggcttttg tgacccgtag aggcagaagg    1080
tgaggcgtct acgccctctc tcaccagatt ttgggcggcc ctgtggagac accctgtgcc    1140
ctttaaggga catggattga gtcggatctc aaaatgtga gcctttcctc agacccagct    1200
ttgacccacg tactcgcctt tcctcaactc attttcatac tttcacttga ctatatattt    1260
tttaaaaatt gtgttaagca cttgaggttc atttctgccc ctactgtatg tgcaccctgt    1320
gccagagggt ggggtgaaca cgtgtgtagc agtcatgcgt cctgtccaca ggggccgatg    1380
cacctccttg caacccttta cattccactg tgaaacaaac ctcaacttttt tcttattcct  1440
gttttttacac cgtgcttata gctgccttaa tccatgttcc cttcgggatg ctggtatcca   1500
actgagaagt tgacggagca tctatcgtgt gccagacact gtgctaagtg ctaacgagaa    1560
atcggtgagc aaaacagaaa agaaaaaaaa agaagaaacg actgccagca ttgaacttag   1620
tacctagcaa agtaggtgga cataaatcaa attgtcagac aagtaaatga gtagttgcag    1680
ctgtgataag gggtatgaag aataggcgct tccatgatgg cggaacatga cctagtctgg    1740
```

```
ggtggagaag gggagatgat tccagctgga atatggcagg tgagagttaa ctaatagcac    1800
tgagttggca gaggcaggat gacctgcccc aggcaggtgc cccagaatga gaggatgttg    1860
ctgctggtgg aactccagct ttaaagcggt ggatctaggg ccacattcct caaggccata    1920
gcaaacagga aagaccttttt ggactagggt cttttggagta gtcacatgag gccaagaacc    1980
caatagggct gaaagagaat ctcatcatag gctgaatggg agcagagcat tagctgcaac    2040
tccaatgtat tatagtaaaa ggggacacat tgattagaat gattataccc ctccaagtgt    2100
aagctgttgt tcaatttacc cagggcttaa aaatatgtca actcttcaca accatttttta    2160 ctacaagcca cactcaacct gtgttgttcc ctgaacctgt gatgcacttt catccgttca    2220
tgtctctaca catccttcct gggcccata gaggccctgc accttaaggt tttcagctgg    2280
attcctatta gctagttatt ttatctcagg tacagagagt taactttgct cctcaatttt    2340
cagcacattg tcatatcagt ccctacaggg tccttgttta cattattttta tagtgtttat    2400 attatttttt cctcatcttt ctcgatcccc actctcattc ttctagacac aagctgcaat    2460
atgttcgata gagatccttg ataatttaac acagataatg ttttgtttat gcctcttgca    2520
tttacagaga tggtattgga ctgtaaatct ctatttccca ctgttttact caacagtctg    2580 ttttttgagct atacccacat tgctgtgtgt cacctagtt tgctaccgag tatgccagaa    2640
attttattca tacatatccc tactgatcgg gcatctaggt tactgccaac tccctgaagt    2700
catactgtgg tgaaaaccct tgtgaatgtc tttacaaacc tttgccagaa cttattttgt    2760
gctcttgtag aactttgtgc ataccctctg cttcctcatt acactgcttg gcatatagca    2820
gagactcaac aaatgttgaa tacctctact atgatggtta gtgtactaga ataatttatt    2880
tatatttctg ttttccttat tggattatta gtaccttcca gacagggcaa atgtcttttc    2940
tatctttgtg tccctggcac attaaaagtg gttgatttca aggtatgttc aatgaatgaa    3000
taaatactta tcttcactgc cagtac                                        3026

<210> SEQ ID NO 2
<211> LENGTH: 2644
<212> TYPE: DNA
<213> ORGANISM: Homo sapiens

<400> SEQUENCE: 2
cagtcattcc attagtttaa tactgagttg ttcagaaact tctcagtcag taacatgaag     60
atccattcct gaaaagcact caaactggac ttgaattttt aaaaaatgaa gaatagaatt    120
agcataaaat attaaagaac ctcatcatta aaattatata acgagacact tacttgtttt    180
caaatgcaac tgttattgaa tcttcatgaa catcctttac aaatgccttg tagaaagcgc    240
cattggagcc ccgcacttcc accaccagct cctccatctt ctcttcagcc ctgctagcgc    300
cgggagcccg cccccgagag gtgggctgcg ggcgctcgag gccagccgc cgccgccgcc    360 gccgccgccg ccgcctccgc cgccgccgcc gccgccgccg ccgccgcgct gccgcacgcc    420
ccctggcagc ggcgcctccg tcaccgccgc cgcccgcgct cgccgtcggc ccgccgcccg    480
ctcagaggcg gccctccacc ggaagtgaaa ccgaaacgga gctgagcgcc tgactgaggc    540
cgaacccccg gcccgctgcg ggtgtaaaca ctgaaaccac gtcacgtgat caacgctgtt    600 ccctccccc gcgggctcag ccctcggcc ccgccctctc tcttcaagtg gcctgggagc    660
gcgcgcatgc gcgctgctgg gaaccggccg gggtgccggg tcgaaagaca gacgcgcggg    720
ccgggcgtgc gcgggcttgg tggagggcgg gaaggctgaa gggcggtgac aggtcgcact    780
gcctcgcgag ggccagaacg cccatttctg cagaggtgca ctcagtggcg tgggaaatca    840
```

```
aatgcatccg gttatcccag ttcggcctct ctgggattcc gcgggagggg gtgtctggtc    900
tggtttggtt tggtttggtt tggtttggtt tggtccggtt caaagtagcg cagtctgact    960
gagcgggagg tggagtggaa ggcgagaata ggggtgaagg attagacaga agaagacttt   1020
gaactaggaa cagtggcaac cagggtgacc caggcttttg tgacccgtag aggcagaagc   1080
tgccttaatc catgttccct tcgggatgct ggtatccaac tgagaagttg acggagcatc   1140
tatcgtgtgc cagacactgt gctaagtgct aacgagaaat cggtgagcaa aacagaaaag   1200
aaaaaaaaag aagaaacgac tgccagcatt gaacttagta cctagcaaag taggtggaca   1260
taaatcaaat tgtcagacaa gtaaatgagt agttgcagct gtgataaggg gtatgaagaa   1320
taggcgcttc catgatggcg aacatgacc tagtctgggg tggagaaggg gagatgattc    1380
cagctggaat atggcaggtg agagttaact aatagcactg agttggcaga ggcaggatga   1440
cctgccccag gcaggtgccc cagaatgaga ggatgttgct gctggtggaa ctccagcttt   1500
aaagcggtgg atctagggcc acattcctca aggccatagc aaacaggaaa gaccttttgg   1560
actagggtct ttggagtagt cacatgaggc caagaaccca atagggctga agagaatct    1620 catcataggc tgaatgggag cagagcatta gctgcaactc caatgtatta tagtaaaagg   1680
ggacacattg attagaatga ttatacccct ccaagtgtaa gctgttgttc aatttaccca   1740
gggcttaaaa atatgtcaac tcttcacaac cattttact acaagccaca ctcaacctgt    1800
gttgttccct gaacctgtga tgcactttca tccgttcatg tctctacaca tccttcctgg   1860
gccccataga ggccctgcac cttaaggttt tcagctggat tcctattagc tagttatttt   1920
atctcaggta cagagagtta actttgctcc tcaattttca gcacattgtc atatcagtcc   1980
ctacagggtc cttgtttaca ttattttata gtgtttatat tattttttcc tcatcttcct   2040
cgatccccac tctcattctt ctagacacaa gctgcaatat gttcgataga gatccttgat   2100
aatttaacac agataatgtt ttgtttatgc ctcttgcatt tacagagatg gtattggact   2160
gtaaatctct atttcccact gttttactca acagtctgtt tttgagctat acccacattg   2220
ctgtgtgtac acctagtttg ctaccgagta tgccagaaat tttattcata catatcccta   2280
ctgatcgggc atctaggtta ctgccaactc cctgaagtca tactgtggtg aaaacccttg   2340
tgaatgtctt tacaaacctt tgccagaact tattttgtgc tcttgtagaa ctttgtgcat   2400
accctctgct tcctcattac actgcttggc atatagcaga gactcaacaa atgttgaata   2460
cctctactat gatggttagt gtactagaat aatttattta tatttctgtt ttccttattg   2520
gattattagt accttccaga cagggcaaat gtcttttcta tctttgtgtc cctggcacat   2580
taaaagtggt tgatttcaag gtatgttcaa tgaatgaata aatacttatc ttcactgcca   2640
gtac                                                               2644
```

<210> SEQ ID NO 3
<211> LENGTH: 2484
<212> TYPE: DNA
<213> ORGANISM: Homo sapiens

<400> SEQUENCE: 3

```
cagtcattcc attagtttaa tactgagttg ttcagaaact tctcagtcag taacatgaag     60
atccattcct gaaaagcact caaactggac ttgaattttt aaaaaatgaa gaatagaatt    120
agcataaaat attaaagaac ctcatcatta aaattatata acgagacact tacttgtttt    180
caaatgcaac tgttattgaa tcttcatgaa catcctttac aaatgccttg tagaaagcgc    240
cattggagcc ccgcacttcc accaccagct cctccatctt ctcttcagcc ctgctagcgc    300
```

```
cgggagcccg ccccccgagag gtgggctgcg ggcgctcgag gcccagccgc cgccgccgcc    360
gccgccgccg ccgcctccgc cgccgccgcc gccgccgccg ccgccgcgct gccgcacgcc    420
ccctggcagc ggcgcctccg tcaccgccgc cgcccgcgct cgccgtcggc ccgccgcccg    480
ctcagaggcg gccctccacc ggaagtgaaa ccgaaacgga gctgagcgcc tgactgaggc    540
cgaacccccg gcccgctgcg ggtgtaaaca ctgaaaccac gtcacgtgat caacgctgtt    600
ccctccccccc gcgggctcag cccctcggcc ccgccctctc tcttcaagtg gcctgggagc    660
gcgcgcatgc gcgctgctgg gaaccggccg gggtgccggg tcgaaagaca gacgcgcggg    720
ccgggcgtgc gcgggcttgg tggagggcgg gaaggctgaa gggcggtgac aggtcgcact    780
gcctcgcgag ggccagaacg cccatttctg cagaggcaga aggtgaggcg tctacgccct    840
ctctcaccag attttgggcg gccctgtgga gacaccctgt gcccttaaag ggacatggat    900
tgagtcggga tctcaaaatc tgccttaatc catgttccct tcgggatgct ggtatccaac    960
tgagaagttg acgagcatc tatcgtgtgc cagacactgt gctaagtgct aacgagaaat    1020
cggtgagcaa acagaaaag aaaaaaaaag aagaacgac tgccagcatt gaacttagta    1080
cctagcaaag taggtggaca taatcaaat tgtcagacaa gtaaatgagt agttgcagct    1140
gtgataaggg gtatgaagaa taggcgcttc catgatggcg aacatgacc tagtctgggg    1200
tggagaaggg gagatgattc cagctggaat atggcaggtg agagttaact aatagcactg    1260
agttggcaga ggcaggatga cctgccccag gcaggtgccc cagaatgaga ggatgttgct    1320
gctggtggaa ctccagcttt aaagcggtgg atctagggcc acattcctca aggccatagc    1380
aaacaggaaa gacctttgg actagggtct ttggagtagt cacatgaggc caagaaccca    1440
atagggctga aagagaatct catcataggc tgaatgggag cagagcatta gctgcaactc    1500
caatgtatta tagtaaaagg ggacacattg attagaatga ttatacccct ccaagtgtaa    1560
gctgttgttc aatttaccca gggcttaaaa atatgtcaac tcttcacaac cattttact    1620
acaagccaca ctcaacctgt gttgttccct gaacctgtga tgcactttca tccgttcatg    1680
tctctacaca tccttcctgg gccccataga ggccctgcac cttaaggttt tcagctggat    1740
tcctattagc tagttatttt atctcaggta cagagagtta actttgctcc tcaattttca    1800
gcacattgtc atatcagtcc ctacagggtc cttgtttaca ttattttata gtgtttatat    1860
tattttttcc tcatctttct cgatccccac tctcattctt ctagacacaa gctgcaatat    1920
gttcgataga gatccttgat aatttaacac agataatgtt ttgtttatgc ctcttgcatt    1980
tacagagatg gtattggact gtaaatctct atttcccact gttttactca acagtctgtt    2040
tttgagctat acccacattg ctgtgtgtac acctagtttg ctaccgagta tgccagaaat    2100
tttattcata catatcccta ctgatcgggc atctaggtta ctgccaactc cctgaagtca    2160
tactgtggtg aaaaccctg tgaatgtctt tacaaacctt tgccagaact tattttgtgc    2220
tcttgtagaa ctttgtgcat accctctgct tcctcattac actgcttggc atatagcaga    2280
gactcaacaa atgttgaata cctctactat gatggttagt gtactagaat aatttatta    2340
tatttctgtt ttccttattg gattattagt accttccaga cagggcaaat gtcttttcta    2400
tctttgtgtc cctggcacat taaaagtggt tgatttcaag gtatgttcaa tgaatgaata    2460
aatacttatc ttcactgcca gtac                                          2484
```

<210> SEQ ID NO 4
<211> LENGTH: 2380
<212> TYPE: DNA
<213> ORGANISM: Homo sapiens

```
<400> SEQUENCE: 4
cagtcattcc attagtttaa tactgagttg ttcagaaact tctcagtcag taacatgaag      60
atccattcct gaaaagcact caaactggac ttgaattttt aaaaaatgaa gaatagaatt     120
agcataaaat attaaagaac ctcatcatta aaattatata acgagacact tacttgtttt     180
caaatgcaac tgttattgaa tcttcatgaa catcctttac aaatgccttg tagaaagcgc     240
cattggagcc ccgcacttcc accaccagct cctccatctt ctcttcagcc ctgctagcgc     300
cgggagcccg cccccgagag gtgggctgcg ggcgctcgag gcccagccgc cgccgccgcc     360
gccgccgccg ccgcctccgc cgccgccgcc gccgccgccg ccgccgcgct gccgcacgcc     420
ccctggcagc ggcgcctccg tcaccgccgc cgcccgcgct cgccgtcggc ccgccgcccg     480
ctcagaggcg gccctccacc ggaagtgaaa ccgaaacgga gctgagcgcc tgactgaggc     540 cgaaccccg gcccgctgcg ggtgtaaaca ctgaaaccac gtcacgtgat caacgctgtt     600
ccctcccccc gcgggctcag cccctcggcc ccgcccctct tcttcaagtg gcctgggagc     660
gcgcgcatgc gcgctgctgg gaaccggccg gggtgccggg tcgaaagaca gacgcgcggg     720
ccgggcgtgc gcgggcttgg tggagggcgg gaaggctgaa gggcggtgac aggtcgcact     780
gcctcgcgag ggccagaacg cccatttctg cagagctgcc ttaatccatg ttcccttcgg     840
gatgctggta tccaactgag aagttgacgg agcatctatc gtgtgccaga cactgtgcta     900
agtgctaacg agaaatcggt gagcaaaaca gaaagaaaa aaaagaaga aacgactgcc      960 agcattgaac ttagtaccta gcaaagtagg tggacataaa tcaaattgtc agacaagtaa    1020
atgagtagtt gcagctgtga taaggggtat gaagaatagg cgcttccatg atggcggaac    1080
atgacctagt ctggggtgga gaaggggaga tgattccagc tggaatatgg caggtgagag    1140
ttaactaata gcactgagtt ggcagaggca ggatgacctg ccccaggcag gtgccccaga    1200
atgagaggat gttgctgctg gtggaactcc agctttaaag cggtggatct agggccacat    1260
tcctcaaggc catagcaaac aggaaagacc ttttggacta gggtctttgg agtagtcaca    1320
tgaggccaag aacccaatag ggctgaaaga gaatctcatc ataggctgaa tgggagcaga    1380
gcattagctg caactccaat gtattatagt aaaaggggac acattgatta gaatgattat    1440 accctccaa gtgtaagctg ttgttcaatt tacccagggc ttaaaaatat gtcaactctt    1500
cacaaccatt tttactacaa gccacactca acctgtgttg ttccctgaac ctgtgatgca    1560
ctttcatccg ttcatgtctc tacacatcct tcctgggccc catagaggcc ctgcaccttta   1620 aggttttcag ctggattcct attagctagt tattttatct caggtacaga gagttaactt    1680
tgctcctcaa ttttcagcac attgtcatat cagtccctac agggtccttg tttacattat    1740
tttatagtgt ttatattatt ttttcctcat ctttctcgat ccccactctc attcttctag    1800
acacaagctg caatatgttc gatagagatc cttgataatt taacacagat aatgttttgt    1860
ttatgcctct tgcatttaca gagatggtat tggactgtaa atctctattt cccactgttt    1920
tactcaacag tctgttttg agctataccc acattgctgt gtgtacacct agtttgctac     1980
cgagtatgcc agaaatttta ttcatacata tccctactga tcgggcatct aggttactgc    2040
caactccctg aagtcatact gtggtgaaaa cccttgtgaa tgtctttaca aacctttgcc    2100
agaacttatt ttgtgctctt gtagaacttt gtgcatacccc tctgcttcct cattacactg   2160
cttggcatat agcagagact caacaaatgt tgaatacctc tactatgatg gttagtgtac    2220
tagaataatt tatttatatt tctgtttttcc ttattggatt attagtacct tccagacagg    2280
gcaaatgtct tttctatctt tgtgtccctg gcacattaaa agtggttgat ttcaaggtat    2340
```

```
gttcaatgaa tgaataaata cttatcttca ctgccagtac                            2380

<210> SEQ ID NO 5
<211> LENGTH: 2942
<212> TYPE: DNA
<213> ORGANISM: Homo sapiens

<400> SEQUENCE: 5
cagtcattcc attagtttaa tactgagttg ttcagaaact tctcagtcag taacatgaag      60
atccattcct gaaaagcact caaactggat tgttttcaaa tgcaactgtt attgaatctt     120
catgaacatc ctttacaaat gccttgtaga aagcgccatt ggagcccgc acttccacca     180 ccagctcctc catcttctct tcagccctgc tagcgccggg agcccgcccc cgagaggtgg    240
gctgcgggcg ctcgaggccc agccgccgcc gccgccgccg ccgccgccgc ctccgccgcc    300
gccgccgccg ccgccgccgc cgcgctgccg cacgccccct ggcagcggcg cctccgtcac    360
cgccgccgcc cgcgctcgcc gtcggcccgc cgcccgctca gaggcggccc tccaccggaa    420
gtgaaaccga acggagctg agcgcctgac tgaggccgaa ccccggccc gctgcgggtg     480 taaacactga accacgtca cgtgatcaac gctgttccct ccccccgcgg gctcagcccc     540
tcggccccgc cctctctctt caagtggcct gggagcgcgc gcatgcgcgc tgctgggaac    600
cggccggggt gccgggtcga agacagacg cgcgggccgg gcgtgcgcgg gcttggtgga    660
gggcgggaag gctgaagggc ggtgacaggt cgcactgcct cgcgagggcc agaacgccca    720
tttctgcaga ggtgcactca gtggcgtggg aaatcaaatg catccggtta tcccagttcg    780
gcctctctgg gattccgcgg gaggggtgt ctggtctggt ttggtttggt ttggtttggt     840
ttggtttggt ccggttcaaa gtagcgcagt ctgactgagc gggaggtgga gtggaaggcg    900
agaatagggg tgaaggatta gacagaagaa gactttgaac taggaacagt ggcaaccagg    960
gtgacccagg cttttgtgac ccgtagaggc agaaggtgag gcgtctacgc cctctctcac   1020
cagattttgg gcggccctgt ggagacaccc tgtgcccttt aagggacatg gattgagtcg   1080
ggatctcaaa atgtgagcct ttcctcagac ccagctttga cccacgtact cgcctttcct   1140
caactcattt tcatactttc acttgactat atattttta aaaattgtgt taagcacttg    1200
aggttcattt ctgcccctac tgtatgtgca ccctgtgcca gagggtgggg tgaacacgtg   1260
tgtagcagtc atgcgtcctg tccacagggg ccgatgcacc tccttgcaac cctttacatt   1320
ccactgtgaa acaaacctca acttttttctt attcctgttt ttacaccgtg cttatagctg   1380
ccttaatcca tgttcccttc gggatgctgg tatccaactg agaagttgac ggagcatcta   1440
tcgtgtgcca gacactgtgc taagtgctaa cgagaaatcg gtgagcaaaa cagaaaagaa   1500 aaaaaagaa gaaacgactg ccagcattga acttagtacc tagcaaagta ggtggacata   1560
aatcaaattg tcagacaagt aaatgagtag ttgcagctgt gataagggg atgaagaata    1620 ggcgcttcca tgatggcgga acatgaccta gtctggggtg gagaaggggga gatgattcca  1680 gctggaatat ggcaggtgag agttaactaa tagcactgag ttggcagagg caggatgacc   1740
tgccccaggc aggtgcccca gaatgagagg atgttgctgc tggtggaact ccagctttaa   1800
agcggtggat ctagggccac attcctcaag gccatagcaa acaggaaaga ccttttggac   1860
tagggtcttt ggagtagtca catgaggcca agaacccaat agggctgaaa agaatctca   1920 tcataggctg aatgggagca gagcattagc tgcaactcca atgtattata gtaaaagggg   1980
acacattgat tagaatgatt ataccctccc aagtgtaagc tgttgttcaa tttacccagg   2040
gcttaaaaat atgtcaactc ttcacaacca tttttactac aagccacact caacctgtgt   2100
```

```
tgttccctga acctgtgatg cactttcatc cgttcatgtc tctacacatc cttcctgggc    2160
cccatagagg ccctgcacct taaggttttc agctggattc ctattagcta gttattttat    2220
ctcaggtaca gagagttaac tttgctcctc aattttcagc acattgtcat atcagtccct    2280
acagggtcct tgtttacatt attttatagt gtttatatta ttttttcctc atctttctcg    2340
atccccactc tcattcttct agacacaagc tgcaatatgt tcgatagaga tccttgataa    2400
tttaacacag ataatgtttt gtttatgcct cttgcattta cagagatggt attggactgt    2460
aaatctctat ttcccactgt tttactcaac agtctgtttt tgagctatac ccacattgct    2520
gtgtgtacac ctagtttgct accgagtatg ccagaaattt tattcataca tatccctact    2580
gatcgggcat ctaggttact gccaactccc tgaagtcata ctgtggtgaa aacccttgtg    2640
aatgtcttta caaacctttg ccagaactta ttttgtgctc ttgtagaact ttgtgcatac    2700
cctctgcttc ctcattacac tgcttggcat atagcagaga ctcaacaaat gttgaatacc    2760
tctactatga tggttagtgt actagaataa tttatttata tttctgtttt ccttattgga    2820
ttattagtac cttccagaca gggcaaatgt cttttctatc tttgtgtccc tggcacatta    2880
aaagtggttg atttcaaggt atgttcaatg aatgaataaa tacttatctt cactgccagt    2940
ac                                                                   2942
```

<210> SEQ ID NO 6
<211> LENGTH: 100
<212> TYPE: PRT
<213> ORGANISM: Homo sapiens

<400> SEQUENCE: 6

```
Met Asn Ile Leu Tyr Lys Cys Leu Val Glu Ser Ala Ile Gly Ala Pro
1               5                   10                  15

His Phe His His Gln Leu Leu His Leu Leu Phe Ser Pro Ala Ser Ala
            20                  25                  30

Gly Ser Pro Pro Pro Arg Gly Gly Leu Arg Ala Leu Glu Ala Gln Pro
        35                  40                  45

Pro Pro Pro Pro Pro Pro Pro Pro Pro Pro Pro Pro Pro Pro Pro Pro
    50                  55                  60

Pro Pro Pro Arg Cys Arg Thr Pro Pro Gly Ser Gly Ala Ser Val Thr
65                  70                  75                  80

Ala Ala Ala Arg Ala Arg Arg Arg Pro Ala Arg Ser Glu Ala Ala
                85                  90                  95

Leu His Arg Lys
            100
```

<210> SEQ ID NO 7
<211> LENGTH: 274
<212> TYPE: DNA
<213> ORGANISM: Homo sapiens

<400> SEQUENCE: 7

```
gcctgactga ggccgaaccc ccggcccgct gcgggtgtaa acactgaaac cacgtcacgt     60
gatcaacgct gttccctccc cccgcgggct cagcccctcg gccccgccct ctctcttcaa    120
gtggcctggg agcgcgcgca tgcgcgctgc tgggaaccgg ccggggtgcc gggtcgaaag    180
acagacgcgc gggccgggcg tgcgcgggct tggtggaggg cgggaaggct gaagggcggt    240
gacaggtcgc actgcctcgc gagggccaga acgc                                274
```

<210> SEQ ID NO 8

```
<211> LENGTH: 86
<212> TYPE: DNA
<213> ORGANISM: Homo sapiens

<400> SEQUENCE: 8
aggatcaata ccatacaata agggacctcc aggacattag cagaaacagt cattccatta     60
gtttaatact gagttgttca gaaact                                          86

<210> SEQ ID NO 9
<211> LENGTH: 810
<212> TYPE: RNA
<213> ORGANISM: Homo sapiens

<400> SEQUENCE: 9
agucauucca uuaguuuaau acugaguugu cagaaacuu cucagucagu aacaugaaga      60
uccauuccug aaaagcacuc aaacuggacu ugaauuuuua aaaaaugaag aauagaauua    120
gcauaaaaua uuaagaaacc ucaucauuaa aauuauauaa cgagacacuu acuuguuuuc    180
aaaugcaacu guuauugaau cuucaugaac auccuuuaca aaugccuugu agaaagcgcc    240
auuggagccc cgcacuucca ccaccagcuc uccaucuuuc ucuucagccc ugcuagcgcc    300
gggagcccgc ccccgagagg ugggcugcgg gcgcucgagg cccagccgcc gccgccgccg    360
ccgccgccgc cgccuccgcc gccgccgccg ccgccgccgc cgccgcgcug ccgcacgccc    420
ccuggcagcg gcgccuccgu caccgccgcc gcccgcgcuc gccgucggcc cgccgcccgc    480
ucagaggcgg cccuccaccg gaagugaaac cgagacggag cugagcgccu gacugaggcc    540
gaaccccggg cccgcugcgg guguaaacac ugaaccacg ucacgugauc aacgcuguuc     600 ccucccccg cgggcucagc ccucggccc cgcccucucu cuucaagugg ccugggagcg      660
cgcgcaugcg cgcugcuggg aaccggccgg ggugccgggu cgaaagacag acgcgcgggc    720
cgggcgugcg cgggcuuggu ggagggcggg aaggcugaag ggcggugaca ggucgcacug    780
ccucgcgagg gccagaacgc ccauuucugc                                     810

<210> SEQ ID NO 10
<211> LENGTH: 15
<212> TYPE: DNA
<213> ORGANISM: Homo sapiens

<400> SEQUENCE: 10
aaactggact tgaat                                                     15

<210> SEQ ID NO 11
<211> LENGTH: 15
<212> TYPE: DNA
<213> ORGANISM: Homo sapiens

<400> SEQUENCE: 11
cacttacttg ttttc                                                     15

<210> SEQ ID NO 12
<211> LENGTH: 15
<212> TYPE: DNA
<213> ORGANISM: Homo sapiens

<400> SEQUENCE: 12
acaaatgcct gtgta                                                     15

<210> SEQ ID NO 13
<211> LENGTH: 15
<212> TYPE: DNA
```

```
<213> ORGANISM: Homo sapiens

<400> SEQUENCE: 13
caagtacctt gtaga                                                          15

<210> SEQ ID NO 14
<211> LENGTH: 15
<212> TYPE: DNA
<213> ORGANISM: Homo sapiens

<400> SEQUENCE: 14
ctgcagaggt gcact                                                          15

<210> SEQ ID NO 15
<211> LENGTH: 15
<212> TYPE: DNA
<213> ORGANISM: Homo sapiens

<400> SEQUENCE: 15
ttaatagctg cctta                                                          15

<210> SEQ ID NO 16
<211> LENGTH: 15
<212> TYPE: DNA
<213> ORGANISM: Homo sapiens

<400> SEQUENCE: 16
ggcagaaggt gaggc                                                          15

<210> SEQ ID NO 17
<211> LENGTH: 15
<212> TYPE: DNA
<213> ORGANISM: Homo sapiens

<400> SEQUENCE: 17
ctgcagaggt gcact                                                          15

<210> SEQ ID NO 18
<211> LENGTH: 15
<212> TYPE: DNA
<213> ORGANISM: Homo sapiens

<400> SEQUENCE: 18
cccgtagagg cagaa                                                          15

<210> SEQ ID NO 19
<211> LENGTH: 15
<212> TYPE: DNA
<213> ORGANISM: Homo sapiens

<400> SEQUENCE: 19
ctcaaaatgt gagcc                                                          15

<210> SEQ ID NO 20
<211> LENGTH: 43
<212> TYPE: DNA
<213> ORGANISM: Homo sapiens

<400> SEQUENCE: 20
tatgttcaat gaatgaataa atacttatct tcactgccag tac                           43

<210> SEQ ID NO 21
<211> LENGTH: 91
<212> TYPE: PRT
```

-continued

<213> ORGANISM: Mus musculus

<400> SEQUENCE: 21

Met Asp Ile Phe Tyr Lys Cys Leu Val Glu Ser Ala Ile Gly Ala Pro
1               5                   10                  15

His Phe His His Gln Leu Leu His Leu Leu Val Arg Pro Arg Ala Gly
            20                  25                  30

Ser Pro Pro Gly Gly Gly Leu Gln Ala Leu Glu Ala Gln Pro Pro
        35                  40                  45

Ser Pro Pro Pro Pro Pro Arg Tyr Arg Thr Pro Pro Gly Ser Gly
    50                  55                  60

Ala Ala Val Thr Ala Thr Ala Arg Ala Arg Arg Pro Phe Ala Ser Leu
65                  70                  75                  80

Pro Ser Leu Ser Gly Ala Ala Pro His Arg Lys
                85                  90

<210> SEQ ID NO 22
<211> LENGTH: 23
<212> TYPE: DNA
<213> ORGANISM: Artificial
<220> FEATURE:
<223> OTHER INFORMATION: RT-PCR primer

<400> SEQUENCE: 22
cgactggagc acgaggacac tga                                    23

<210> SEQ ID NO 23
<211> LENGTH: 43
<212> TYPE: DNA
<213> ORGANISM: Artificial
<220> FEATURE:
<223> OTHER INFORMATION: RT-PCR primer

<400> SEQUENCE: 23
cgactggagc acgaggacac tgagtactgg cagtgaagat aag              43

<210> SEQ ID NO 24
<211> LENGTH: 49
<212> TYPE: DNA
<213> ORGANISM: Artificial
<220> FEATURE:
<223> OTHER INFORMATION: RT-PCR primer

<400> SEQUENCE: 24
cgactggagc acgaggacac tgacagtgtc tggcacacga tagatgctc        49

<210> SEQ ID NO 25
<211> LENGTH: 25
<212> TYPE: DNA
<213> ORGANISM: Artificial
<220> FEATURE:
<223> OTHER INFORMATION: RT-PCR primer

<400> SEQUENCE: 25
ggtgcactca gtggcgtggg aaatc                                  25

<210> SEQ ID NO 26
<211> LENGTH: 25
<212> TYPE: DNA
<213> ORGANISM: Artificial
<220> FEATURE:
<223> OTHER INFORMATION: RT-PCR primer

<400> SEQUENCE: 26
ggtggagggc gggaaggctg aaggg                                        25

<210> SEQ ID NO 27
<211> LENGTH: 53
<212> TYPE: DNA
<213> ORGANISM: Artificial
<220> FEATURE:
<223> OTHER INFORMATION: RT-PCR primer

<400> SEQUENCE: 27
cgactggagc acgaggacac tgagctcagc tccgtttcgg tttcacttcc ggt         53

<210> SEQ ID NO 28
<211> LENGTH: 25
<212> TYPE: DNA
<213> ORGANISM: Artificial
<220> FEATURE:
<223> OTHER INFORMATION: RT-PCR primer

<400> SEQUENCE: 28
cagaggcggc cctccaccgg aagtg                                        25

<210> SEQ ID NO 29
<211> LENGTH: 47
<212> TYPE: DNA
<213> ORGANISM: Artificial
<220> FEATURE:
<223> OTHER INFORMATION: RT-PCR primer

<400> SEQUENCE: 29
cgactggagc acgaggacac tgacccgcag cccacctctc ggggcg                 47

<210> SEQ ID NO 30
<211> LENGTH: 30
<212> TYPE: DNA
<213> ORGANISM: Artificial
<220> FEATURE:
<223> OTHER INFORMATION: RT-PCR primer

<400> SEQUENCE: 30
agccccgcac ttccaccacc agctcctcca                                   30

<210> SEQ ID NO 31
<211> LENGTH: 48
<212> TYPE: DNA
<213> ORGANISM: Artificial
<220> FEATURE:
<223> OTHER INFORMATION: RT-PCR primer

<400> SEQUENCE: 31
cgactggagc acgaggacac tgaaggatgt tcatgaagat tcaataag               48

<210> SEQ ID NO 32
<211> LENGTH: 23
<212> TYPE: DNA
<213> ORGANISM: Artificial
<220> FEATURE:
<223> OTHER INFORMATION: RT-PCR primer

<400> SEQUENCE: 32
agcagaaaca gtcattccat tag                                          23

<210> SEQ ID NO 33
<211> LENGTH: 28
<212> TYPE: DNA
<213> ORGANISM: Artificial
<220> FEATURE:

```
<223> OTHER INFORMATION: RACE primer

<400> SEQUENCE: 33
catgtgacta ctccaaagac cctagtcc                                    28

<210> SEQ ID NO 34
<211> LENGTH: 23
<212> TYPE: DNA
<213> ORGANISM: Artificial
<220> FEATURE:
<223> OTHER INFORMATION: RACE primer

<400> SEQUENCE: 34
ttgctatggc cttgaggaat gtg                                         23

<210> SEQ ID NO 35
<211> LENGTH: 29
<212> TYPE: DNA
<213> ORGANISM: Artificial
<220> FEATURE:
<223> OTHER INFORMATION: RACE primer

<400> SEQUENCE: 35
ctctcacctg ccatattcca gctggaatc                                   29

<210> SEQ ID NO 36
<211> LENGTH: 21
<212> TYPE: DNA
<213> ORGANISM: Artificial
<220> FEATURE:
<223> OTHER INFORMATION: RACE primer

<400> SEQUENCE: 36
ggaagcgcct attcttcata c                                           21

<210> SEQ ID NO 37
<211> LENGTH: 26
<212> TYPE: DNA
<213> ORGANISM: Artificial
<220> FEATURE:
<223> OTHER INFORMATION: RACE primer

<400> SEQUENCE: 37
cagtgtctgg cacacgatag atgctc                                      26

<210> SEQ ID NO 38
<211> LENGTH: 22
<212> TYPE: DNA
<213> ORGANISM: Artificial
<220> FEATURE:
<223> OTHER INFORMATION: RACE primer

<400> SEQUENCE: 38
cgtcaacttc tcagttggat ac                                          22

<210> SEQ ID NO 39
<211> LENGTH: 27
<212> TYPE: DNA
<213> ORGANISM: Artificial
<220> FEATURE:
<223> OTHER INFORMATION: RACE primer

<400> SEQUENCE: 39
tctggtgaga gagggcgtag acgcctc                                     27

<210> SEQ ID NO 40
```

```
<211> LENGTH: 24
<212> TYPE: DNA
<213> ORGANISM: Artificial
<220> FEATURE:
<223> OTHER INFORMATION: RACE primer

<400> SEQUENCE: 40
cctattctcg ccttccactc cacc                                          24

<210> SEQ ID NO 41
<211> LENGTH: 24
<212> TYPE: DNA
<213> ORGANISM: Artificial
<220> FEATURE:
<223> OTHER INFORMATION: RACE primer

<400> SEQUENCE: 41
gaaatgggcg ttctggccct cgcg                                          24

<210> SEQ ID NO 42
<211> LENGTH: 24
<212> TYPE: DNA
<213> ORGANISM: Artificial
<220> FEATURE:
<223> OTHER INFORMATION: RACE primer

<400> SEQUENCE: 42
ctggccctcg cgaggcagtg cgac                                          24

<210> SEQ ID NO 43
<211> LENGTH: 23
<212> TYPE: DNA
<213> ORGANISM: Artificial
<220> FEATURE:
<223> OTHER INFORMATION: RACE primer

<400> SEQUENCE: 43
gccctccacc aagcccgcgc acg                                           23

<210> SEQ ID NO 44
<211> LENGTH: 22
<212> TYPE: DNA
<213> ORGANISM: Artificial
<220> FEATURE:
<223> OTHER INFORMATION: RACE primer

<400> SEQUENCE: 44
ccgaggggct gagcccgcgg gg                                            22

<210> SEQ ID NO 45
<211> LENGTH: 22
<212> TYPE: DNA
<213> ORGANISM: Artificial
<220> FEATURE:
<223> OTHER INFORMATION: RACE primer

<400> SEQUENCE: 45
cagcgttgat cacgtgacgt gg                                            22

<210> SEQ ID NO 46
<211> LENGTH: 24
<212> TYPE: DNA
<213> ORGANISM: Artificial
<220> FEATURE:
<223> OTHER INFORMATION: RACE primer

<400> SEQUENCE: 46
```
cccgcagccc acctctcggg ggcg                                            24

<210> SEQ ID NO 47
<211> LENGTH: 23
<212> TYPE: DNA
<213> ORGANISM: Artificial
<220> FEATURE:
<223> OTHER INFORMATION: RACE primer

<400> SEQUENCE: 47
ggctcccggc gctagcaggg ctg                                             23

<210> SEQ ID NO 48
<211> LENGTH: 23
<212> TYPE: DNA
<213> ORGANISM: Artificial
<220> FEATURE:
<223> OTHER INFORMATION: RACE primer

<400> SEQUENCE: 48
gtaaaggatg ttcatgaaga ttc                                             23

<210> SEQ ID NO 49
<211> LENGTH: 26
<212> TYPE: DNA
<213> ORGANISM: Artificial
<220> FEATURE:
<223> OTHER INFORMATION: RACE primer

<400> SEQUENCE: 49
gcatttgaaa acaagtaagt gtctcg                                          26

<210> SEQ ID NO 50
<211> LENGTH: 24
<212> TYPE: DNA
<213> ORGANISM: Artificial
<220> FEATURE:
<223> OTHER INFORMATION: RACE primer

<400> SEQUENCE: 50
tcagtccctg cagggtcctt gttt                                            24

<210> SEQ ID NO 51
<211> LENGTH: 29
<212> TYPE: DNA
<213> ORGANISM: Artificial
<220> FEATURE:
<223> OTHER INFORMATION: RACE primer

<400> SEQUENCE: 51
cttccatgat ggcggaacat gacctagtc                                       29

<210> SEQ ID NO 52
<211> LENGTH: 22
<212> TYPE: DNA
<213> ORGANISM: Artificial
<220> FEATURE:
<223> OTHER INFORMATION: RACE primer

<400> SEQUENCE: 52
catgacctag tctggggtgg ag                                              22

<210> SEQ ID NO 53
<211> LENGTH: 23
<212> TYPE: DNA
<213> ORGANISM: Artificial
<220> FEATURE:

-continued

<223> OTHER INFORMATION: RACE primer

<400> SEQUENCE: 53 ggagaaggggg agatgattcc agc                                          23

<210> SEQ ID NO 54
<211> LENGTH: 26
<212> TYPE: DNA
<213> ORGANISM: Artificial
<220> FEATURE:
<223> OTHER INFORMATION: RACE primer

<400> SEQUENCE: 54
gctggtatcc aactgagaag ttgacg                                        26

<210> SEQ ID NO 55
<211> LENGTH: 22
<212> TYPE: DNA
<213> ORGANISM: Artificial
<220> FEATURE:
<223> OTHER INFORMATION: RACE primer

<400> SEQUENCE: 55
cgactgccag cattgaactt ag                                            22

<210> SEQ ID NO 56
<211> LENGTH: 23
<212> TYPE: DNA
<213> ORGANISM: Artificial
<220> FEATURE:
<223> OTHER INFORMATION: RACE primer

<400> SEQUENCE: 56
cttagtacct agcaaagtag gtg                                           23

<210> SEQ ID NO 57
<211> LENGTH: 28
<212> TYPE: DNA
<213> ORGANISM: Artificial
<220> FEATURE:
<223> OTHER INFORMATION: RACE primer

<400> SEQUENCE: 57
cacttgaggt tcatttctgc ccctactg                                      28

<210> SEQ ID NO 58
<211> LENGTH: 22
<212> TYPE: DNA
<213> ORGANISM: Artificial
<220> FEATURE:
<223> OTHER INFORMATION: RACE primer

<400> SEQUENCE: 58
caaatgcatc cggttatccc ag                                            22

<210> SEQ ID NO 59
<211> LENGTH: 25
<212> TYPE: DNA
<213> ORGANISM: Artificial
<220> FEATURE:
<223> OTHER INFORMATION: RACE primer

<400> SEQUENCE: 59
ggtgcactca gtggcgtggg aaatc                                         25

<210> SEQ ID NO 60

```
<211> LENGTH: 151
<212> TYPE: DNA
<213> ORGANISM: Homo sapiens

<400> SEQUENCE: 60
acttccagtt actaatacac aagactctct ggtttctttc ttcacattca agggaattaa      60
gacgtaagga tcaataccat acaataaggg acctccagga cattagcaga aacagtcatt     120
ccattagttt aatactgagt tgttcagaaa c                                    151

<210> SEQ ID NO 61
<211> LENGTH: 182
<212> TYPE: DNA
<213> ORGANISM: Homo sapiens

<400> SEQUENCE: 61
gcctgactga ggccgaaccc ccggcccgct gcgggtgtaa acactgaaac cacgtcacgt      60
gatcaacgct gttccctccc ccgcgggct cagcccctcg gccccgccct ctctcttcaa     120
gtggcctggg agcgcgcgca tgcgcgctgc tgggaaccgg ccggggtgcc gggtcgaaag    180
ac                                                                    182

<210> SEQ ID NO 62
<211> LENGTH: 24
<212> TYPE: DNA
<213> ORGANISM: Artificial
<220> FEATURE:
<223> OTHER INFORMATION: RT-PCR primer

<400> SEQUENCE: 62
tgatgagaga ccacacaagt gcca                                             24

<210> SEQ ID NO 63
<211> LENGTH: 24
<212> TYPE: DNA
<213> ORGANISM: Artificial
<220> FEATURE:
<223> OTHER INFORMATION: RT-PCR primer

<400> SEQUENCE: 63
ctgcacaaac tgcactgaaa cgga                                             24

<210> SEQ ID NO 64
<211> LENGTH: 23
<212> TYPE: DNA
<213> ORGANISM: Artificial
<220> FEATURE:
<223> OTHER INFORMATION: RT-PCR primer

<400> SEQUENCE: 64
catgaagatt caataacagt tgc                                              23

<210> SEQ ID NO 65
<211> LENGTH: 22
<212> TYPE: DNA
<213> ORGANISM: Artificial
<220> FEATURE:
<223> OTHER INFORMATION: RT-PCR primer

<400> SEQUENCE: 65
cactttagct aaccaccaac ag                                               22

<210> SEQ ID NO 66
<211> LENGTH: 22
<212> TYPE: DNA
```

```
<213> ORGANISM: Artificial
<220> FEATURE:
<223> OTHER INFORMATION: RT-PCR primer

<400> SEQUENCE: 66
ctcatttgga attttgccga tt                                        22

<210> SEQ ID NO 67
<211> LENGTH: 21
<212> TYPE: DNA
<213> ORGANISM: Artificial
<220> FEATURE:
<223> OTHER INFORMATION: RT-PCR primer

<400> SEQUENCE: 67
ccgagtgaag atcccctttt a                                         21
```